US011299496B2

(12) United States Patent
Thakur et al.

(10) Patent No.: US 11,299,496 B2
(45) Date of Patent: Apr. 12, 2022

(54) LIGANDS FOR ALPHA-7 NICOTINIC ACETYLCHOLINE RECEPTORS AND METHODS OF TREATING NEUROLOGICAL AND INFLAMMATORY CONDITIONS

(71) Applicants: Northeastern University, Boston, MA (US); University of Florida Research Foundation, Inc., Gainesville, FL (US)

(72) Inventors: Ganeshsingh A. Thakur, Cambridge, MA (US); Abhijit R. Kulkarni, Boston, MA (US); Roger Lee Papke, Gainesville, FL (US)

(73) Assignees: Northeastern University, Boston, MA (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/328,112

(22) PCT Filed: Jul. 23, 2015

(86) PCT No.: PCT/US2015/041822
§ 371 (c)(1),
(2) Date: Jan. 23, 2017

(87) PCT Pub. No.: WO2016/014847
PCT Pub. Date: Jan. 28, 2016

(65) Prior Publication Data
US 2017/0217984 A1    Aug. 3, 2017

Related U.S. Application Data

(60) Provisional application No. 62/028,009, filed on Jul. 23, 2014.

(51) Int. Cl.
*C07D 495/04* (2006.01)
*C07D 221/16* (2006.01)
*C07D 401/04* (2006.01)
*C07D 401/10* (2006.01)
*C07D 401/12* (2006.01)
*C07D 405/04* (2006.01)
*C07D 409/04* (2006.01)
*C07D 409/10* (2006.01)
*C07D 409/14* (2006.01)
*C07D 417/04* (2006.01)
*C07D 491/048* (2006.01)

(52) U.S. Cl.
CPC ......... *C07D 495/04* (2013.01); *C07D 221/16* (2013.01); *C07D 401/04* (2013.01); *C07D 401/10* (2013.01); *C07D 401/12* (2013.01); *C07D 405/04* (2013.01); *C07D 409/04* (2013.01); *C07D 409/10* (2013.01); *C07D 409/14* (2013.01); *C07D 417/04* (2013.01); *C07D 491/048* (2013.01)

(58) Field of Classification Search
CPC ................ C07D 471/16; C07D 221/16; C07D 401/14; C07D 495/04; C07D 401/04; C07D 401/10; C07D 401/12; C07D 405/04; C07D 409/04; C07D 409/10; C07D 409/14; C07D 417/04; C07D 491/048; A61P 25/00; A61P 25/16; A61P 25/18; A61P 27/02; A61P 29/00
USPC .......................................................... 546/79
See application file for complete search history.

(56) References Cited

U.S. PATENT DOCUMENTS

| 6,416,735 B1 | 7/2002 | Carroll et al. |
| 2004/0180889 A1* | 9/2004 | Suto ............... A61K 31/40 514/235.2 |
| 2007/0043234 A1* | 2/2007 | Vaultier .......... C07B 37/02 562/1 |
| 2007/0078147 A1 | 4/2007 | Schumacher et al. |
| 2007/0179172 A1 | 8/2007 | Becker et al. |
| 2010/0099684 A1 | 4/2010 | Cook et al. |

FOREIGN PATENT DOCUMENTS

| WO | WO-2004098600 A1 * | 11/2004 | ........... A61K 31/47 |
| WO | WO-2007048042 A2 * | 4/2007 | ........ A61K 31/5375 |
| WO | 2012016133 A2 | 2/2012 | |
| WO | 2013123081 A2 | 8/2013 | |
| WO | WO-2013123081 A2 * | 8/2013 | |

OTHER PUBLICATIONS

Govindarajulu Babu et al. Imino Dies-Alser reactions catalyzed by Indium Trichloride (InCl3). Facile Synthesis of Quinoline and Phenanthridinone Derivatives. (Year: 1997).*
Powell david et al, Tetrahedron letters, pp. 7569-7573. (Year: 2003).*
Gowhar Ali, Input of Isosteric and Bioisosteric Approach to Drug design (Year: 2013).*
Bhatia et al. A review on Bioisosterism (Year: 2011).*
Thakur G et al. Expeditious Synthesis, Enantiomeric Resolution, and Enantiomer Functional Characterization of (4-(4-Bromophenyl)-3a,4,5,9btetrahydro-3H-cyclopenta[c]quinoline-8-sulfonamide (4BP-TQS): An Allosteric Agonist-Positive Allosteric Modulator of α7 Nicotinic Acetylcholine Receptors. J. Med. Chem. 2013, 56, 8943-8947.
Gill J. Agonist activation of α7 nicotinic acetylcholine receptors via an allosteric transmembrane site. PNAS. 108(14), 2011, 5867-5872.

(Continued)

Primary Examiner — John M Mauro
(74) Attorney, Agent, or Firm — Verrill Dana, LLP

(57) ABSTRACT

Compounds are provided which bind to an allosteric site on the mammalian alpha-7 nicotinic acetylcholine receptor (alpha-7 nAChR) and act as positive allosteric modulators with or without allosteric agonist activity. The compounds are useful in diagnosing, preventing, or treating a variety of disorders involving cognition, learning, memory, neurodegeneration, drug addiction, inflammation, chronic pain, and neuropathic pain. The compounds also can be used to enhance memory and learning in normal individuals.

10 Claims, 8 Drawing Sheets

(56) References Cited

OTHER PUBLICATIONS

J.H. Gronlien, et al., "Distinct Profiles of alpha-7 nAChR Positive Allosteric Modulation Revealed by Structurally Diverse Chemotypes", Molecular Pharmacology, Jun. 12, 2007, vol. 72, No. 3, pp. 715-724.
J.K. Gill, et al., "A Series of alpha-7 Nicotinic Acetylcholine Receptor Allosteric Modulators with Close Chemical Similarity but Diverse Pharmacological Properties", Molecular Pharmacology, Feb. 10, 2012, vol. 81, No. 5, pp. 710-718.
A.R. Kulkarni, et al., "Microwave-assisted expeditious and efficient synthesis of cyclopentene ring-fused tetrahydroquinoline derivatives using three-component Povarov reaction", Tetrahedron Letters, Sep. 27, 2013, vol. 54, No. 48, pp. 6592-6595.
V. V. Vintonyak, et al., "Identification and further development of thiazolidinones spiro-fused to indolin-2-ones as potent and selective inhibitors of *Mycobacterium tuberculosis* protein tyrosine phosphatase B", Tetrahedron, Apr. 7, 2011, vol. 67, No. 35, pp. 6713-6729.

\* cited by examiner

GAT1309  GAT1310  GAT1311  GAT1314  GAT1309

GAT1319  GAT1328  GAT1323  GAT145  GAT158

GAT1327  GAT150  GAT1324

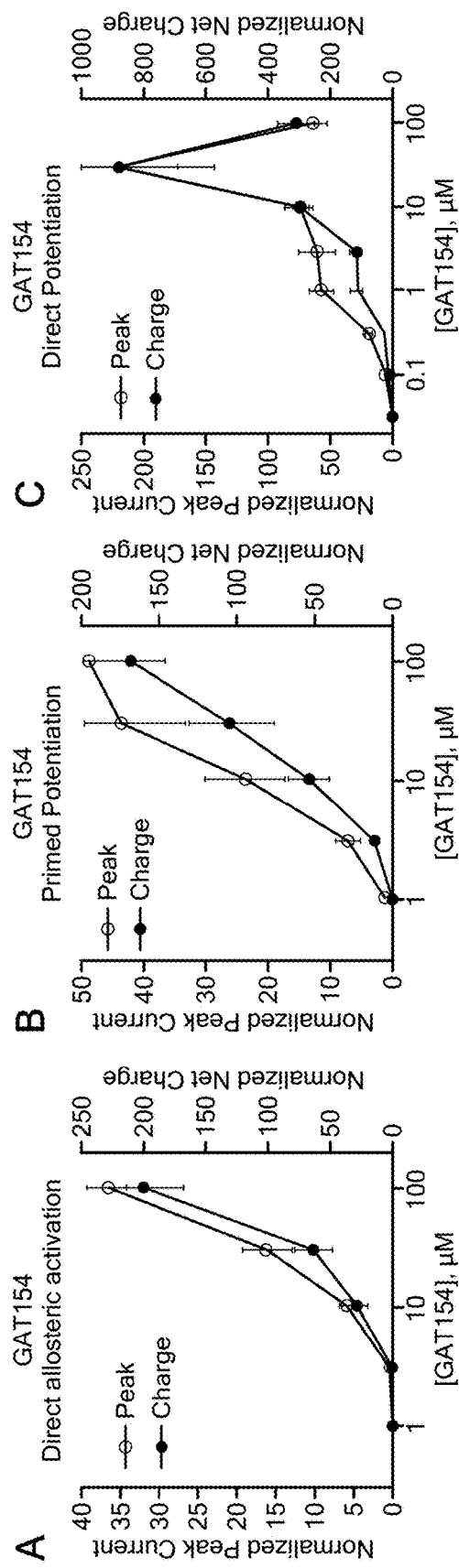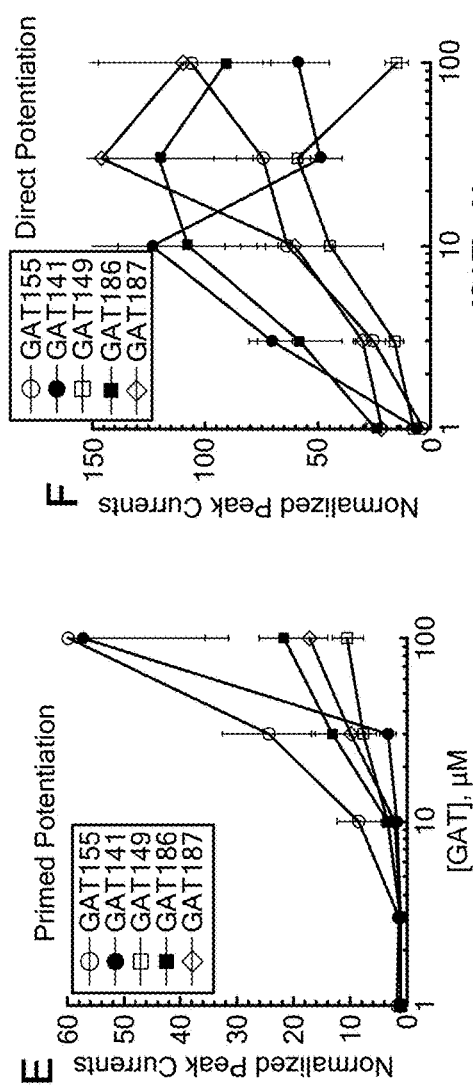
Fig. 2A Fig. 2B Fig. 2C Fig. 2D Fig. 2E Fig. 2F

LIGANDS FOR ALPHA-7 NICOTINIC ACETYLCHOLINE RECEPTORS AND METHODS OF TREATING NEUROLOGICAL AND INFLAMMATORY CONDITIONS

STATEMENT REGARDING FEDERALLY SPONSORED RESEARCH OR DEVELOPMENT

The invention was developed with financial support from Grant No. GM057481 from the National Institutes of Health. The U.S. Government has certain rights in the invention.

BACKGROUND

Nicotinic acetylcholine receptors (nAChR) are members of Cys-loop superfamily of cationic ligand-gated ion channels which are involved in physiological responses to the neurotransmitter acetylcholine (ACh) and are distributed throughout the central and peripheral nervous systems. Several distinct nAChR subtypes have been identified based on subunit composition and stoichiometry. The homopentameric alpha-7 nAChR subtype (also referred to herein as alpha-7 nAChR) is distinguished from the other nAChRs by its relatively high permeability to $Ca^{2+}$, rapid activation and desensitization (<100 ms) following exposure to agonist and sensitivity to antagonists such as α-bungarotoxin and methyllycaconitine (MLA). The alpha-7 nAChR is expressed at high levels in areas involved with learning and memory and plays a pivotal role in modulating neurotransmission in these areas. It has been considered a promising target for improving cognitive impairments in diseases such as Alzheimer's (AD) and schizophrenia as well as for treatment of inflammation, chronic pain, and neuropathic pain.

In recent years, a variety of structurally distinct, subtype-selective alpha-7 nAChR agonists have been developed and profiled. However, rapid desensitization of alpha-7 nAChR in response to high agonist concentration in vitro together with the possibility of endogenous tone disruption has led to concerns regarding utility of such agonists as clinical candidates. An alternative therapeutic approach is the development of positive allosteric modulators (PAMs) of alpha-7 nAChR which can synergize and augment orthosteric-site-mediated signaling of endogenous acetylcholine (ACh) without, in most cases, directly activating or desensitizing the receptor.

Selective PAMs of alpha-7 nAChR can be classified as Type I or Type II. Type I PAMs increase peak agonist-evoked electrophysiological responses but have little or no effect on the decay rate of macroscopic currents or the equilibrium desensitization of alpha-7 nAChR. Type II PAMs both increase peak currents and slow down the apparent desensitization profile of the agonist response. Both Type I and Type II PAMs have been reported to show efficacy in animal models of cognition; however, only Type II PAMs are effective in chronic and neuropathic pain models. Additional PAMs displaying properties intermediate between Type I and Type II also have been identified. Originally described PAMs of alpha-7 nAChR, such as tetrahydroquinoline-8-sulfonamide (TQS), lack allosteric agonist activity. However, PAMs which also have allosteric agonist activity also exist, and are referred to herein as ago-PAMs. Although, several examples of ago-PAMs have been reported for G-protein coupled receptors, the availability of such modulators for ion-channel receptors is limited.

An analog of TQS, namely 4-(4-bromophenyl)-3a,4,5,9b-tetrahydro-3H-cyclopenta[c]quinoline-8-sulfonamide (4BP-TQS), has been shown to possess allosteric agonism for alpha-7 nAChR in addition to Type II PAM activity (J. K. Gill, et al., Proc. Natl. Acad. Sci. USA 108, 5867-5872 (2010)). 4BP-TQS causes agonism through a site topographically distinct from the ACh binding site and is a more potent and effective agonist of alpha-7 nAChRs than ACh itself (8-fold lower $EC_{50}$ and 45-fold larger maximal response). Acting as an allosteric agonist, 4BP-TQS produced less equilibrium desensitization than would be seen with orthosteric agonists (e.g. ACh). 4BP-TQS is thus far the most potent ago-PAM of the alpha-7 nAChR available.

There remains a need to develop PAMs and ago-PAMs of alpha-7 nAChR with selective electrophysiological properties that can be utilized to treat medical conditions related to the central and peripheral effects of ACh.

SUMMARY OF THE INVENTION

The invention provides compounds which bind to an allosteric site on the mammalian alpha-7 nicotinic acetylcholine receptor (alpha-7 nAChR) and act as positive allosteric modulators with or without allosteric agonist activity. The compounds can be used to diagnose, prevent, or treat a variety of disorders in a mammalian subject, including disorders involving cognition, learning, memory, neurodegeneration (e.g., Alzheimer's disease, Parkinson's disease, macular degeneration), drug addiction, inflammation, chronic pain, and neuropathic pain. The compounds also can be used to enhance memory and learning in normal individuals.

One aspect of the invention is a compound of Formula I:

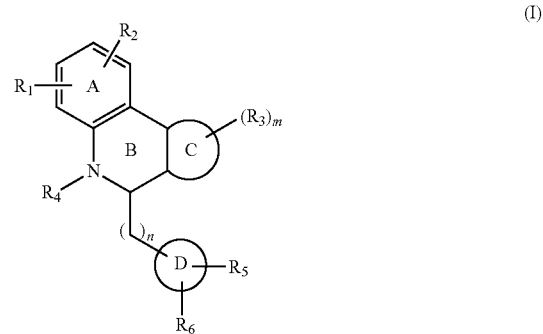

(I)

The A ring can be an aromatic or heteroaromatic five or six membered ring containing one or more heteroatom such as N, O, or S.

$R_1$ can be independently selected from $—SO_2NH_2$, $SO_2NR_aR_b$, COOH, $CONH_2$ and $CONR_aR_b$, and H. In $R_1$, each occurrence of $R_a$ and $R_b$ is independently selected from H, alkyl (C1-C6), alkenyl (C2-C6), alkynyl (C2-C6), alkoxy (C2-C6), cycloalkyl (C3-C7), alkylthio, alkylaryl, and aromatic and hetroaromatic rings. The aromatic and heteroaromatic rings can be further substituted with electron withdrawing and donating groups. Ra and Rb can form a cyclic ring (C3-C7) or an aromatic ring optionally containing one or more heteroatoms. Such aromatic rings can be further substituted with electron withdrawing groups such as halogens, —COOH, —CN, $—NO_2$ and the like, or electron donating groups such as alkyl groups.

$R_2$ can be H, halogen, or a heteroatom such as N, O, or S.
Ring A can be an aromatic or heteroaromatic ring (5 or 6 membered).

Ring B can be a six membered saturated or aromatic ring containing N at the indicated position. The nitrogen of ring B optionally can be substituted with an alkyl, aryl, or alkaryl substituent.

Ring C can be an independently a substituted or unsubstituted carbocyclic ring, bicyclic ring, aromatic ring, fused aromatic rings, or a heteroaromatic ring. Additionally, when it is a carbocyclic ring. It may contain one or more double bonds and one or more heteroatoms such as N, O, or S. It may also have an α-β unsaturated ketone function.

$R_3$ is selected independently from H, halogen, OH, CN, (C1-C6) alkyl, (C2-C6) alkenyl, (C2-C6) alkynyl, (C1-C6) alkoxy, (C3-C7) cycloalkyl, (C1-C6) alkylthio, $NR_aR_b$, $R_aR_b$ or halollkyl (e.g., $CF_3$). In $R_3$, each occurrence of $R_a$ and $R_b$ is independently hydrogen or (C1-C6) alkyl, or $R_a$ and $R_b$, form a saturated or unsaturated heterocyclic ring containing from three to seven ring atoms, which ring may optionally contain another heteroatom selected from N, O, and S, and may be optionally substituted by from one to three groups which may be the same or different and are selected from (C1-C4) alkyl, phenyl, and benzyl; and m is 1-4.

Rings B and C are preferably cis fused.

Rings D and B can be directly connected or can be connected through a spacer (C1-C2). When connected directly, they can be cis or trans with respect to the fusion of Ring B and C. Ring D is an aromatic or heteroaromatic ring containing one or more heteroatoms such as N, O, or S. It can be optionally substituted with $R_5$ and $R_6$ groups selected independently, or with $-R_6R_5$ or $R_5R_6$.

$R_5$ is independently selected from H, halogen, electron donating groups, and electron withdrawing groups such as alkyl, haloalkyl, alkoxy, $-NO_2$, $-SF_5$, $-CN$, and the like.

$R_6$ can be $NHC(O)OR_c$, $OC(O)NHR_c$, $C(O)O(CH_2)_nR_c$, $OC(O)(CH_2)_nR_c$, $C(O)NHR_c$, or $NHC(O)R_c$, where n=0, 1, 2, 3, or 4; or $R_6$ can be alkyl, branched alkyl (C1-C10), alkynyl (C1-C10), a carbocyclic ring, alkenyl (C1-C10), halogen, CN, COOH, $CONH_2$, OH, or $NH_2$. $R_c$ can be alkyl, branched alkyl (C1-C10), alkoxy, alkylamino, acyl, alkynyl (C1-C8) or alkenyl (C1-C6). $R_6$ can also be $X(CH_2)_n$-E, wherein X is NH, O, S, C≡C, or HC=CH, and n=0, 1, or 2, and E is independently a substituted or unsubstituted carbocyclic ring, bicyclic ring, aromatic ring, fused aromatic rings or heteroaromatic ring.

Another aspect of the invention is a compound of Formula II:

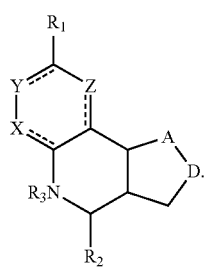

(II)

$R_1$ can be selected from the group consisting of carboxyl, carboxamide, carboxyalkyl, carboxyaryl, cyano, nitro, hydroxyl, sulfonyl, sulfonamide, alkylsulfonamide, arylsulfonamide, alkylsulfonyl, aralkylsulfonamide, trifluoromethylsulfonamide, trifluoromethylsulfonyl carboxamide, and sulfonylcarbamide. In preferred embodiments, R1 is sulfonamide, alkylsulfonamide, or arylsulfonamide. $R_2$ can be a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano. $R_3$ can be H, or a C1-C5 alkyl or cycloalkyl group optionally substituted with one or more of cyano, nitro, and one or more aromatic or heteroaromatic groups containing N, O, or S. A and D can be independently selected from CH, $CH_2$, N, and O, and the bond joining them is a single or double bond as appropriate for the selected atoms. X, Y, and Z are independently selected from no atom (i.e., they are absent), CH, C-halogen, N, O, and S. The compound binds to alpha-7 nAChR. In certain embodiments, the compound is not 4-(naphthalen-1-yl)-3a,4,5,9b-tetrahydro-3H-cyclopenta[c] quinoline-8-sulfonamide or 4-(4-bromophenyl)-3a,4,5,9b-tetrahydro-3H-cyclopenta[c]quinoline-8-sulfonamide.

Another aspect of the invention is a compound of Formula III:

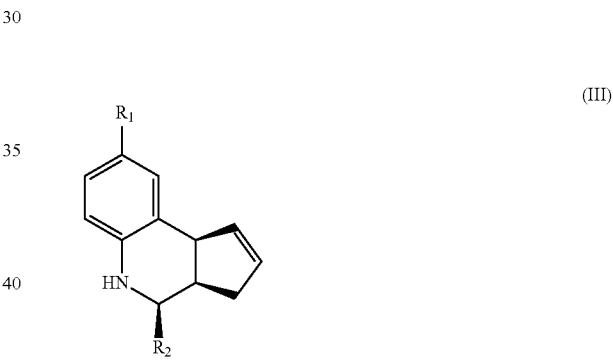

(III)

where $R_1$ and $R_2$ are as defined above for Formula II. In certain embodiments, the compound is not (3aR,4S,9bS)-4-(4-bromophenyl)-3a,4,5,9b-tetrahydro-3H-cyclopenta[c] quinoline-8-sulfonamide. In other embodiments, the compound is (3aR,4S,9bS)-4-(4-bromophenyl)-3a,4,5,9b-tetrahydro-3H-cyclopenta[c]quinoline-8-sulfonamide.

Still another aspect of the invention is a compound of Formula III, wherein $R_2$ is a substituent represented by $-R_dR_eR_f$ or by $-R_dCOR_eR_f$, wherein $R_d$, $R_e$, and $R_f$ are independently selected from a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano.

Another aspect of the invention is a compound having Formula IV:

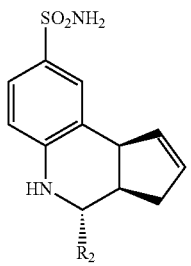

(IV)

where $R_2$ is as defined above for Formula II.

In preferred embodiments, the compounds of Formulas I, II, III, and IV are substantially enantiomerically pure.

Still another aspect of the invention is a labeled compound of any of Formulas I, II, III, and IV. The compound includes one or more of the following as a covalently bound portion of the molecule: $^{18}F$, $^{19}F$, $^{75}Br$, $^{76}Br$, $^{123}I$, $^{124}I$, $^{125}I$, $^{131}I$, $^{11}C$, $^{13}C$, $^{13}N$, $^{15}O$, or $^{3}H$. The labeled compound can be in the form of an imaging agent containing the compound, or a pharmaceutically acceptable salt, hydrate, or solvate thereof, and an excipient.

In different embodiments of the compounds of Formulas I, II, III, and IV, the compound is a positive allosteric modulator of the alpha-7 nicotinic acetylcholine receptor, or the compound is an allosteric agonist of the alpha-7 nicotinic acetylcholine receptor, or the compound is a negative allosteric modulator of the alpha-7 nicotinic acetylcholine receptor, or the compound is an allosteric antagonist of the alpha-7 nicotinic acetylcholine receptor.

In different embodiments of the compounds of Formulas I, II, III, and IV, the compound is capable of improving cognitive function, learning, and/or memory deficit; or the compound is capable of reducing inflammation; or the compound is capable of reducing neuropathic pain or pain related to a cognitive disorder. These effects can be achieved in a mammalian subject, such as a human, dog, cat, horse, or livestock animal.

Yet another aspect of the invention is a pharmaceutical composition containing a compound of any Formulas I, II, III, or IV, or a pharmaceutically acceptable salt, hydrate, or solvate thereof, and an excipient.

A further aspect of the invention is a method of improving cognitive function, learning, and/or memory in a mammalian subject. The method includes administering to a subject in need thereof the compound of any of Formulas I, II, III, or IV, wherein the compound is an allosteric agonist or a positive allosteric modulator of alpha-7 nicotinic acetylcholine receptor.

Another aspect of the invention is a method of inhibiting inflammation. The method includes administering to a subject in need thereof the compound of any of Formulas I, II, III, or IV, wherein the compound is an allosteric agonist or a positive allosteric modulator of alpha-7 nicotinic acetylcholine receptor.

Yet another aspect of the invention is a method of treating drug addiction or Parkinson's disease. The method includes administering to a subject in need thereof the compound of any of Formulas I, II, III, or IV, wherein the compound is an allosteric antagonist or a negative allosteric modulator of alpha-7 nicotinic acetylcholine receptor.

Still another aspect of the invention is a method of treating neuropathic pain. The method includes administering to a subject in need thereof the compound of any of Formulas I, II, III, or IV, wherein the compound is an allosteric agonist or a positive allosteric modulator of alpha-7 nicotinic acetylcholine receptor.

Another aspect of the invention is a method of treating macular degeneration. The method includes administering to a subject in need thereof the compound of any of Formulas I, II, III, or IV, wherein the compound is an allosteric agonist or a positive allosteric modulator of alpha-7 nicotinic acetylcholine receptor.

BRIEF DESCRIPTION OF THE DRAWINGS

FIGS. 2A-2F show pharmacological effects of PAMs and agoPAMs of the invention using a Xenopus oocyte electrophysiological assay.

DETAILED DESCRIPTION OF THE INVENTION

Figure 1A:
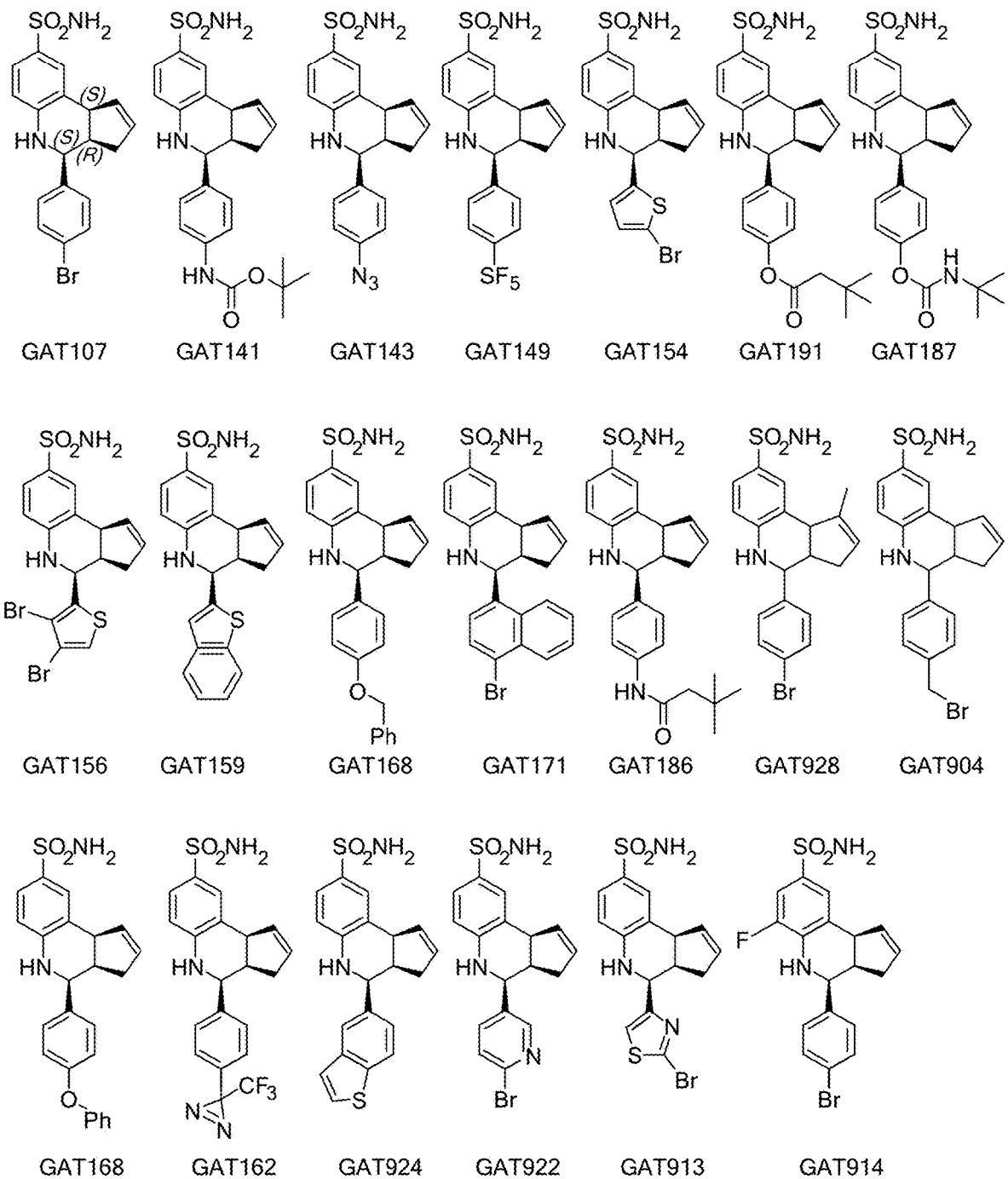
FIG. 1A shows a series of compounds with positive allosteric modulatory activity as well as allosteric agonist activity (i.e., agoPAMs) for the α7 nAChR.

The invention provides compounds which bind to an allosteric site on the mammalian alpha-7 nicotinic acetylcholine receptor (alpha-7 nAChR) and positively or negatively allosterically modulate the receptor's activity in the presence of the physiological ligand, acetylcholine (ACh), and/or act alone as agonists or antagonists of the receptor through the allosteric binding site. In addition to the compounds, the invention provides pharmaceutically acceptable salts, solvates, or hydrates of the compounds, methods for their synthesis, pharmaceutical compositions containing them, and use of the compounds or pharmaceutical compositions in therapy of a variety of disorders related to central and peripheral effects involving the alpha-7 nicotinic acetylcholine receptor (alpha-7 AChR), as well as in imaging or labeling the receptor in vivo. The compounds are useful in treating disorders involving cognition, learning, memory, neurodegeneration, drug (e.g., cannabis) addiction, macular degeneration, inflammation, chronic pain, and neuropathic pain. The compounds also can be used to enhance memory and learning in normal individuals.

The invention particularly relates to the method of synthesis and therapeutic use of Type I and Type II positive allosteric modulators (PAMs), which increase the tone of ACh, and PAMs with allosteric agonism (ago-PAMs), which cause direct activation of the receptor. The invention also relates to synthesis and therapeutic use of negative allosteric modulators (NAMs) and compounds with allosteric antagonism.

In one embodiment, compounds of the invention are represented by Formula I below.

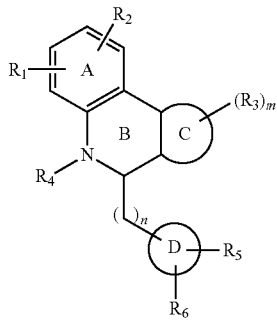

For the compounds according to Formula I:

The A ring can be an aromatic or heteroaromatic five or six membered ring containing one or more heteroatom such as N, O, or S.

$R_1$ can be independently selected from —$SO_2NH_2$, $SO_2NR_aR_b$, COOH, $CONH_2$ and $CONR_aR_b$, and H. In $R_1$, each occurrence of $R_a$ and $R_b$ independently selected from H, alkyl (C1-C6), alkenyl (C2-C6), alkynyl (C2-C6), alkoxy (C2-C6), cycloalkyl (C3-C7), alkylthio, alkylaryl, and aromatic and hetroaromatic rings. The aromatic and heteroaromatic rings can be further substituted with electron withdrawing and donating groups. Ra and Rb can form a cyclic ring (C3-C7) or an aromatic ring optionally containing one or more heteroatoms. Such aromatic rings can be further substituted with electron withdrawing groups such as halogens, —COOH, —CN, —$NO_2$ and the like, or electron donating groups such as alkyl groups.

$R_2$ can be H, halogen, or a heteroatom such as N, O, or S.

Ring A can be an aromatic or heteroaromatic ring (5 or 6 membered).

Ring B can be a six membered saturated or aromatic ring containing N at the indicated position. The nitrogen of ring B optionally can be substituted with an alkyl, aryl, or alkaryl substituent.

Ring C can be an independently a substituted or unsubstituted carbocyclic ring, bicyclic ring, aromatic ring, fused aromatic rings, or a heteroaromatic ring. Additionally, when it is a carbocyclic ring. It may contain one or more double bonds and one or more heteroatoms such as N, O, or S. It may also have an α-β unsaturated ketone function.

$R_3$ is selected independently from H, halogen, OH, CN, (C1-C6) alkyl, (C2-C6) alkenyl, (C2-C6) alkynyl, (C1-C6) alkoxy, (C3-C7) cycloalkyl, (C1-C6) alkylthio, $NR_aR_b$, $R_aR_b$ or halollkyl (e.g., $CF_3$). In $R_3$, each occurrence of $R_a$ and $R_b$ is independently hydrogen or (C1-C6) alkyl, or $R_a$ and $R_b$, form a saturated or unsaturated heterocyclic ring containing from three to seven ring atoms, which ring may optionally contain another heteroatom selected from N, O, and S, and may be optionally substituted by from one to three groups which may be the same or different and are selected from (C1-C4) alkyl, phenyl, and benzyl; and m is 1-4.

Rings B and C are preferably cis fused.

Rings D and B can be directly connected or can be connected through a spacer (C1-C2). When connected directly, they can be cis or trans with respect to the fusion of Ring B and C. Ring D is an aromatic or heteroaromatic ring containing one or more heteroatoms such as N, O, or S. It can be optionally substituted with $R_5$ and $R_6$ groups selected independently.

$R_5$ is independently selected from H, halogen, electron donating groups, and electron withdrawing groups such as alkyl, alkoxy, —$NO_2$, —$SF_5$, —CN, and the like.

$R_6$ can be NHC(O)$OR_c$, OC(O)$NHR_c$, C(O)O($CH_2$)$_nR_c$, OC(O)($CH_2$)$_nR_c$, C(O)$NHR_c$, or NHC(O)$R_c$, where n=0, 1, 2, 3, or 4; or $R_6$ can be alkyl, branched alkyl (C1-C10), alkynyl (C1-C10), a carbocyclic ring, alkenyl (C1-C10), halogen, CN, COOH, $CONH_2$, OH, or $NH_2$. $R_c$ can be alkyl, branched alkyl (C1-C10), alkynyl (C1-C8) or alkenyl (C1-C6). $R_6$ can also be X($CH_2$)$_n$-E, wherein X is NH, O, S, C≡C, or HC═CH, and n=0, 1, or 2, and E is independently a substituted or unsubstituted carbocyclic ring, bicyclic ring, aromatic ring, fused aromatic rings or heteroaromatic ring.

A compound of Formula I preferably binds to alpha-7 nAChR. More preferably, a compound of Formula I modulates an activity of alpha-7 nAChR. Still more preferable is that a compound of Formula I is a PAM or ago-PAM for alpha-7 nAChR. In certain embodiments, a compound of Formula I is a NAM or allosteric antagonist of alpha-7 nAChR.

For compounds of Formula I, the substituent on the southern part of the D ring is a determinant of ago-PAM activity. Further, the selection of a sulfonamide group as $R_1$ correlates positively with allosteric agonist activity and ago-PAM activity for all compounds. Within the cis isomer, blockade of the NH of the sulfonamide group induces allosteric antagonism, but this is not the case for the trans isomer.

In another embodiment, compounds of the invention Formula II below.

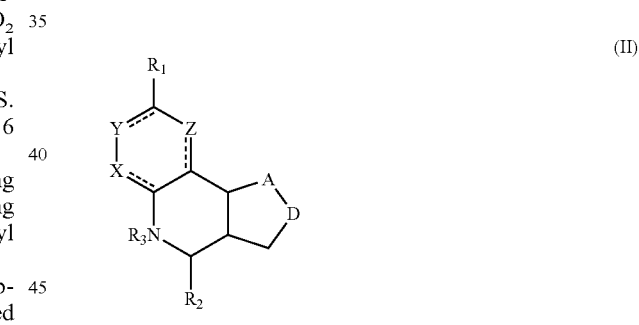

For the compounds of Formula II:

$R_1$ can be selected from the group consisting of carboxyl, carboxamide, carboxyalkyl, carboxyaryl, cyano, nitro, hydroxyl, sulfonyl, sulfonamide, alkylsulfonamide, arylsulfonamide, alkylsulfonyl, aralkylsulfonamide, trifluoromethylsulfonamide, trifluoromethylsulfonyl carboxamide, and sulfonylcarbamide.

$R_2$ can be a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano.

$R_3$ can be H, or a C1-C5 alkyl or cycloalkyl group optionally substituted with one or more of cyano, nitro, and one or more aromatic or heteroaromatic groups containing N, O, or S.

A and D can be independently selected from CH, CH$_2$, N, and O, and the bond joining them is a single or double bond as appropriate for the selected atoms. X, Y, and Z are independently selected from no atom (i.e., they are absent), CH, C-halogen, N, O, and S.

In certain embodiments, the compound is not 4-(naphthalen-1-yl)-3a,4,5,9b-tetrahydro-3H-cyclopenta[c]quinoline-8-sulfonamide or 4-(4-bromophenyl)-3a,4,5,9b-tetrahydro-3H-cyclopenta[c]quinoline-8-sulfonamide.

A compound of Formula II preferably binds to alpha-7 nAChR. More preferably, a compound of Formula II modulates an activity of alpha-7 nAChR. Still more preferable is that a compound of Formula II is a PAM or ago-PAM for alpha-7 nAChR. In certain embodiments, a compound of Formula II is a NAM or allosteric antagonist of alpha-7 nAChR.

Previously the most potent known PAM for alpha-7 nAChR was 4-(4-bromophenyl)-3a,4,5,9b-tetrahydro-3H-cyclopenta[c]quinoline-8-sulfonamide (4BP-TQS). This compound was initially studied exclusively in vitro and as a racemate. However, the compound has three chiral centers with the cyclopentene and 4-bromophenyl rings oriented cis to each other. The present inventors have performed enantioseparation and electrophysiological characterization of the entantiomerically pure compounds, and found that all the activity of the racemate of 4BP-TQS lies in one enantiomer, (3aR,4S,9bS)-4-(4-bromophenyl)-3a,4,5,9b-tetrahydro-3H-cyclopenta[c]quinoline-8-sulfonamide. The active enantiomer has a 3aR,4S,9bS configuration at the three chiral centers with the cyclopentene and 4-bromophenyl rings oriented cis to each other.

In yet another embodiment of the invention, the compounds have a structure according to Formula III.

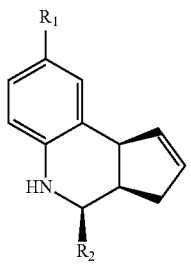

(III)

For the compounds of Formula III:

R$_1$ can be selected from the group consisting of carboxyl, carboxamide, carboxyalkyl, carboxyaryl, cyano, nitro, hydroxyl, sulfonyl, sulfonamide, alkylsulfonamide, arylsulfonamide, alkylsulfonyl, aralkylsulfonamide, trifluoromethylsulfonamide, trifluoromethylsulfonyl carboxamide, and sulfonylcarbamide.

R$_2$ can be a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano.

Alternatively, for compounds of Formula III, R$_2$ is a substituent represented by —R$_d$R$_e$R$_f$ or by —R$_d$COR$_e$R$_f$; wherein R$_d$, R$_e$, and R$_f$ are independently selected from a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano.

In preferred embodiments, the alpha-7 nAChR ligands of the invention are substantially enantiomerically pure. Such enantiomerically pure ligands have provided an understanding of the stereochemical requirement for the action of these compounds at the alpha-7 nAChR. Compounds having PAM activity enhance the orthosteric response of the receptor with or without desensitizing the receptor, thus leading to an increased cholinergic tone. Compounds behaving as ago-PAMs have an agonist activity of their own through the allosteric site and enhance the efficacy of orthosteric ligands, which in turn increases the cholinergic tone.

In still another embodiment, the compounds have a structure according to Formula IV.

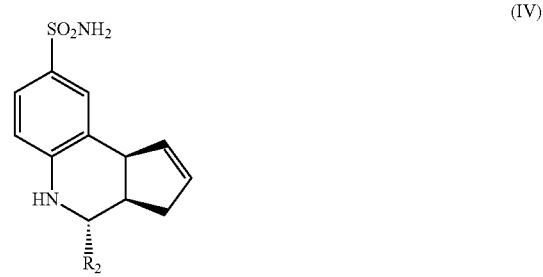

(IV)

For the compounds of Formula IV:

R$_2$ can be a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano.

Figure 1B:
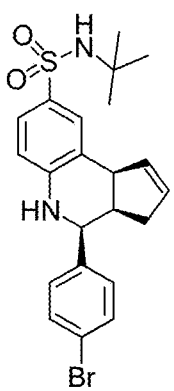
FIG. 1B shows a series of compounds with allosteric antagonist activity for the α7 nAChR.
Figure 1B:
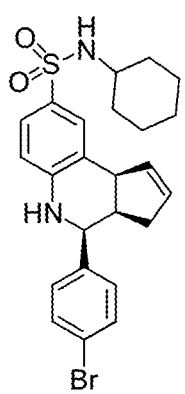
Figure 1B:
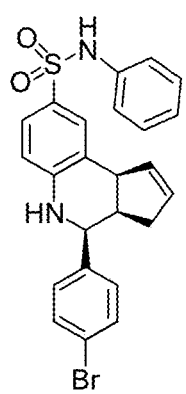
Figure 1B:
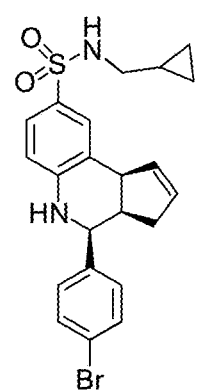
Figure 1B:
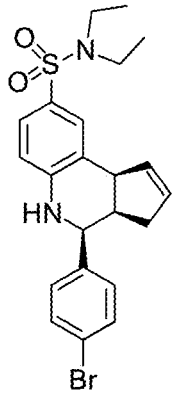
Figure 1B:
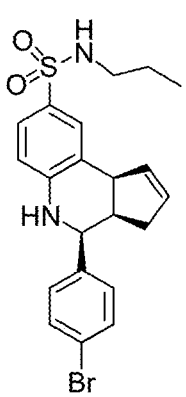
Figure 1B:
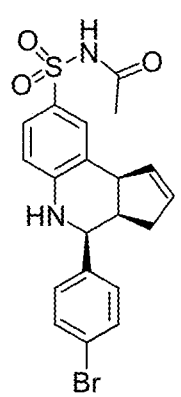
Figure 1B:
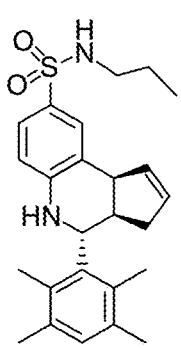
Figure 1B:
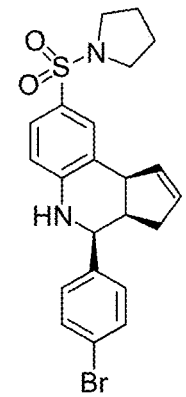
Figure 1B:
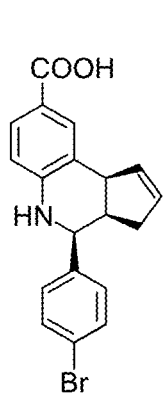
Figure 1B:
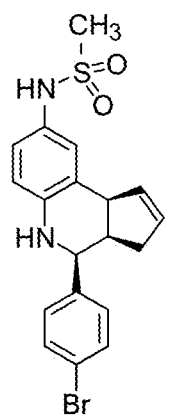
Figure 1B:
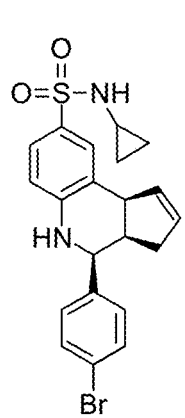
Figure 1B:
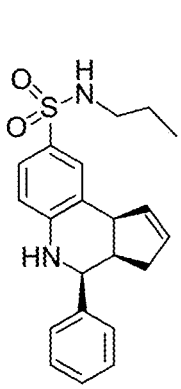

A number of specific compounds of the invention are shown in FIGS. 1A and 1B.

Alpha-7 nAChRs can be activated by orthosteric agonists (e.g., ACh) as well as allosteric agonists. Allosteric agonists of the present invention activate the receptors and keep them from being desensitized rapidly, unlike the orthosteric agonists which cause rapid desensitization. The allosteric agonists and ago-PAMs of the invention also act as positive allosteric modulators of the alpha-7 receptor where they increase the activity of the orthosteric ligands multifold. Electrophysiology studies described in the Examples helped to identify the PAMs and distinguish them from the ago-PAMs as well as the allosteric antagonists of the alpha-7 receptor.

Certain compounds, such as GAT141, possess an extended southern chain, such as a Boc protecting group. These compounds showed an increased 'ago' component in the electrophysiology experiments, suggesting that there is a secondary southern pocket present on the receptor which can be filled by linear alkyl chains with or without heteroatoms. With GAT168, a phenyl ring was also tolerated and led to moderate ago-PAM activity. This finding led to a series of molecules with comparatively good 'ago' and 'PAM' components.

In some embodiments, compounds of the invention are able to substantially cross the blood-brain barrier and are active at alpha-7 nAChR sites in the central nervous system. In some embodiments, compounds of the invention are not able to substantially cross the blood-brain barrier, and the compounds are active at alpha-7 nAChR sites in the periphery. In certain embodiments, compounds of the invention are effective at diagnosing, preventing, and/or treating any medical condition that involves a contribution by the alpha-7 nAChR. In some embodiments, compounds are Type II PAMs which increase cholinergic signalling at alpha-7 nAChR by reducing deactivation of ionic currents through the activated receptor, or by reducing desensitization of the receptor to ACh. In some embodiments, compounds are allosteric agonists that activate alpha-7 nAChR in the absence of stimulation by ACh; such compounds can be used to treat neurodegenerative conditions characterized by poor cholinergic tone. In some embodiments, compounds of the invention are neuroprotective; such compounds The compounds of the present invention can be used for the prophylaxis, diagnosis, or treatment of disorders related to cognition and memory such as Alzheimer's disease and other neurodegenerative diseases such as Parkinson's disease. The compounds also can b be used for prophylaxis, diagnosis, or treatment of schizophrenia, attention deficit disorder (ADD), and other learning or cognitive disorders. The compounds also are useful for treatment of neuropathic pain, in which an increase in cholinergic tone through alpha-7 nAChR can be effective for treatment. In Parkinson's disease a decrease in cholinergic tone can be useful, and allosteric antagonist compounds of the invention can be used for treatment. Peripheral effects of ACh at alpha-7 nAChR also can be enhanced using compounds of the invention, with helpful effects such as reduction of inflammation.

Examples

Example 1. Synthesis of PAMs for Alpha-7 nAChR

PAMs having the generic Formulas V and VI shown below were synthesized using the reaction schemes described further below.

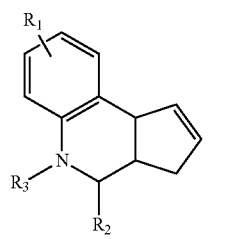
(V)

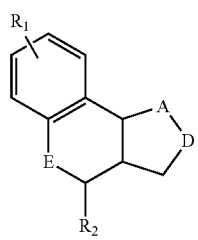
(VI)

Scheme I:

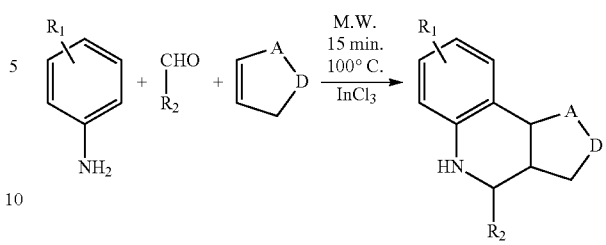

Alternatively, the reaction can be carried out for 24 h at room temperature in the presence of InCl$_3$.

Scheme II:

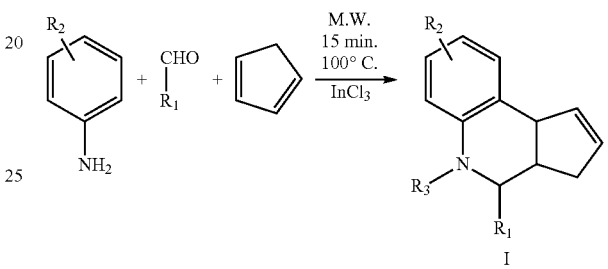

Alternatively, the reaction can be carried out for 24 h at room temperature in the presence of InCl$_3$.

Scheme III:

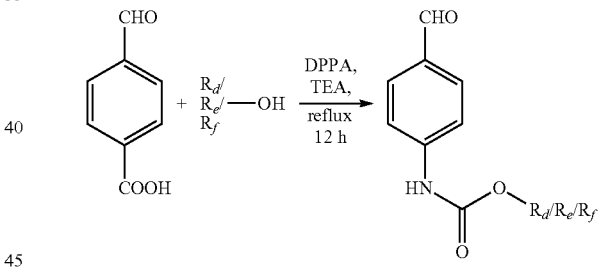

Scheme IV:

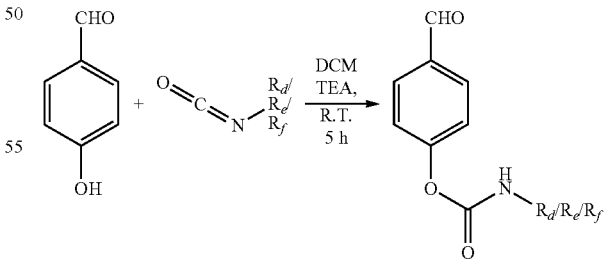

The general procedure for carrying out Scheme I or Scheme II was as follows.

Procedure A:

In a microwave vial, cyclopentadiene (3 equiv.) was added to a suspension of aldehyde (1 equiv.), sulfanilamide (1 equiv.) and indium trichloride (0.2 equiv.) in acetonitrile (9 mL). The reaction vial was placed in a microwave synthesizer and irradiated at 100° C. for 15 min.

Alternative Procedure B:

To a round bottom flask, cyclopentadiene (3 equiv.) was added to a suspension of aldehyde (1 equiv.), sulfanilamide (1 equiv.) and indium trichloride (0.2 equiv.) in acetonitrile (9 mL). The reaction mixture was stirred at room temperature for 24 h.

The reaction mixtures from Procedure A or Procedure B above were added to aqueous (0.1 M) Na$_2$CO$_3$ solution (20 mL) and extracted with chloroform (3×30 mL). The combined organic layer was washed with water (20 mL), and brine (30 mL), then dried over Na$_2$SO$_4$ and concentrated under reduced pressure. The residue was purified by chromatography and/or recrystallization to yield the desired compound.

Example 2. Synthesis of Selected PAMs for Alpha-7 nAChR

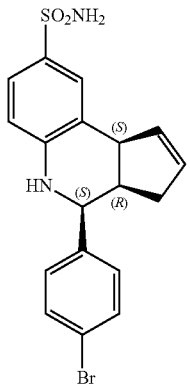

(3aR,4S,9bS)-4-(4-bromophenyl)-3a,4,5,9b-tetrahydro-3H-cyclopenta[c]quinoline-8-sulfonamide (GAT107, 1)

$^1$H NMR (500 MHz, DMSO-d6) δ7.59 (d, J=8.5 Hz, 2H, H-12, 14), 7.43 (d, J=2.0 Hz, 1H, H-9), 7.41 (d, J=8.5 Hz, 2H, H-11, 15), 7.34 (dd, J=8.5, 2 Hz, 1H, H-7), 6.96 (s, 2H, NH$_2$), 6.80 (d, J=8.5 Hz, 1H, H-6), 6.39 (bs, 1H, NH), 5.92-5.86 (m, 1H, H-1), 5.64-5.59 (m, 1H, H-2), 4.62 (d, J=3.5 Hz, 1H, H-4), 4.06 (d, J=8.5 Hz, 1H, H-9b), 2.98-2.88 (m, 1H, H-3a), 2.33 (ddd, J=16.5, 10, 2.5 Hz, 1H, H-3eq), 1.64 (bdd, J=16.5, 10 Hz, 2H, H-3ax).

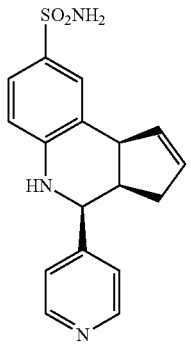 [SMILES: NS(=O)(=O)c1ccc2c(c1)[C@H]1C=CC[C@H]1[C@@H](c1ccncc1)N2]

4-(pyridin-4-yl)-3a,4,5,9b-tetrahydro-3H-cyclopenta[c]quinoline-8-sulfonamide (GAT108; 2)

$^1$H NMR (500 MHz, DMSO) δ 8.57 (d, J=6.0 Hz, 2H), 7.47 (d, J=6.0 Hz, 2H), 7.45 (d, J=2.0 Hz, 1H), 7.36 (dd, J=8.0 Hz, 2.0 Hz, 1H), 6.98 (s, 2H), 6.82 (d, J=9.0 Hz, 1H), 6.45 (brs, 1H), 5.92-5.87 (m, 1H), 5.61 (d, J=5.0 Hz, 1H), 4.65 (d, J=3.0 Hz, 1H), 4.09 (d, J=9.0 Hz, 1H), 3.01 (qdd, J=9.0 Hz, 3.0 Hz, 1.5 Hz, 1H), 2.31 (ddq, J=16.0 Hz, 9.0 Hz, 2.0 Hz, 1H), 1.62 (dd, J=15.0 Hz, 8.0 Hz, 1H)

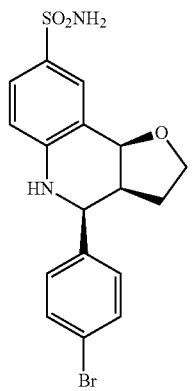 [SMILES: NS(=O)(=O)c1ccc2c(c1)[C@H]1OCC[C@H]1[C@@H](c1ccc(Br)cc1)N2]

4-(4-bromophenyl)-2,3,3a,4,5,9b-hexahydrofuro[3,2-c]quinoline-8-sulfonamide (GAT110; 3)

$^1$H NMR (500 MHz, DMSO) δ 7.65 (d, J=2.0 Hz, 1H, H-9), 7.61 (d, J=8.5 Hz, 2H, H-12, 14), 7.46 (dd, J=8.5 Hz, 2.0 Hz, 1H, H-7), 7.45 (d, J=8.5 Hz, 2H, H-11,15), 7.00 (s, 2H, H—NH$_2$), 6.97 (s, 1H, H—NH), 6.78 (d, J=8.5 Hz, 1H, H-6), 4.67 (d, J=3.5 Hz, 1H), 3.96-3.86 (m, 1H), 3.78-3.67 (m, 2H, esp. 3.73 (d, 1H)), 2.33-2.24 (m, 1H), 2.03-1.91 (m, 1H), 1.61-1.50 (m, 1H)

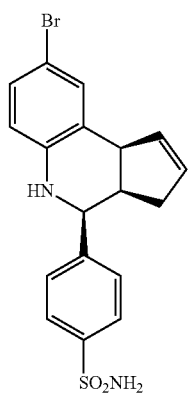 [SMILES: NS(=O)(=O)c1ccc([C@H]2Nc3ccc(Br)cc3[C@H]3C=CC[C@H]32)cc1]

4-(8-bromo-3a,4,5,9b-tetrahydro-3H-cyclopenta[c]quinolin-4-yl)benzenesulfonamide (GAT111; 4)

$^1$H NMR (500 MHz, DMSO-d6) δ 7.82 (d, J=8.5 Hz, 2H) 7.62 (d, J=8.5 Hz, 2H), 7.35 (s, 2H), 7.18 (d, J=2.5 Hz, 1H), 7.04 (dd, J=8.0 Hz, 2.5 Hz, 1H), 6.70 (d, J=8.5 Hz, 1H), 5.95 (s, 1H), 5.92-5.87 (m, 1H), 5.62-5.57 (m, 1H), 4.60 (d, J=3.5 Hz, 1H), 4.04 (d, J=8.0 Hz, 1H), 3.00-2.90 (m, 1H), 2.38 (ddd, J=16.0 Hz, 9.5 Hz, 2.0 Hz, 1H), 1.60 (dd, J=15.5 Hz, 9.0 Hz, 1H)

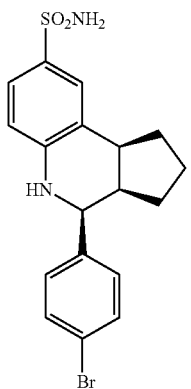 [SMILES: NS(=O)(=O)c1ccc2c(c1)[C@H]1CCC[C@H]1[C@@H](c1ccc(Br)cc1)N2]

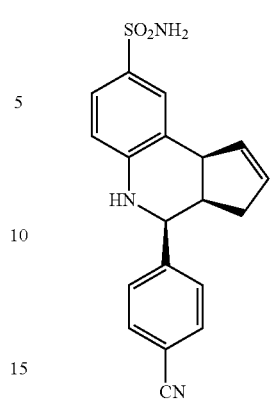

4-(4-bromophenyl)-2,3,3a,4,5,9b-hexahydro-1H-cyclopenta[c]quinoline-8-sulfonamide (GAT112; 5)

¹H NMR (500 MHz, DMSO-d6) δ 7.57 (d, J=8.5 Hz, 2H, H-12,14), 7.49 (d, J=2.0 Hz, 1H, H-9), 7.39 (d, J=8.5 Hz, 2H, H-11,15), 7.34 (dd, J=8.5 Hz, 2.0 Hz, 1H, H-7), 6.95 (s, 2H, H—NH$_2$), 6.75 (d, J=8.5 Hz, 1H, H-6), 6.54 (s, 1H, H—NH), 4.60 (d, J=2.5 Hz, 1H, H-4), 3.40 (t, J=6.5 Hz, 1H, H-9b), 2.43-2.37 (m, 1H,), 2.14 2.06 (m, 1H,), 1.86-1.78 (m, 1H,), 1.48-1.36 (m, 3H,), 1.12-1.04 (m, 1H,)

4-(4-cyanophenyl)-3a,4,5,9b-tetrahydro-1H-cyclopenta[c]quinoline-8-sulfonamide (GAT116; 7)

¹H NMR (500 MHz, DMSO-d6) δ 7.87 (d, J=8.5 Hz, 2H), 7.65 (d, J=8.5 Hz, 2H), 7.45 (d, J=2.0 Hz, 1H), 7.35 (dd, J=8.5 Hz, 2.5 Hz, 1H), 6.97 (s, 2H), 6.81 (d, J=9.0 Hz, 1H), 6.47 (s, 1H), 5.94-5.86 (m, 1H), 5.65-5.56 (m, 1H), 4.74 (d, J=3.0 Hz, 1H), 4.08 (d, J=8.5 Hz, 1H), 3.04-2.93 (dq as m, 1H), 2.31 (ddd, J=16.0 Hz, 9.5 Hz, 2.0 Hz, 1H), 1.59 (dd, J=15.0 Hz, 8.5 Hz, 1H)

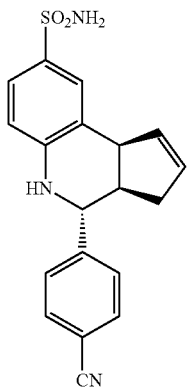 [SMILES: N#Cc1ccc([C@@H]2Nc3ccc(S(N)(=O)=O)cc3[C@H]3C=CC[C@H]32)cc1]

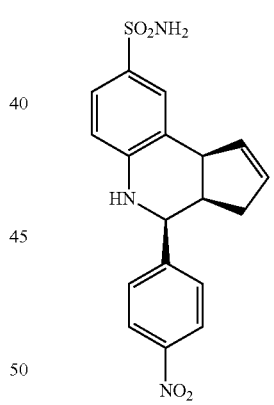

4-(4-cyanophenyl)-3a,4,5,9b-tetrahydro-3H-cyclopenta[c]quinoline-8-sulfonamide (GAT114; 6)

¹H NMR (500 MHz, DMSO-d6) δ 7.85 (d, J=8.5 Hz, 2H, H-12,14), 7.61 (d, J=8.0 Hz, 2H, H-11,15), 7.58 (d, J=2.0 Hz, 1H, H-9), 7.36 (dd, J=8.0 Hz, 2.0 Hz, 1H, H-7), 6.96 (s, 2H, H—NH$_2$), 6.72 (d, J=8.0 Hz, 1H, H-6), 6.69 (s, 1H, H—NH), 5.92-5.86 (m, 1H, H-1), 5.76-5.71 (m, 1H, H-2), 3.91-3.85 (m, 1H, H-4), 3.80 (d, J=9.5 Hz, 1H, H-9b), 2.66-2.58 (m, 1H, H-3a), 2.46-2.36 (m, 1H, H-3$_{eq}$), 2.04-1.96 (m, 1H, H-3$_{ax}$)

4-(4-nitrophenyl)-3a,4,5,9b-tetrahydro-3H-cyclopenta[c]quinoline-8-sulfonamide (GAT117; 8)

¹H NMR (500 MHz, DMSO) δ 8.27 (d, J=8.5 Hz, 2H), 7.74 (d, J=9.0 Hz, 2H), 7.46 (d, J=2.0 Hz, 1H), 7.36 (dd, J=8.5 Hz, 2.5 Hz, 1H), 6.98 (s, 2H), 6.82 (d, J=8.5 Hz, 1H), 6.53 (s, 1H), 5.95-5.86 (m, 1H), 5.65-5.57 (m, 1H), 4.80 (d, J=3.0 Hz, 1H), 4.10 (d, J=8.5 Hz, 1H), 3.07-2.95 (m, 1H), 2.33 (ddd, J=16.5 Hz, 10 Hz, 2 Hz, 1H), 1.60 (dd, J=15.5 Hz, 9.5 Hz, 1H)

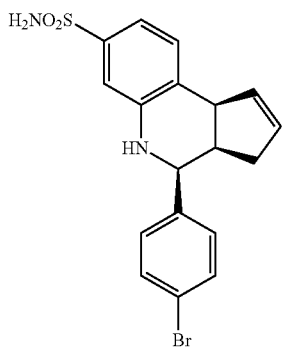 [SMILES: NS(=O)(=O)c1ccc2c(c1)N[C@H](c1ccc(Br)cc1)[C@@H]1CC=C[C@H]21]

4-(4-bromophenyl)-3a,4,5,9b-tetrahydro-3H-cyclopenta[c]quinoline-7-sulfonamide (GAT119; 10)

$^1$H NMR (400 MHz, CDCl3) δ 7.51 (m, 3H), 7.28 (d, J=8.4 Hz, 2H), 7.25 (dd, J=7.2 Hz, 1.6 Hz, 1H), 7.17 (d, J=1.6 Hz, 1H), 7.15 (d, J=7.2 Hz, 1H), 5.82-5.80 (m, 1H), 5.69-5.67 (m, 1H), 4.77 (s, 2H), 4.62 (d, J=3.0 Hz, 1H), 4.11 (d, J=8.1 Hz, 1H), 2.99 (dtd, J=9.1 Hz, 8.1 Hz, 3.0 Hz, 1H), 2.53 (dtd, J=16.4 Hz, 9.1 Hz, 3.0 Hz, 1H), 1.81 (br dd, J=16.4 Hz, 8.1 Hz, 1H)

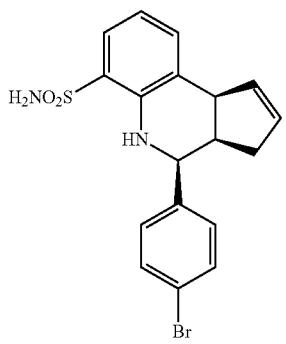 [SMILES: NS(=O)(=O)c1cccc2c1N[C@H](c1ccc(Br)cc1)[C@@H]1CC=C[C@H]21]

4-(4-bromophenyl)-3a,4,5,9b-tetrahydro-3H-cyclopenta[c]quinoline-6-sulfonamide (GAT120; 11)

$^1$H NMR (500 MHz, DMSO) δ 7.63 (dd, J=8.0 Hz, 1.5 Hz, 1H,), 7.50 (d, J=8.5 Hz, 2H, H-12,14), 7.29 (d, J=8.0 Hz, 2H, H-11,15), 7.24 (d, J=7.5 Hz, 1H), 6.79 (t, J=7.5 Hz, 1H,), 5.96 (s, 1H, H—NH), 5.86-5.78 (m, 1H, H-1), 5.69-5.62 (m, 1H, H-2), 4.87 (s, 2H, H—NH$_2$), 4.68 (d, J=3.5 Hz, 1H, H-4), 4.15 (d, J=8.5 Hz, 1H, H-9b), 3.00 (ddq, J=8.5 Hz, 3.5 Hz, 1.5 Hz, 1H, H-3a), 2.49 (qdd, J=17.5 Hz, 9.5 Hz, 2.5 Hz, 1H, H-3$_{eq}$), 1.84 (qdd, J=17.5 Hz, 8.5 Hz, 1.5 Hz, 1H, H-3$_{ax}$)

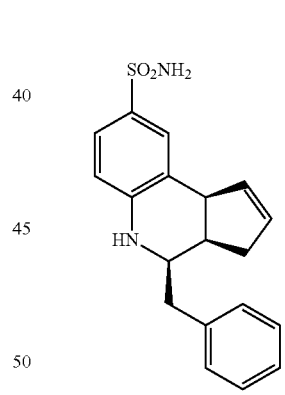

4-([1,1'-biphenyl]-4-yl)-3a,4,5,9b-tetrahydro-3H-cyclopenta[c]quinoline-8-sulfonamide (GAT122; 12)

$^1$H NMR (500 MHz, DMSO) δ 7.72-7.68 (m, 4H), 7.54 (d, J=8.0 Hz, 2H), 7.48 (t, J=8.0 Hz, 2H), 7.45 (d, J=2.0 Hz, 1H), 7.40-7.32 (m, 2H, esp. 7.35 (dd, J=8.5 Hz, 2.0 Hz, 1H)), 6.97 (s, 2H), 6.82 (d, J=8.5 Hz, 1H), 5.93-5.87 (m, 1H), 5.67-5.61 (m, 1H), 4.68 (d, J=2.5 Hz, 1H), 4.10 (d, J=9.0 Hz, 1H), 3.05-2.94 (dq as m, 1H), 2.44 (ddd, J=16.0 Hz, 9.5 Hz, 2.0 Hz, 1H), 1.72 (dd, J=15.0 Hz, 8.5 Hz, 1H)

4-benzyl-3a,4,5,9b-tetrahydro-3H-cyclopenta[c]quinoline-8-sulfonamide (GAT123; 13)

$^1$H NMR (500 MHz, DMSO) δ 7.36 (m, 6H), 7.24 (tt, J=8.0 Hz, 3.0 Hz, 1H), 6.92 (s, 2H), 6.68 (d, J=8.5 Hz, 1H), 5.94 (s, 1H), 5.85-5.80 (m, 1H), 5.71-5.66 (m, 1H), 3.82 (d, J=8.0 Hz, 1H), 3.65-3.58 (m, 1H), 2.96 (dd, J=13.0 Hz, 5.0 Hz, 1H), 2.61 (dd, J=13.0 Hz, 9.5 Hz, 1H), 2.51-2.38 (m, 2H), 2.33-2.25 (m, 1H)

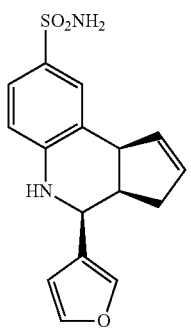 [SMILES: NS(=O)(=O)c1ccc2c(c1)[C@H]1C=CC[C@H]1[C@@H](c1ccoc1)N2]

4-(furan-3-yl)-3a,4,5,9b-tetrahydro-3H-cyclopenta[c]quinoline-8-sulfonamide (GAT124; 14)

$^1$H NMR (500 MHz, DMSO-d6) δ 7.69 (br s, 1H), 7.66 (dd as t, J=1.5 Hz, 1H), 7.42 (d, J=1.5 Hz, 1H), 7.32 (dd, J=8.5, 2.0 Hz, 1H), 6.95 (s, 2H), 6.77 (d, J=8.5 Hz, 1H), 6.59 (d, J=1.5 Hz, 1H), 6.20 (s, 1H), 5.88-5.82 (m, 1H), 5.67-5.63 (m, 1H), 4.51 (d, J=2.0 Hz, 1H), 4.04 (d, J=9.0 Hz, 1H), 2.99 (qd, J=8.5 Hz, 3.5 Hz, 1H), 2.38 (ddd, J=16.5 Hz, 9.5 Hz, 2.5 Hz, 1H), 1.98 (dd, J=16 Hz, 9.0 Hz, 1H)

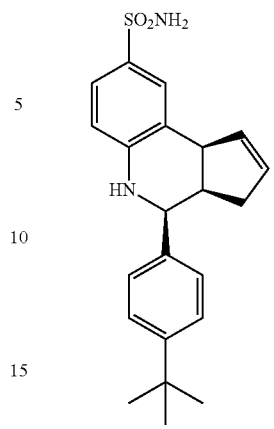

4-(4-(tert-butyl)phenyl)-3a,4,5,9b-tetrahydro-1H-cyclopenta[c]quinoline-8-sulfonamide (GAT 127; 16)

1H NMR (500 MHz, CDCl3) δ 7.59 (d, J=1.0 Hz, 1H), 7.51 (dd, J=8.5 Hz, 2.5 Hz, 1H), 7.41 (d, J=8.5 Hz, 2H), 7.33 (d, J=8.0 Hz, 2H), 6.63 (d, J=8.5 Hz, 1H), 5.92-5.86 (m, 1H), 5.72-5.66 (m, 1H), 4.69 (d, J=3.0 Hz, 1H), 4.64 (s, 2H), 4.22 (s, 1H), 4.11 (d, J=9.0 Hz, 1H), 3.00 (dq, J=9.0 Hz, 3.0 Hz, 1H), 2.59 (qdd, J=16.0 Hz, 9.5 Hz, 2.0 Hz, 1H), 1.88 (dddd, J=17.5 Hz, 9.5 Hz, 3.0 Hz, 1.5 Hz, 1H)

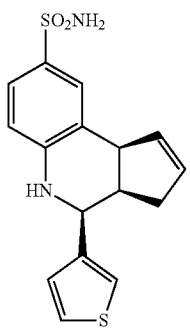 [SMILES: NS(=O)(=O)c1ccc2c(c1)[C@H]1C=CC[C@H]1[C@@H](c1ccsc1)N2]

4-(thiophen-3-yl)-3a,4,5,9b-tetrahydro-3H-cyclopenta[c]quinoline-8-sulfonamide (GAT125; 15)

$^1$H NMR (500 MHz, DMSO) δ 7.55 (dd, J=5.0 Hz, 3.0 Hz, 1H, H-13), 7.46 (d, J=5.5 Hz, 1H, H-11), 7.42 (d, J=2.0 Hz, 1H, H-9), 7.33 (dd, J=8.5 Hz, 2.0 Hz, 1H, H-7), 7.20 (dd, J=5.0 Hz, 1.0 Hz, 1H, H-12), 6.95 (s, 2H, H—NH2), 6.80 (d, J=9.0 Hz, 1H, H-6), 6.35 (s, 1H, H—NH), 5.90-5.82 (m, 1H, H-1), 5.66-5.60 (m, 1H, H-1), 4.69 (d, J=3.5 Hz, 1H, H-4), 4.05 (d, J=7.5 Hz, 1H, H-9b), 3.03 (qd, J=9.0 Hz, 1.5 Hz, 1H, H-3a), 2.37 (qdd, J=16.5 Hz, 10.0 Hz, 2.5 Hz, 1H, H-3$_{eq}$), 1.80 (dd, J=15.5 Hz, 8.5 Hz, 1H, H-3$_{ax}$)

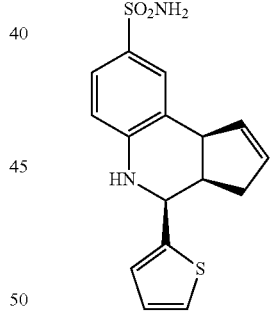

4-(thiophen-2-yl)-3a,4,5,9b-tetrahydro-3H-cyclopenta[c]quinoline-8-sulfonamide (GAT130; 17)

$^1$H NMR (500 MHz, DMSO) δ 7.47 (d, J=5.0 Hz, 1H, H-13), 7.43 (d, J=2.0 Hz, 1H, H-9), 7.33 (dd, J=8.5 Hz, 2.0 Hz, 1H, H-7), 7.16 (d, J=3.5 Hz, 1H, H-11), 7.04 (dd, J=5.0 Hz, 3.0 Hz, 1H, H-12), 6.97 (s, 2H, H—NH$_2$), 6.80 (d, J=8.5 Hz, 1H, H-6), 6.45 (s, 1H, H—NH), 5.93-5.85 (m, 1H, H-1), 5.70-5.63 (m, 1H, H-2), 4.92 (d, J=3.0 Hz, 1H, H-4), 4.07 (d, =8.5 Hz, 1H, H-9b), 3.00-2.89 (m, 1H, H-3a), 2.54-2.43 (m, 1H, H-3$_{eq}$), 1.95 (dd, J=15.5 Hz, 9.0 Hz, 1H, H-3$_{ax}$)

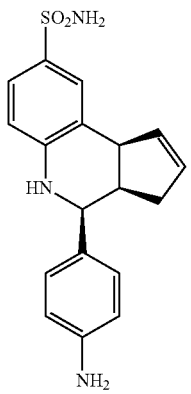

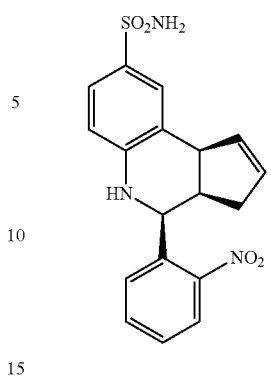

4-(4-aminophenyl)-3a,4,5,9b-tetrahydro-3H-cyclopenta[c]quinoline-8-sulfonamide (GAT133; 18)

$^1$H NMR (400 MHz, DMSO) δ 7.40 (s, 1H, H-9), 7.30 (d, J=8.8 Hz, 1H, H-7), 7.07 (d, J=8.0 Hz, 2H, H-12,14), 6.91 (s, 2H, H—NH2), 6.77 (d, J=8.0 Hz, 1H, H-6), 6.56 (d, J=8.0 Hz, 2H, H-11,15), 6.17 (s, 1H, H—NH), 5.91-5.82 (m, 1H, H-1), 5.66-5.58 (m, 1H, H-2), 4.96 (s, 2H, H-aryl NH$_2$), 4.44 (brs, 1H, H-4), 4.01 (d, J=8.0 Hz, 1H, H-9b), 2.89-2.78 (m, 1H, H-3a), 2.46-2.34 (m, 1H, H-3eq), 1.78-1.66 (m, 1H, H-3ax)

4-(2-nitrophenyl)-3a,4,5,9b-tetrahydro-3H-cyclopenta[c]quinoline-8-sulfonamide (GAT136; 20)

$^1$H NMR (500 MHz, DMSO-d6) δ 7.97 (m, 1H), 7.92 (m, 1H), 7.80 (m, 1H), 7.60 (m, 1H), 7.47 (s, 1H), 7.36 (m, 1H), 6.98 (s, 2H), 6.78 (d, 1H), 6.37 (s, 1H), 5.94 (m, 1H), 5.67 (m, 1H), 4.96 (m, 1H), 4.09 (m, 1H), 3.09 (m, 1H), 2.55 (m, 1H), 1.70 (m, 1H)

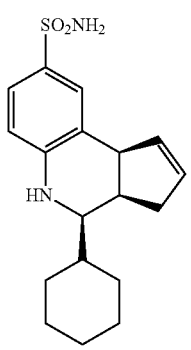 [SMILES: NS(=O)(=O)c1ccc2c(c1)[C@H]1C=CC[C@H]1[C@@H](C1CCCCC1)N2]

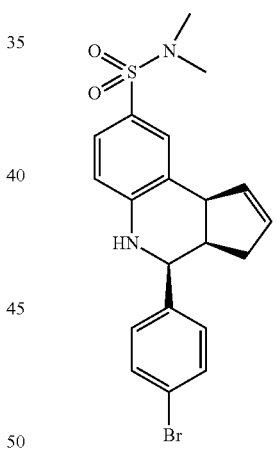

4-cyclohexyl-3a,4,5,9b-tetrahydro-3H-cyclopenta[c]quinoline-8-sulfonamide (GAT134; 19)

$^1$H NMR (500 MHz, DMSO-d6) δ 7.34 (d, J=2.0 Hz, 1H), 7.26 (dd, J=8.5 Hz, 2.0 Hz, 1H), 6.89 (s, 2H), 6.80 (d, J=9.0 Hz, 1H), 5.87-5.81 (m, 1H), 5.70-5.65 (m, 1H), 5.62 (s, 1H), 3.89 (d, J=9.0 Hz, 1H), 3.02 (dd, J=8.5 Hz, 2.0 Hz, 1H), 2.33-2.23 (m, 1H), 2.22-2.14 (m, 2H), 1.88-1.60 (m, 4H), 1.34-1.10 (m, 4H), 1.16-0.88 (m, 2H)

4-(4-bromophenyl)-N,N-dimethyl-3a,4,5,9b-tetrahydro-3H-cyclopenta[c]quinoline-8-sulfonamide (GAT138/GAT1300; 21)

$^1$H NMR (500 MHz, DMSO) δ 7.60 (d, J=8.0 Hz, 2H), 7.41 (d, J=8.0 Hz, 2H), 7.33 (d, J=2.0 Hz, 1H), 7.25 (dd, J=8.5, 2.5 Hz, 1H), 6.87 (d, J=8.5 Hz, 1H), 6.60 (s, 1H), 5.98-5.89 (m, 1H), 5.65-5.56 (m, 1H), 4.67 (d, J=3.5 Hz, 1H), 4.10 (d, J=8.5 Hz, 1H), 3.00-2.95 (m, 1H), 2.52 (s, 6H), 2.38-2.28 (m, 1H), 1.64 (dd, J=16.0 Hz, 8.5 Hz, 1H)

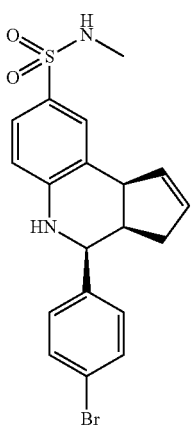 [SMILES: CNS(=O)(=O)c1ccc2c(c1)[C@H]1C=CC[C@H]1[C@@H](c1ccc(Br)cc1)N2]

4-(4-bromophenyl)-N-methyl-3a,4,5,9b-tetrahydro-3H-cyclopenta[c]quinoline-8-sulfonamide (GAT139/ GATGAT1301; 22)

1H NMR (500 MHz, DMSO) δ 7.59 (d, J=8.0 Hz, 2H, H-12,14), 7.41 (d, J=8.5 Hz, 2H, H-11,15), 7.37 (d, J=2.0 Hz, 1H, H-9), 7.29 (d, J=8.5 Hz, 2.0 Hz, 1H, H-7), 7.00 (q, J=4.5 Hz, 1H, H—NH), 6.83 (d, J=8.5 Hz, 1H, H-6), 6.48 (s, 1H, H—NH), 5.93-5.87 (m, 1H, H-1), 5.66-5.58 (m, 1H, H-2), 4.65 (d, J=3.0 Hz, 1H, H-4), 4.08 (d, J=8.5 Hz, 1H, H-9b), 2.94 (ddq, J=9.5 Hz, 3.5 Hz, 1.5 Hz, 1H, H-3a), 2.38-2.28 (m, 1H, H-3eq), 1.64 (dd, J=14.5 Hz, 8.0 Hz, 1H, H-3ax)

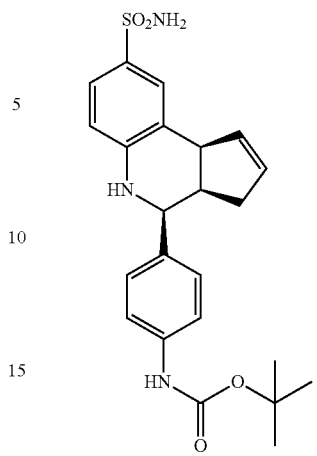

tert-butyl-(4-43aR,4S,9bS)-8-sulfamoyl-3a,4,5,9b-tetrahydro-3H-cyclopenta[c]quinolin-4-yl)phenyl) carbamate (GAT141; 24)

¹H NMR (500 MHz, CDCl₃) δ 7.59 (d, J=1.5 Hz, 1H) 7.50 (dd, J=8 Hz, 1.5 Hz, 1H), 7.39 (d, J=8 Hz, 2H), 7.13 (d, J=8 Hz, 2H), 6.63 (d, J=8.5 Hz, 1H) 5.90-5.85 (m, 1H), 5.67 (d, J=4 Hz, 1H), 5.03 (s, 1H), 4.78 (s, 2H), 4.68 (d, J=3 Hz, 1H), 4.23 (s, 1H), 4.09 (br d, J=8.5 Hz, 1H) 2.98 (qd, J=17.5 Hz, 8.5 Hz, 2 Hz, 1H), 2.58-2.50 (m, 1H), 1.85 (dd, J=15 Hz, 7 Hz, 1.5 Hz, 1H), 1.40 (s, 9H)

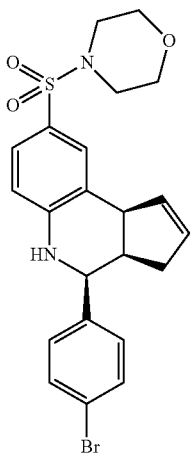 [SMILES: O=S(=O)(c1ccc2c(c1)[C@H]1C=CC[C@H]1[C@@H](c1ccc(Br)cc1)N2)N1CCOCC1]

4-((4-(4-bromophenyl)-3a,4,5,9b-tetrahydro-3H-cyclopenta[c]quinolin-8-yl)sulfonyl)morpholine (GAT140/GAT1302; 23)

1H NMR (500 MHz, DMSO) δ 7.60 (d, J=8.0 Hz, 2H), 7.41 (d, J=8.5 Hz, 2H), 7.24 (dd, J=8.0 Hz, 1.5 Hz, 1H), 6.88 (d, J=8.5 Hz, 1H), 6.65 (s, 1H), 5.97-5.90 (m, 1H), 5.65-5.58 (m, 1H), 4.68 (d, J=3.5 Hz, 1H), 4.11 (d, J=9.5 Hz, 1H), 3.62 (t, J=3.5 Hz, 4H), 3.00-2.90 (m, 1H), 2.86-2.78 (m, 4H), 2.39-2.29 (m, 1H), 1.70-1.60 (m, 1H)

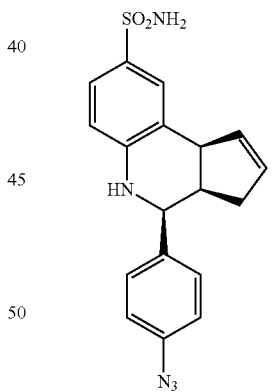

4-(4-azidophenyl)-3a,4,5,9b-tetrahydro-3H-cyclopenta[c]quinoline-8-sulfonamide (GAT143; 25)

¹H NMR (500 MHz, DMSO) δ 7.49 (d, J=8.5 Hz, 2H, H-12,14), 7.43 (d, J=2.0 Hz, 1H, H-9), 7.33 (dd, J=8.0 Hz, 2.0 Hz, 1H, H-7), 7.15 (d, J=8.5 Hz, 2H, H-11, 15), 6.94 (s, 2H, H—NH₂), 6.80 (d, J=8.5 Hz, 1H, H-6), 6.36 (s, 1H, H—NH), 5.92-5.86 (m, 1H, H-1), 5.65-5.59 (m, 1H, H-2), 4.64 (d, J=3.5 Hz, 1H, H-4), 4.06 (d, J=9.0 Hz, 1H, H-9b), 2.98-2.88 (m, 1H, H-3a), 2.35 (ddq, J=16.5 Hz, 9.5 Hz, 2.0 Hz, 1H, H-3$_{eq}$), 1.64 (dd, J=15 Hz, 9.5 Hz, 1H, H-3$_{ax}$)

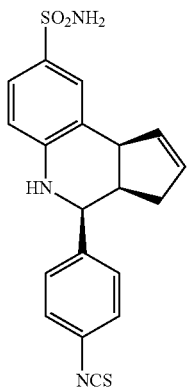

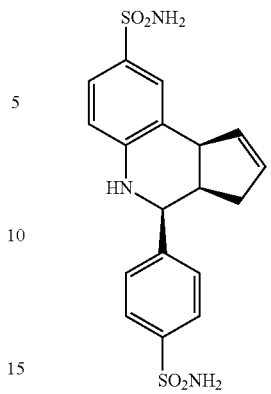

4-(4-isothiocyanatophenyl)-3a,4,5,9b-tetrahydro-3H-cyclopenta[c]quinoline-8-sulfonamide (GAT144; 26)

¹H NMR (500 MHz, CDCl₃) δ 7.52 (d, J=9 Hz, 2H), 7.43 (d, J=2.0 Hz, 1H), 7.34 (dd, J=8 Hz, 2 Hz, 1H), 6.96 (s, 2H), 6.80 (d, J=8.5 Hz, 1H), 6.42 (s, 1H), 5.87-5.91 (m, 1H), 5.59-5.64 (m, 1H), 4.67 (d, J=3.5 Hz, 1H), 4.06 (d, J=8.5 Hz, 1H), 2.98-2.90 (m, 1H), 2.32 (ddd, J=18, 12, 2 Hz, 1H), 1.62 (dd, J=15.5, 9 Hz, 1H).

4-(4-sulfamoylphenyl)-3a,4,5,9b-tetrahydro-3H-cyclopenta[c]quinoline-8-sulfonamide (GAT146; 28)

¹H NMR (500 MHz, DMSO) δ 7.84 (d, J=8.5 Hz, 2H), 7.63 (d, J=8.5 Hz, 2H), 7.45 (d, J=2.0 Hz, 1H), 7.36 (s, 2H), 7.35 (dd, J=8.5 Hz, 2.0 Hz, 1H), 6.97 (s, 2H), 6.81 (d, J=9.0 Hz, 1H), 6.44 (s, 1H), 5.94-5.86 (m, 1H), 5.66-5.58 (m, 1H), 4.72 (d, J=3.5 Hz, 1H), 4.09 (d, J=9.0 Hz, 1H), 3.04-2.92 (m, 1H), 2.37 (ddd, J=16.5 Hz, 10.0 Hz, 2.0 Hz, 1H), 1.62 (dd, J=15.5 Hz, 8.5 Hz, 1H)

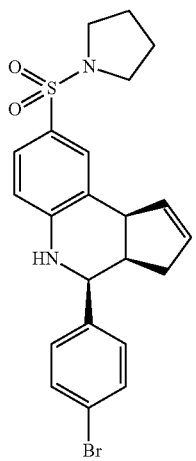 [SMILES: O=S(=O)(c1ccc2c(c1)[C@H]1C=CC[C@H]1[C@@H](c1ccc(Br)cc1)N2)N1CCCC1]

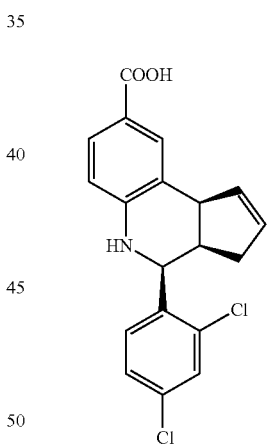

4-(4-bromophenyl)-8-(pyrrolidin-1-ylsulfonyl)-3a,4,5,9b-tetrahydro-3H-cyclopenta[c]quinolone (GAT145/GAT1304; 27)

¹H NMR (500 MHz, DMSO-d6) δ 7.59 (d, J=8.5 Hz, 2H), 7.41 (d, J=8.5 Hz, 2H), 7.39 (d, J=1.5 Hz, 1H), 7.31 (dd, J=8.5 Hz, 2.0 Hz, 1H), 6.85 (d, J=8.5 Hz, 1H), 6.56 (s, 1H), 5.96-5.89 (m, 1H), 5.60 (d, J=5.0 Hz, 1H), 4.65 (d, J=3.0 Hz, 1H), 4.10 (d, J=8.5 Hz, 1H), 3.12-3.00 (m, 4H), 2.95 (q, J=9.0 Hz, 1H), 2.38-229 (m, 1H), 1.69-1.58 (m, 5H)

4-(2,4-dichlorophenyl)-3a,4,5,9b-tetrahydro-3H-cyclopenta[c]quinoline-8-carboxylic acid (GAT147; 29)

¹H NMR (500 MHz, DMSO-d6) δ 12.21 (s, 1H), 7.66 (s, 1H), 7.65 (d, J=10.0 Hz, 1H), 7.52 (td, J=8.0 Hz, 2.0 Hz, 2H), 6.75 (d, J=8.5 Hz, 2.0 Hz, 1H), 6.39 (s, 1H), 5.98-5.90 (m, 1H), 5.64-5.56 (m, 1H), 4.89 (d, J=2.5 Hz, 1H), 4.08 (d, J=8.5 Hz, 1H), 3.06 (qdd, J=8.5 Hz, 3.5 Hz, 1.5 Hz, 1H), 2.36 (ddd, J=15.5 Hz, 10.0 Hz, 2.0 Hz, 1H), 1.61 (dd, J=15.0 Hz, 9.0 Hz, 1H)

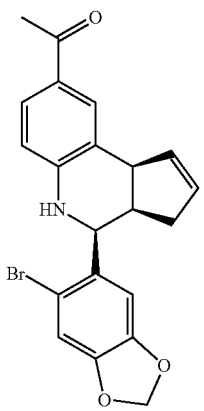 [SMILES: CC(=O)c1ccc2c(c1)[C@H]1C=CC[C@H]1[C@@H](c1cc3c(cc1Br)OCO3)N2]

1-((4-(6-bromobenzo[d][1,3]dioxol-5-yl)-3a,4,5,9b-tetrahydro-3H-cyclopenta[c]quinolin-8-yl)ethan-1-one (GAT148; 29)

1H NMR (400 MHz, CDCl3) 7.70 (d, J=1.6 Hz, 1H), 7.61 (dd, J=8.3 Hz, 1.6 Hz, 1H) 7.09 (s, 1H), 7.03 (s, 1H), 6.61 (d, J=8.3 Hz, 1H), 6.00 (d, J=1.3 Hz, 1H), 5.99 (d, J=1.3 Hz, 1H), 5.96-5.92 (m, 1H), 5.68-5.66 (m, 1H), 4.98 (d, J=3.1 Hz, 1H), 4.12 (d, J=8.3 Hz, 1H), 4.02 (br s, 1H), 3.23-3.15 (m, 1H), 2.57-2.46 (m, 4H), 1.86-1.77 (m, 1H)

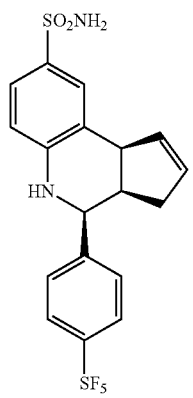

4-(4-(pentafluoro-λ⁶-sulfanyl)phenyl)-3a,4,5,9b-tetrahydro-3H-cyclopenta[c]quinoline-8-sulfonamide (GAT149; 30)

¹H NMR (500 MHz, DMSO) δ 7.94 (d, J=8.5 Hz, 2H, H-12,14), 7.69 (d, J=9.0 Hz, 2H, H-11,15), 7.46 (d, J=1.5 Hz, 1H, H-9), 7.36 (dd, J=8.5 Hz, 2.0 Hz, 1H, H-7), 6.99 (s, 2H, H—NH₂), 6.81 (d, J=8.5 Hz, 1H, H-6), 6.47 (s, 1H, H—NH), 5.94-5.88 (m, 1H, H-1), 5.64-5.58 (m, 1H), 4.75 (d, J=3.5 Hz, 1H, H-4), 4.10 (d, J=9.0 Hz, 1H, H-9b), 3.04-2.94 (m, 1H, H-3a), 2.53 (qdd, J=16.0 Hz, 9.0 Hz, 2.0 Hz, 1H, H-3$_{eq}$), 1.64 (dd, J=15.0 Hz, 8.5 Hz, 1H, H-3$_{ax}$)

3a,4,5,9b-tetrahydro-3H-cyclopenta[c]quinoline-8-sulfonamide (GAT151; 33)

¹H NMR (500 MHz, DMSO-d6) δ 7.51 (d, J=1.5 Hz, 1H), 7.32 (dd, J=8.5 Hz, 2.0 Hz, 1H), 6.91 (s, 2H), 6.61 (d, J=8.5 Hz, 1H), 6.31 (d, J=1.5 Hz, 1H), 5.82-5.76 (m, 1H), 5.74-5.68 (m, 1H), 3.82 (s, 1H), 3.12-3.02 (m, 1H), 2.70-2.54 (m, 3H), 2.09 (dd, J=9.0 Hz, 2.0 Hz, 1H)

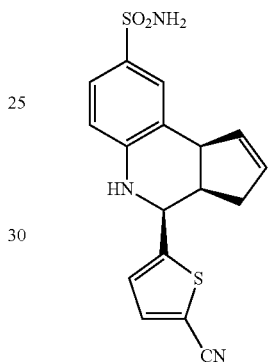

4-(5-cyanothiophen-2-yl)-3a,4,5,9b-tetrahydro-3H-cyclopenta[c]quinoline-8-sulfonamide (GAT152; 34)

¹H NMR (500 MHz, DMSO) δ 7.92 (d, J=3.5 Hz, 1H, H-12), 7.46 (d, J=2.0 Hz, 1H, H-9), 7.37 (dd, J=8.5 Hz, 2.0 Hz, 1H, H-7), 7.33 (d, J=4.0 Hz, 1H, H-11), 7.01 (s, 2H, H—NH₂), 6.80 (d, J=8.5 Hz, 1H, H-6), 6.65 (s, 1H, H—NH), 5.96-5.88 (m, 1H, H-1), 5.69-5.62 (m, 1H, H-2), 5.03 (d, J=3.5 Hz, 1H, H-4), 4.07 (d, J=8.5 Hz, 1H, H-9b), 2.99 (ddq, J=8.5 Hz, 3.0 Hz, 1.0 Hz, 1H, H-3a), 2.40 (qdd, J=16.0 Hz, 9.0 Hz, 2.0 Hz, 1H, H-3$_{eq}$), 1.90 (tdd, J=16.0 Hz, 8.5 Hz, 2.0 Hz, 1H, H-3$_{ax}$)

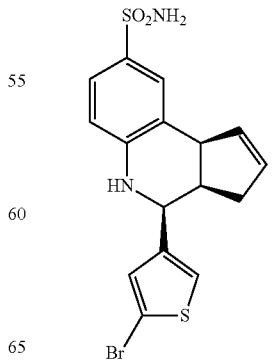

4-(5-bromothiophen-3-yl)-3a,4,5,9b-tetrahydro-3H-cyclopenta[c]quinoline-8-sulfonamide (GAT153; 35)

$^1$H NMR (500 MHz, DMSO) δ 7.48 (s, 1H, H-12), 7.42 (d, J=2.0 Hz, 1H, H-9), 7.33 (dd, J=8.5 Hz, 2.5 Hz, 1H, H-7), 7.30 (d, J=1.5 Hz, 1H, H-11), 6.96 (s, 2H, H—NH$_2$), 6.79 (d, J=8.5 Hz, 1H, H-6), 6.35 (s, 1H, H—NH), 5.88-5.83 (m, 1H, H-1), 5.66-5.60 (m, 1H, H-2), 4.62 (d, J=3.5 Hz, 1H, H-4), 4.04 (d, J=3.5 Hz, 1H, H-9b), 3.02 (dq, J=9 Hz, 3.5 Hz, 1H, H-3a), 2.35 (qdd, J=16 Hz, 9.5 Hz, 2.0 Hz, 1H, H-3$_{eq}$), 1.84 (dd, J=15.5 Hz, 8.5 Hz, 1H, H-3$_{ax}$)

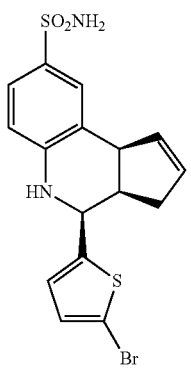 [SMILES: NS(=O)(=O)c1ccc2c(c1)[C@H]1C=CC[C@H]1[C@@H](c1ccc(Br)s1)N2]

4-(5-bromothiophen-2-yl)-3a,4,5,9b-tetrahydro-3H-cyclopenta[c]quinoline-8-sulfonamide (GAT154; 36)

$^1$H NMR (500 MHz, DMSO) δ 7.43 (d, J=2 Hz, 1H, H-9), 7.34 (dd, J=8 Hz, 2 Hz, 1H, H-7), 7.14 (d, J=3.5 Hz, 1H, H-12), 7.00 (d, J=4.0 Hz, 1H, H-11), 6.97 (s, 2H, H—NH$_2$), 6.78 (d, J=8.5 Hz, 1H, H-6), 6.49 (s, 1H, H—NH), 5.92-5.87 (m, 1H, H-1), 5.69-5.64 (m, 1H, H-2), 4.88 (d, J=3.0 Hz, 1H, H-4), 4.05 (d, J=8.5 Hz, 1H, H-9b), 2.93 (dq, J=9.0 Hz, 2.0 Hz, 1H, H-3a), 2.44 (qdd, J=16.0 Hz, 9.0 Hz, 2.0 Hz, 1H, H-3$_{eq}$), 2.00 (dd, J=16.5 Hz, 9.0 Hz, 1H, H-3$_{ax}$)

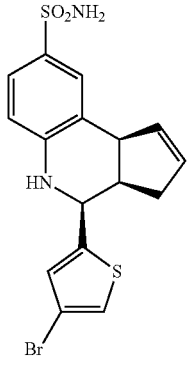 [SMILES: NS(=O)(=O)c1ccc2c(c1)[C@H]1C=CC[C@H]1[C@@H](c1cc(Br)cs1)N2]

4-(4-bromothiophen-2-yl)-3a,4,5,9b-tetrahydro-3H-cyclopenta[c]quinoline-8-sulfonamide (GAT155; 37)

$^1$H NMR (500 MHz, CDCl$_3$) δ 7.59 (d, J=2.0 Hz, 1H), 7.53 (dd, J=8.5 Hz, 2.0 Hz, 1H), 6.96 (d, J=3.5 Hz, 1H), 6.84 (d, J=4.5 Hz, 1H), 6.65 (d, J=8.0 Hz, 1H), 5.91-5.85 (m, 1H), 5.76-5.70 (m, 1H), 4.90 (d, J=3.0 Hz, 1H), 4.66 (s, 1H), 4.24 (s, 1H), 4.09 (d, J=8.5 Hz, 1H), 3.02 (dq, J=9.0 Hz, 3.5 Hz, 1H), 2.63 (ddd, J=16.0 Hz, 9.5 Hz, 2.0 Hz, 1H), 2.16 (dd, J=16.0 Hz, 8.0 Hz, 1H)

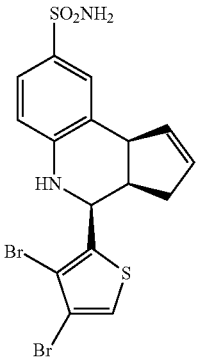 [SMILES: NS(=O)(=O)c1ccc2c(c1)[C@H]1C=CC[C@H]1[C@@H](c1scc(Br)c1Br)N2]

4-(3,4-dibromothiophen-2-yl)-3a,4,5,9b-tetrahydro-3H-cyclopenta[c]quinoline-8-sulfonamide (GAT156; 38)

$^1$H NMR (500 MHz, DMSO) δ 7.91 (s, 1H, H-11), 7.47 (d, J=2.0 Hz, 1H, H-9), 7.37 (dd, J=8.0 Hz, 1.5 Hz, 1H), 7.01 (s, 2H, H—NH$_2$), 6.79 (d, J=8.5 Hz, 1H, H-6), 6.57 (s, 1H, H—NH), 5.97-5.91 (m, 1H, H-1), 5.70-5.64 (m, 1H, H-2), 4.94 (d, J=3.5 Hz, 1H, H-4), 4.10 (d, J=9.0 Hz, 1H, H-9b), 3.05 (ddq, J=8.5 Hz, 3.0 Hz, 1.5 Hz, 1H, H-3a), 2.51-2.41 (m, 1H, H-3$_{eq}$), 1.89 (dd, J=15.0 Hz, 8.5 Hz, 1H, H-3$_{ax}$)

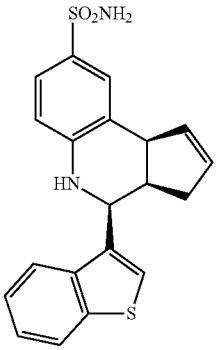 [SMILES: NS(=O)(=O)c1ccc2c(c1)[C@H]1C=CC[C@H]1[C@@H](c1csc3ccccc13)N2]

4-(benzo[b]thiophen-3-yl)-3a,4,5,9b-tetrahydro-3H-cyclopenta[c]quinoline-8-sulfonamide (GAT157; 36)

$^1$H NMR (500 MHz, DMSO) δ 8.02 (t, J=7.5 Hz, 1H,), 8.02 (t, J=5.5 Hz, 1H,), 7.68 (s, 1H, H-11), 7.48 (d, J=2.0 Hz, 1H, H-9), 7.46-7.38 (m, 2H,), 7.36 (dd, J=9.0 Hz, 1.0 Hz, 1H, H-7), 6.99 (s, 2H, H—NH$_2$), 6.85 (d, J=9.0 Hz, 1H, H-6), 6.42 (s, 1H, H—NH), 5.90-5.84 (m, 1H, H-1), 5.64-5.58 (m, 1H, H-2), 5.06 (d, J=3.0 Hz, 1H, H-4), 4.18 (d, J=8.5 Hz, 1H, H-9b), 3.19 (ddq, J=8.5 Hz, 3.0 Hz, 1.5 Hz, 1H, H-3a), 2.45 (qdd, J=17.0 Hz, 10.0 Hz, 2.5 Hz, 1H, H-3$_{eq}$), 1.62 (tdd, J=15.5 Hz, 9.0 Hz, 2.5 Hz, 1H, H-3$_{ax}$)

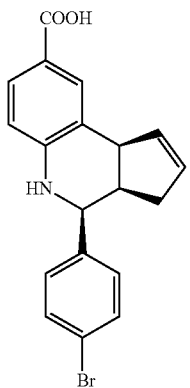 [SMILES: O=C(O)c1ccc2c(c1)[C@H]1C=CC[C@H]1[C@@H](c1ccc(Br)cc1)N2]

4-(4-bromophenyl)-3a,4,5,9b-tetrahydro-3H-cyclopenta[c]quinoline-8-carboxylic acid (GAT158; 40)

$^1$H NMR (500 MHz, DMSO) δ 12.14 (s, 1H), 7.61-7.55 (m, 3H esp. 7.58 (d, J=8.5 Hz, 2H)), 7.49 (dd, J=8.5 Hz, 2.0 Hz, 1H), 7.41 (d, J=9.0 Hz, 1H), 6.75 (d, J=8.5 Hz, 1H), 6.42 (s, 1H), 5.95-5.88 (m, 1H), 5.62-5.55 (m, 1H), 4.63 (d, J=3.5 Hz, 1H), 4.06 (d, J=9.0 Hz, 1H), 2.97-2.86 (dq as m, 1H), 2.33 (ddd, J=16.0 Hz, 10.0 Hz, 2.0 Hz, 1H), 1.63 (dd, J=15.5 Hz, 8.0 Hz, 1H)

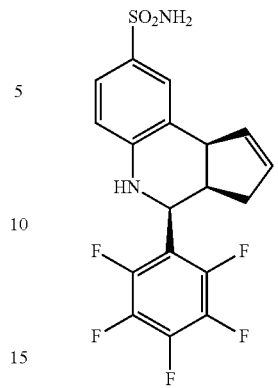

4-(perfluorophenyl)-3a,4,5,9b-tetrahydro-3H-cyclopenta[c]quinoline-8-sulfonamide (GAT160; 42)

$^1$H NMR (500 MHz, DMSO) δ 8.01 (d, J=2.0 Hz, 1H, H-9), 7.90 (dd, J=8.0 Hz, 2.0 Hz, 1H, H-7), 7.22 (d, J=9.0 Hz, 1H, H-6), 6.68 (s, 2H, H—NH$_2$), 6.41-6.36 (m, 1H, H-1), 6.36 (s, 1H, H—NH), 6.17-6.12 (m, 1H, H-2), 5.65 (d, J=3.5 Hz, 1H, H-4), 4.62 (d, J=9.0 Hz, 1H, H-9b), 3.55 (ddq, J=8.5 Hz, 3.5 Hz, 2.0 Hz, 1H, H-3a), 3.23-3.14 (m, 1H, H-3$_{eq}$), 2.62 (tdd, J=15.0, 8.0 Hz, 2.5 Hz, 1H, H-3$_{ax}$)

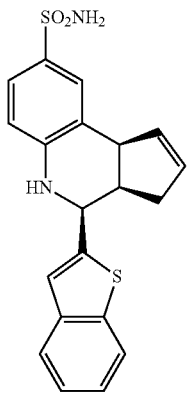 [SMILES: NS(=O)(=O)c1ccc2c(c1)[C@H]1C=CC[C@H]1[C@@H](c1cc3ccccc3s1)N2]

4-(benzo[b]thiophen-2-yl)-3a,4,5,9b-tetrahydro-3H-cyclopenta[c]quinoline-8-sulfonamide (GAT159; 38)

$^1$H NMR (500 MHz, DMSO) δ 7.96 (d, J=8.0 Hz, 2H), 7.82 (d, J=9.0 Hz, 2H), 7.48 (s, 1H), 7.42-7.30 (m, 3H), 6.99 (s, 2H), 6.84 (d, J=8.5 Hz, 1H), 6.60 (s, 1H), 5.95-5.87 (m, 1H), 5.70-5.62 (m, 1H), 4.99 (d, J=3.0 Hz, 1H), 4.12 (d, J=8.5 Hz, 1H), 3.05 (dq, J=8.5 Hz, 2.0 Hz, 1H), 2.56-2.44 (m, 1H), 1.98 (dd, J=15.5 Hz, 8.5 Hz, 1H)

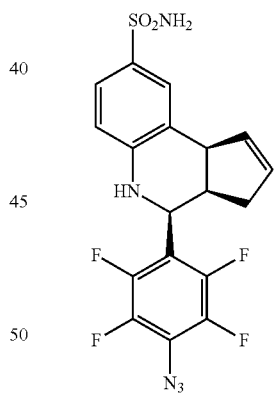

(3aR,4S,9bS)-4-(4-azido-2,3,5,6-tetrafluorophenyl)-3a,4,5,9b-tetrahydro-3H-cyclopenta[c]quinoline-8-sulfonamide (GAT161; 43)

$^1$H NMR (500 MHz, DMSO) δ 7.45 (d, J=2.0 Hz, 1H, H-9), 7.35 (dd, J=8.5 Hz, 2.0 Hz, 1H, H-7), 6.97 (s, 2H, H—NH$_2$), 6.69 (d, J=8.0 Hz, 1H, H-6), 6.65 (s, 1H, H—NH), 2.95 (dq, J=8.5 Hz, 2.5 Hz, 1H, H-3a), 2.60-2.50 (m, 1H, H-3$_{eq}$), 2.08 (dd, J=15.5 Hz, 7.5 Hz, 1H, H-3$_{ax}$)

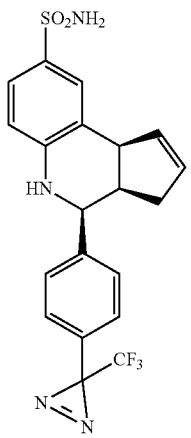 [SMILES: NS(=O)(=O)c1ccc2c(c1)[C@H]1C=CC[C@H]1[C@@H](c1ccc(C3(C(F)(F)F)N=N3)cc1)N2]

(3aR,4S,9bS)-4-(4-(3-(trifluoromethyl)-3H-diazirin-3-yl)phenyl)-3a,4,5,9b-tetrahydro-3H-cyclopenta[c]quinoline-8-sulfonamide (GAT162; 44)

¹H NMR (400 MHz, CDCl₃) δ 7.60 (s, 1H, H-9), 7.52 (d, J=8.8 Hz, 1H, H-7), 7.45 (d, J=8.0 Hz, 2H, H-12, 14), 7.22 (d, J=8.0 Hz, 2H, H-11, 15), 6.66 (d, J=8.0 Hz, 1H, H-6), 5.94-5.84 (m, 1H, H-1), 5.71-5.62 (m, 1H, H-2), 4.76 (s, 2H, H—NH₂), 4.72 (d, J=2.5 Hz, 1H, H-4), 4.18 (s, 1H, H—NH), 4.12 (d, J=7.2 Hz, 1H, H-9b), 2.99 (dq, J=8.8 Hz, 2.8 Hz, 1H, H-3a), 2.56-2.42 (m, 1H, H-3$_{eq}$), 1.78 (dd, J=16.8 Hz, 8.0 Hz, 1H, H-3$_{ax}$)

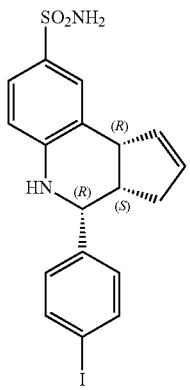

(3aS,4R,9bR)-4-(4-iodophenyl)-3a,4,5,9b-tetrahydro-3H-cyclopenta[c]quinoline-8-sulfonamide (GAT163; 45)

¹H NMR (500 MHz, DMSO) δ7.75 (d, J=8.5 Hz, 2H), 7.43 (d, J=2.0 Hz, 1H), 7.34 (dd, J=8.5 Hz, 2 Hz, 1H), 7.26 (d, J=8.5 Hz, 2H), 6.96 (s, 2H), 6.79 (d, J=8.5 Hz, 1H), 6.37 (s, 1H), 5.86-5.91 (m, 1H), 5.59-5.64 (m, 1H), 4.6 (d, J=3 Hz, 1H), 4.06 (d, J=9.5 Hz, 1H), 2.97-2.88 (m, 1H), 2.33 (ddd, J=16, 10, 2 Hz, 1H), 1.68-1.59 (m, 1H)

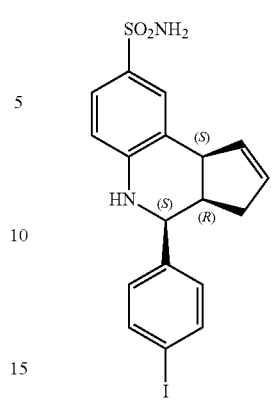

(3aR,4S,9bS)-4-(4-iodophenyl)-3a,4,5,9b-tetrahydro-3H-cyclopenta[c]quinoline-8-sulfonamide (GAT164; 46)

¹H NMR (500 MHz, DMSO) δ7.75 (d, J=8.5 Hz, 2H), 7.43 (d, J=2.0 Hz, 1H), 7.34 (dd, J=8.5 Hz, 2 Hz, 1H), 7.26 (d, J=8.5 Hz, 2H), 6.96 (s, 2H), 6.79 (d, J=8.5 Hz, 1H), 6.37 (s, 1H), 5.86-5.91 (m, 1H), 5.59-5.64 (m, 1H), 4.6 (d, J=3 Hz, 1H), 4.06 (d, J=9.5 Hz, 1H), 2.97-2.88 (m, 1H), 2.33 (ddd, J=16, 10, 2 Hz, 1H), 1.68-1.59 (m, 1H)

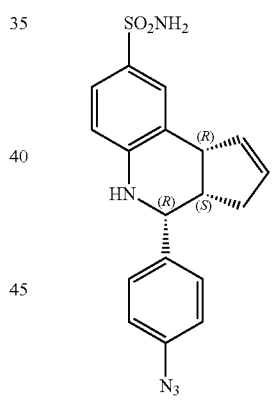

(3aS,4R,9bR)-4-(4-azidophenyl)-3a,4,5,9b-tetrahydro-3H-cyclopenta[c]quinoline-8-sulfonamide (GAT165; 47)

¹H NMR (500 MHz, DMSO) δ 7.49 (d, J=8.5 Hz, 2H, H-12,14), 7.43 (d, J=2.0 Hz, 1H, H-9), 7.33 (dd, J=8.0 Hz, 2.0 Hz, 1H, H-7), 7.15 (d, J=8.5 Hz, 2H, H-11, 15), 6.94 (s, 2H, H—NH₂), 6.80 (d, J=8.5 Hz, 1H, H-6), 6.36 (s, 1H, H—NH), 5.92-5.86 (m, 1H, H-1), 5.65-5.59 (m, 1H, H-2), 4.64 (d, J=3.5 Hz, 1H, H-4), 4.06 (d, J=9.0 Hz, 1H, H-9b), 2.98-2.88 (m, 1H, H-3a), 2.35 (ddq, J=16.5 Hz, 9.5 Hz, 2.0 Hz, 1H, H-3$_{eq}$), 1.64 (dd, J=15 Hz, 9.5 Hz, 1H, H-3$_{ax}$)

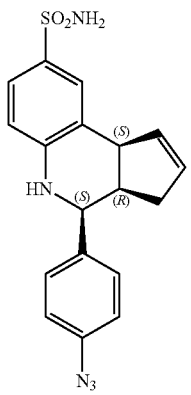

(3aR,4S,9bS)-4-(4-azidophenyl)-3a,4,5,9b-tetrahydro-3H-cyclopenta[c]quinoline-8-sulfonamide (GAT166; 48)

¹H NMR (500 MHz, DMSO) δ 7.49 (d, J=8.5 Hz, 2H, H-12,14), 7.43 (d, J=2.0 Hz, 1H, H-9), 7.33 (dd, J=8.0 Hz, 2.0 Hz, 1H, H-7), 7.15 (d, J=8.5 Hz, 2H, H-11, 15), 6.94 (s, 2H, H—NH$_2$), 6.80 (d, J=8.5 Hz, 1H, H-6), 6.36 (s, 1H, H—NH), 5.92-5.86 (m, 1H, H-1), 5.65-5.59 (m, 1H, H-2), 4.64 (d, J=3.5 Hz, 1H, H-4), 4.06 (d, J=9.0 Hz, 1H, H-9b), 2.98-2.88 (m, 1H, H-3a), 2.35 (ddq, J=16.5 Hz, 9.5 Hz, 2.0 Hz, 1H, H-3$_{eq}$), 1.64 (dd, J=15 Hz, 9.5 Hz, 1H, H-3$_{ax}$)

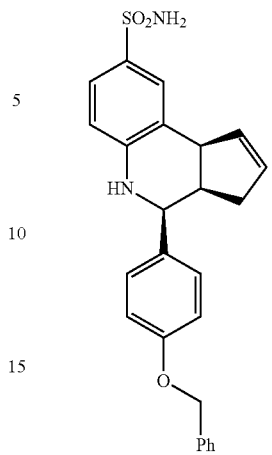

(3aR,4S,9bS)-4-(4-(benzyloxy)phenyl)-3a,4,5,9b-tetrahydro-3H-cyclopenta[c]quinoline-8-sulfonamide (GAT168; 50)

¹H NMR (500 MHz, CDCl$_3$) δ 7.59 (d, J=2.0 Hz, 1H), 7.51 (dd, J=8.0 Hz, 2.0 Hz, 1H), 7.48-7.37 (m, 4H), 7.37-7.28 (m, 3H), 7.00 (d, J=8.5 Hz, 1H), 5.92-5.86 (m, 1H), 5.72-5.66 (m, 1H), 5.09 (s, 2H), 4.66 (d, J=3.0 Hz, 1H), 4.63 (s, 2H), 4.18 (s, 1H), 4.10 (d, J=8.0 Hz, 1H), 2.99 (qdd, J=8.0 Hz, 4.0 Hz, 2.0 Hz, 1H), 2.56 (ddq, J=16.0 Hz, 9.5 Hz, 2.0 Hz, 1H), 1.87 (dddd, J=16.5 Hz, 8.5 Hz, 2.5 Hz, 1.5 Hz, 1H)

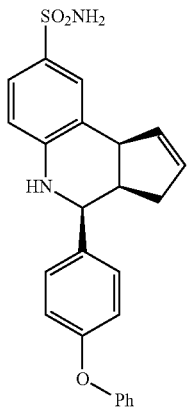 [SMILES: NS(=O)(=O)c1ccc2c(c1)[C@H]1C=CC[C@H]1[C@@H](c1ccc(Oc3ccccc3)cc1)N2]

4-(4-phenoxyphenyl)-3a,4,5,9b-tetrahydro-3H-cyclopenta[c]quinoline-8-sulfonamide (GAT167; 49)

¹H NMR (500 MHz, DMSO-d) δ 7.46 (d, J=8.5 Hz, 2H), 7.43 (d, J=1.5 Hz, 1H), 7.43-7.37 (m, 3H), 7.33 (dd, J=8.5 Hz, 2.0 Hz, 1H), 7.14 (t, J=7.0 Hz, 1H), 7.04 (d, J=8.5 Hz, 2H), 7.00 (d, J=8.5 Hz, 2H), 6.96 (s, 2H), 6.80 (d, J=8.5 Hz, 1H), 6.38 (s, 1H), 5.94-5.86 (m, 1H), 5.64 (d, J=5.5 Hz, 1H), 4.64 (d, J=3.5 Hz, 1H), 4.07 (d, J=8.5 Hz, 1H), 3.02-2.87 (m, 1H), 2.46-2.33 (m, 1H), 1.70 (dd, J=16.0 Hz, 9.0 Hz, 1H)

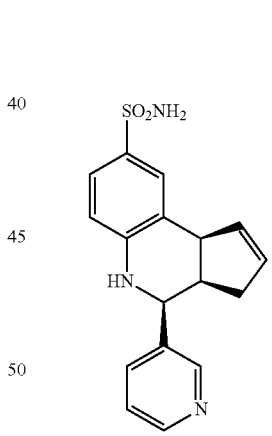

4-(pyridin-3-yl)-3a,4,5,9b-tetrahydro-3H-cyclopenta[c]quinoline-8-sulfonamide (GAT169; 51)

1H NMR (500 MHz, DMSO-d6) δ 8.10 (d, J=1.5 Hz, 1H), 7.75 (t, J=7.5 Hz, 1H), 7.59 (dd, J=7.5 Hz, 1.5 Hz, 1H), 7.42 (s, 1H), 7.38-7.28 (m, 2H), 6.96 (s, 2H), 6.86 (d, J=8.5 Hz, 1H), 6.46 (s, 1H), 5.87 (br s, 1H), 5.63-5.56 (m, 1H), 4.67 (d, J=3.0 Hz, 1H), 4.12 (d, J=8.5 Hz, 1H), 3.28-3.17 (m, 1H), 2.33-2.22 (m, 1H), 1.67 (dd, J=16.5 Hz, 8.5 Hz, 1H)

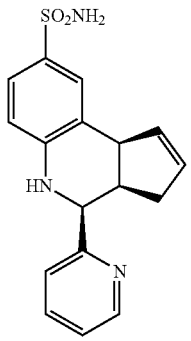 [SMILES: NS(=O)(=O)c1ccc2c(c1)[C@H]1C=CC[C@H]1[C@@H](c1ccccn1)N2]

4-(pyridin-2-yl)-3a,4,5,9b-tetrahydro-3H-cyclopenta[c]quinoline-8-sulfonamide (GAT170; 52)

¹H NMR (500 MHz, DMSO-d6) δ 8.58 (d, J=4.0 Hz, 1H), 7.85 (t, J=7.5 Hz, 1H), 7.53 (d, J=7.5 Hz, 1H), 7.45 (s, 1H), 7.38-7.28 (m, 2H), 6.96 (s, 2H), 6.86 (d, J=8.5 Hz, 1H), 6.46 (s, 1H), 5.87 (br s, 1H), 5.63-5.56 (m, 1H), 4.67 (d, J=3.0 Hz, 1H), 4.12 (d, J=8.5 Hz, 1H), 3.28-3.17 (m, 1H), 2.33-2.22 (m, 1H), 1.67 (dd, J=16.5 Hz, 8.5 Hz, 1H)

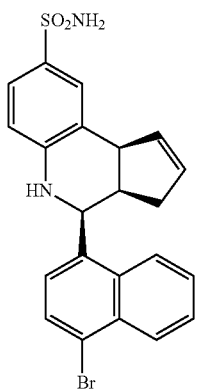 [SMILES: NS(=O)(=O)c1ccc2c(c1)[C@H]1C=CC[C@H]1[C@@H](c1ccc(Br)c3ccccc13)N2]

4-(4-bromonaphthalen-1-yl)-3a,4,5,9b-tetrahydro-3H-cyclopenta[c]quinoline-8-sulfonamide (GAT171; 53)

¹H NMR (500 MHz, CDCl₃) δ 8.36 (dd, J=8.5 Hz, 1.5 Hz, 1H), 8.10 (dd, J=8.5 Hz, 1.0 Hz, 1H), 7.84 (d, J=8.0 Hz, 1H), 7.69-7.58 (m, 4H), 7.56 (dd, J=8.0 Hz, 2.0 Hz, 1H), 6.74 (d, J=8.0 Hz, 1H), 5.93-5.86 (m, 1H), 5.48 (d, J=3.5 Hz, 1H), 4.73 (s, 2H), 4.24 (d, J=9.0 Hz, 1H), 4.18 (s, 1H), 3.31 (qdd, J=9.5 Hz, 3.5 Hz, 2.0 Hz, 1H), 2.54 (ddq, J=16.5 Hz, 10.0 Hz, 2.5 Hz, 1H), 1.65 (dddd, J=16.0 Hz, 7.5 Hz, 3.0 Hz, 1.5 Hz, 1H)

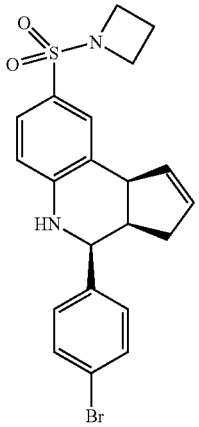 [SMILES: O=S(=O)(c1ccc2c(c1)[C@H]1C=CC[C@H]1[C@@H](c1ccc(Br)cc1)N2)N1CCC1]

8-(azetidin-1-ylsulfonyl)-4-(4-bromophenyl)-3a,4,5,9b-tetrahydro-3H-cyclopenta[c]quinolone (GAT173/GAT1305; 54)

1H NMR (500 MHz, DMSO-d6) δ 7.52 (d, J=8.0 Hz, 2H), 7.49 (d, J=1.5 Hz, 1H), 7.44 (dd, J=8.0 Hz, 2.0 Hz, 1H), 7.30 (d, J=8.5 Hz, 2H), 6.72 (d, J=8.5 Hz, 1H), 5.93-5.84 (m, 1H), 5.68 (d, J=5.5 Hz, 1H), 4.71 (d, J=3.0 Hz, 1H), 4.24 (s, 1H), 4.14 (d, J=10.0 Hz, 1H), 3.73 (sextet, J=6.5 Hz, 4H), 3.01 (qd, J=9.0 Hz, 3.0 Hz, 1H), 2.54 (ddq, J=16.0 Hz, 9.0 Hz, 2.0 Hz, 1H), 2.07 (quint, J=7.5 Hz, 2H), 1.83 (dd, J=16.5 Hz, 8.5 Hz, 1H)

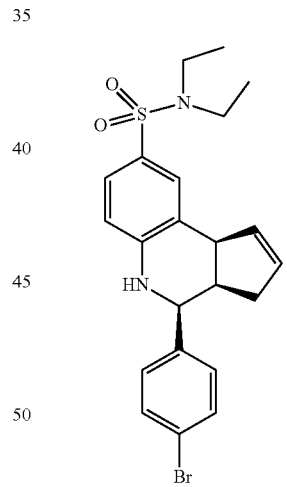

4-(4-bromophenyl)-N,N-diethyl-3a,4,5,9b-tetrahydro-3H-cyclopenta[c]quinoline-8-sulfonamide (GAT174/GAT1306; 55)

¹H NMR (500 MHz, CDCl₃) δ 7.48 (dd, J=8.0 Hz, 1.5 Hz, 2H), 7.43 (s, 1H), 7.33 (dd, J=8.0 Hz, 1.5 Hz, 1H), 7.29 (dd, J=8.5 Hz, 1.5 Hz, 2H), 6.65 (dd, J=8.5 Hz, 1.5 Hz, 1H), 5.87-5.78 (m, 1H), 5.69-5.59 (m, 1H), 4.65 (s, 1H), 4.32 (s, 1H), 4.08 (d, J=9.0 Hz, 1H), 3.27-3.09 (m, 4H), 2.98 (qd, J=9.0 Hz, 2.5 Hz, 1H), 2.56-2.44 (m, 1H), 1.78 (dd, J=11.0 Hz, 8.5 Hz, 1H)

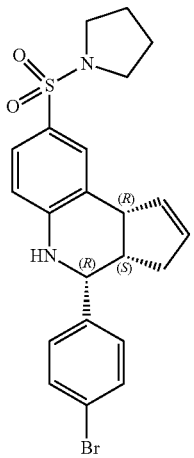

(3aS,4R,9bR)-4-(4-bromophenyl)-8-(pyrrolidin-1-ylsulfonyl)-3a,4,5,9b-tetrahydro-3H-cyclopenta[c]quinolone (GAT176; 56)

¹H NMR (500 MHz, DMSO-d6) δ 7.59 (d, J=8.5 Hz, 2H), 7.41 (d, J=8.5 Hz, 2H), 7.39 (d, J=1.5 Hz, 1H), 7.31 (dd, J=8.5 Hz, 2.0 Hz, 1H), 6.85 (d, J=8.5 Hz, 1H), 6.56 (s, 1H), 5.96-5.89 (m, 1H), 5.60 (d, J=5.0 Hz, 1H), 4.65 (d, J=3.0 Hz, 1H), 4.10 (d, J=8.5 Hz, 1H), 3.12-3.00 (m, 4H), 2.95 (q, J=9.0 Hz, 1H), 2.38-229 (m, 1H), 1.69-1.58 (m, 5H)

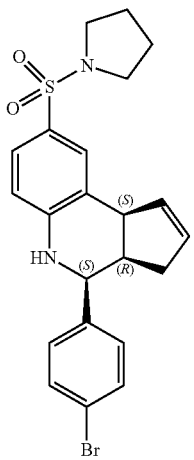

(3aR,4S,9bS)-4-(4-bromophenyl)-8-(pyrrolidin-1-ylsulfonyl)-3a,4,5,9b-tetrahydro-3H-cyclopenta[c]quinolone (GAT177; 57)

¹H NMR (500 MHz, DMSO-d6) δ 7.59 (d, J=8.5 Hz, 2H), 7.41 (d, J=8.5 Hz, 2H), 7.39 (d, J=1.5 Hz, 1H), 7.31 (dd, J=8.5 Hz, 2.0 Hz, 1H), 6.85 (d, J=8.5 Hz, 1H), 6.56 (s, 1H), 5.96-5.89 (m, 1H), 5.60 (d, J=5.0 Hz, 1H), 4.65 (d, J=3.0 Hz, 1H), 4.10 (d, J=8.5 Hz, 1H), 3.12-3.00 (m, 4H), 2.95 (q, J=9.0 Hz, 1H), 2.38-2.29 (m, 1H), 1.69-1.58 (m, 5H)

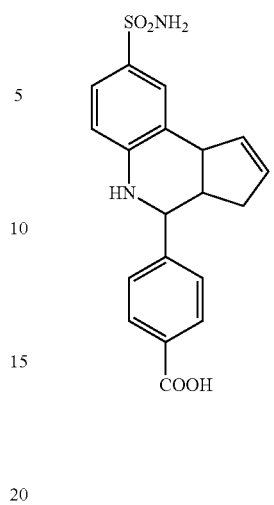

4-(8-sulfamoyl-3a,4,5,9b-tetrahydro-3H-cyclopenta[c]quinolin-4-yl)benzoic acid (GAT180; 58)

¹H NMR (500 MHz, DMSO) δ 12.92 (s, 1H) 7.97 (d, J=8.5 Hz, 2H) 7.58 (d, J=8.5 Hz, 2H), 7.44 (d, J=2 Hz, 1H), 7.34 (dd, J=8.5 Hz, 1H), 6.97 (s, 2H), 6.82 (d, J=8.5 Hz, 1H), 6.46 (s, 1H), 5.93-5.87 (m, 1H), 5.62 (d, J=5 Hz, 1H), 4.72 (d, J=3 Hz, 1H), 4.09 (br d, J=8 Hz, 1H), 2.98 (br q, J=8 Hz, 1H), 2.40-2.31 (m, 1H), 1.61 (dd, J=15.5 Hz, 9 Hz, 1H)

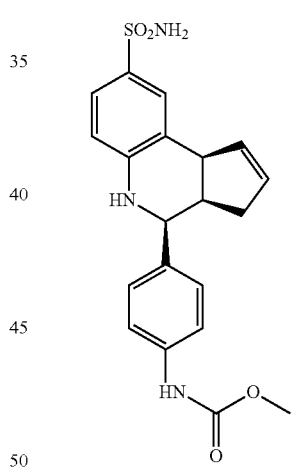

methyl(4-(8-sulfamoyl-3a,4,5,9b-tetrahydro-3H-cyclopenta[c]quinolin-4-yl)phenyl)carbamate (GAT181; 59)

¹H NMR (500 MHz, DMSO-d6) δ 8.31 (s, 1H), 7.99 (d, J=8.5 Hz, 2H) 7.61 (d, J=8.5 Hz, 2H), 7.45 (d, J=1.5 Hz, 1H), 7.35 (dd, J=8.5 Hz, 2 Hz, 1H), 6.95 (s, 2H), 6.82 (d, J=8.0 Hz, 1H), 6.46 (s, 1H), 5.92-5.87 (m, 1H), 5.61 (d, J=6.0 Hz, 1H), 4.73 (d, J=2.5 Hz, 1H), 4.09 (br d, J=8.5 Hz, 1H), 3.86 (s, 2H) 2.98 (br q, J=9.5 Hz, 1H), 2.39-2.30 (m, 1H), 1.60 (dd, J=16.5 Hz, 8.5 Hz, 1H)

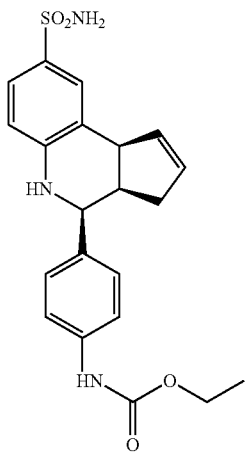 [SMILES: CCOC(=O)Nc1ccc([C@H]2Nc3ccc(S(N)(=O)=O)cc3[C@H]3C=CC[C@H]32)cc1]

ethyl(4-(8-sulfamoyl-3a,4,5,9b-tetrahydro-3H-cyclo-
penta[c]quinolin-4-yl)phenyl)carbamate (GAT182;
60)

$^1$H NMR (500 MHz, CDCl$_3$) δ 7.59 (d, J=1.5 Hz, 1H)
7.52 (dd, J=8 Hz, 2.5 Hz, 1H), 7.41 (d, J=8.5 Hz, 2H), 7.34
(d, J=8.5 Hz, 2H), 6.65 (d, J=8.5 Hz, 1H), 6.59 (s, 1H),
5.91-5.86 (m, 1H), 5.69 (d, J=4.5 Hz, 1H), 4.68 (d, J=3.0 Hz,
1H), 4.61 (s, 2H), 4.25 (q, J=7.0 Hz, 2H), 4.19 (s, 1H), 4.10
(d, J=8.0 Hz, 1H), 2.99 (qd, J=15.0 Hz, 7.0 Hz, 2.5 Hz, 1H),
2.59-2.51 (m, 1H), 1.84 (dd, J=13.0 Hz, 5.5 Hz, 1H), 1.33 (t,
J=7.0 Hz, 3H)

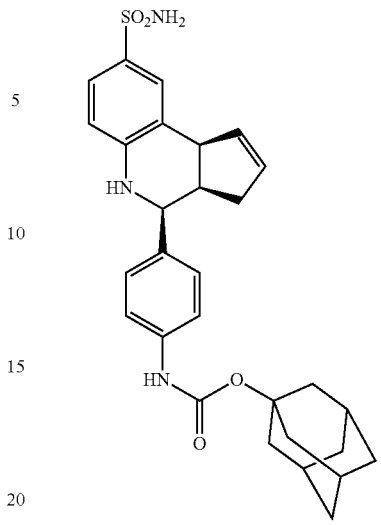

adamantan-1-yl (4-(8-sulfamoyl-3a,4,5,9b-tetra-
hydro-3H-cyclopenta[c]quinolin-4-yl)phenyl)car-
bamate (GAT184; 62)

$^1$H NMR (500 MHz, CDCl$_3$) δ 7.59 (d, J=2 Hz, 1H) 7.51
(dd, J=8.0 Hz, 2.0 Hz, 1H), 7.38 (d, J=9.0 Hz, 2H), 7.31 (d,
J=8.0 Hz, 2H), 6.64 (d, J=8.5 Hz, 1H) 6.54 (s, 1H), 5.90-5.85
(m, 1H), 5.68 (d, J=5.0 Hz, 1H), 4.70 (s, 2H), 4.65 (d, J=3.5
Hz, 1H), 4.19 (s, 1H), 4.09 (br d, J=10.0 Hz, 1H) 3.02-2.94
(m, 1H), 2.58-2.50 (m, 1H), 2.24-2.14 (m, 9H), 1.87-1.79
(m, 1H), 1.73-1.64 (m, 6H)

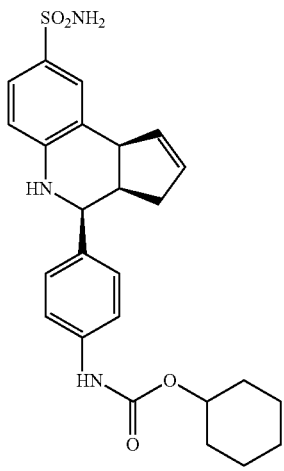 [SMILES: NS(=O)(=O)c1ccc2c(c1)[C@H]1C=CC[C@H]1[C@@H](c1ccc(NC(=O)OC3CCCCC3)cc1)N2]

cyclohexyl(4-(8-sulfamoyl-3a,4,5,9b-tetrahydro-3H-
cyclopenta[c]quinolin-4-yl)phenyl)carbamate
(GAT183; 61)

$^1$H NMR (500 MHz, Acetone-d6) δ 8.57 (s, 1H), 7.58 (d,
J=9.0 Hz, 2H) 7.58 (d, J=9.0 Hz, 2H), 7.54 (d, J=2.0 Hz,
1H), 7.44 (dd, J=9.0 Hz, 2.5 Hz, 1H), 7.39 (d, J=8.5 Hz, 2H),
6.87 (d, J=8.0 Hz, 1H), 6.19 (s, 2H), 5.94-5.89 (m, 1H), 5.65
(d, J=4.5 Hz, 1H), 5.53 (s, 1H), 4.72-4.65 (comp, 2H) 4.12
(br d, J=8.5 Hz, 1H) 3.07-2.99 (m, 1H), 2.57-2.49 (m, 1H),
1.95-1.22 (m, 1H)

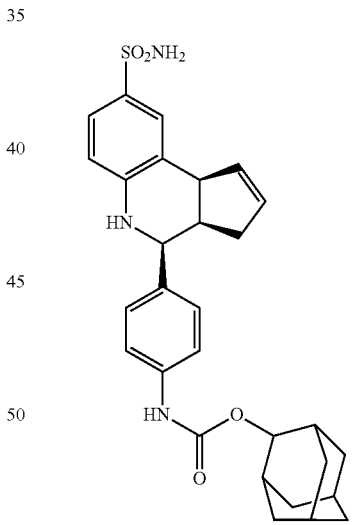

adamantan-2-yl (4-(8-sulfamoyl-3a,4,5,9b-tetra-
hydro-3H-cyclopenta[c]quinolin-4-yl)phenyl)car-
bamate (GAT185; 63)

$^1$H NMR (500 MHz, CDCl$_3$) δ 7.59 (d, J=1.5 Hz, 1H)
7.52 (dd, J=8.5 Hz, 2.5 Hz, 1H), 7.43 (d, J=8.0 Hz, 2H), 7.34
(d, J=8.0 Hz, 2H), 6.68 (s, 1H) 6.65 (d, J=8.0 Hz, 1H),
5.91-5.86 (m, 1H), 5.68 (d, J=5.0 Hz, 1H), 4.94 (m, 1H),
4.67 (s, 2H), 4.20 (s, 1H) 4.09 (d, J=5.5 Hz, 1H) 2.99 (qd,
J=17.5 Hz, 8.5 Hz, 3 Hz, 1H), 2.59-2.50 (m, 1H), 2.13-1.60
(m, 15H)

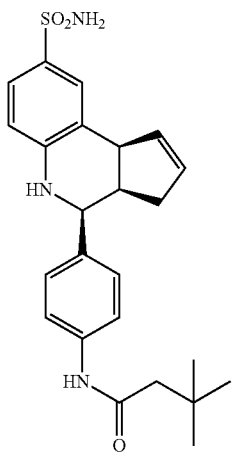 [SMILES: CC(C)(C)CC(=O)Nc1ccc([C@H]2Nc3ccc(S(N)(=O)=O)cc3[C@H]3C=CC[C@H]32)cc1]

3,3-dimethyl-N-(4-(8-sulfamoyl-3a,4,5,9b-tetra-hydro-3H-cyclopenta[c]quinolin-4-yl)phenyl)butanamide (GAT186; 64)

$^1$H NMR (500 MHz, DMSO) δ 9.80 (s, 1H) 7.60 (d, J=8.5 Hz, 2H) 7.43 (d, J=1.5 Hz, 1H), 7.36 (d, J=9.0 Hz, 2H), 7.33 (dd, J=8.0 Hz, 2.0 Hz, 1H) 6.96 (s, 2H), 6.81 (d, J=9.0 Hz, 1H), 6.32 (s, 1H), 5.92-5.86 (m, 1H), 5.63 (d, J=5.0 Hz, 1H), 4.58 (d, J=3.0 Hz, 1H), 4.07 (d, J=9.0 Hz, 1H), 2.92 (br q, J=7.5 Hz, 1H), 2.44-2.35 (m, 1H), 2.20 (s, 2H), 1.68 (dd, J=15.0 Hz, 8.5 Hz, 1H), 1.04 (s, 9H)

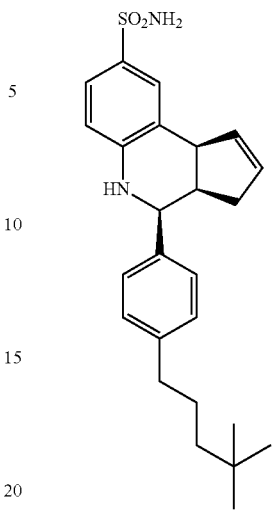

4-(4-(4,4-dimethylpentyl)phenyl)-3a,4,5,9b-tetra-hydro-3H-cyclopenta[c]quinoline-8-sulfonamide (GAT188; 66)

$^1$H NMR (500 MHz, CDCl$_3$) δ 7.60 (d, J=1.5 Hz, 1H) 7.52 (dd, J=8.0 Hz, 2.0 Hz, 1H), 7.31 (d, J=7.5 Hz, 2H), 7.21 (d, J=8.0 Hz, 2H), 6.64 (d, J=8.5 Hz, 1H), 5.91-5.86 (m, 1H), 5.71-5.66 (m, 1H), 4.69 (d, J=3.5 Hz, 1H), 4.66 (s, 2H), 4.22 (s, 1H) 4.11 (d, J=8.5 Hz, 1H), 3.01 (br q, J=9.0 Hz, 1H), 2.59 (t, J=7.5 Hz, 2H), 2.61-2.52 (m, 1H), 1.90-1.82 (m, 1H), 1.62-1.54 (m, 2H), 1.27-1.20 (m, 1H), 0.88 (s, 9H)

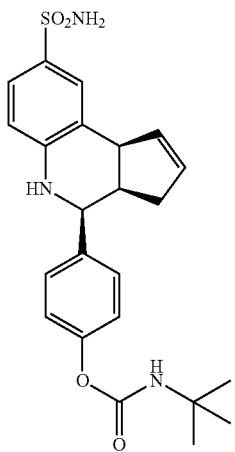 [SMILES: CC(C)(C)NC(=O)Oc1ccc([C@H]2Nc3ccc(S(N)(=O)=O)cc3[C@H]3C=CC[C@H]32)cc1]

4-(8-sulfamoyl-3a,4,5,9b-tetrahydro-3H-cyclopenta[c]quinolin-4-yl)phenyl tert-butylcarbamate (GAT187; 65)

$^1$H NMR (500 MHz, CDCl$_3$) δ 7.59 (d, J=1.5 Hz, 1H) 7.50 (dd, J=8.0 Hz, 1.5 Hz, 1H), 7.39 (d, J=8.0 Hz, 2H), 7.13 (d, J=8.0 Hz, 2H), 6.63 (d, J=8.5 Hz, 1H) 5.90-5.85 (m, 1H), 5.67 (d, J=4.0 Hz, 1H), 5.03 (s, 1H), 4.78 (s, 2H), 4.68 (d, J=3.0 Hz, 1H), 4.23 (s, 1H), 4.09 (br d, J=8.5 Hz, 1H) 2.98 (qd, J=17.5 Hz, 8.5 Hz, 2.0 Hz, 1H), 2.58-2.50 (m, 1H), 1.85 (dd, J=15.0 Hz, 7.0 Hz, 1.5 Hz, 1H), 1.40 (s, 9H)

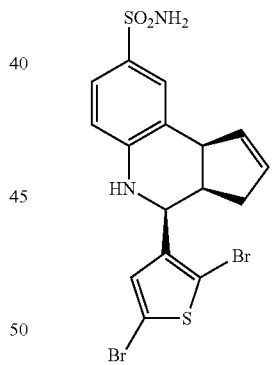

(3aR,4S,9bS)-4-(2,5-dibromothiophen-3-yl)-3a,4,5,9b-tetrahydro-3H-cyclopenta[c]quinoline-8-sulfonamide (GAT189; 67)

$^1$H NMR (500 MHz, CDCl$_3$) δ 7.60 (d, J=2.0 Hz, 1H), 7.53 (dd, J=9.0 Hz, 2.5 Hz, 1H), 7.05 (s, 1H), 6.64 (d, J=8.5 Hz, 1H), 5.93-5.86 (m, 1H), 5.75-5.68 (m, 1H), 4.78 (d, J=3.5 Hz, 1H), 4.12 (d, J=9.0 Hz, 1H), 4.06 (s, 1H), 3.05 (qdd, J=8.5 Hz, 3.0 Hz, 2.0 Hz, 1H), 2.58 (ddq, J=16.0 Hz, 9.5 Hz, 2.0 Hz, 1H), 2.08-1.99 (m, 1H)

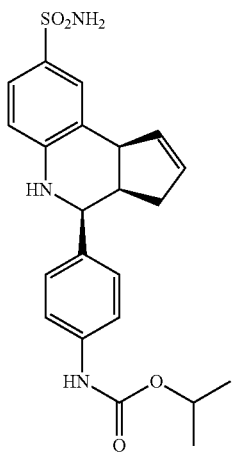 [SMILES: CC(C)OC(=O)Nc1ccc([C@H]2Nc3ccc(S(N)(=O)=O)cc3[C@H]3C=CC[C@H]32)cc1]

isopropyl (4-(8-sulfamoyl-3a,4,5,9b-tetrahydro-3H-cyclopenta[c]quinolin-4-yl)phenyl)carbamate (GAT190; 68)

$^1$H NMR (500 MHz, DMSO) δ 9.55 (s, 1H) 7.46 (d, J=9.0 Hz, 2H) 7.42 (d, J=2.0 Hz, 1H), 7.35-7.30 (m, 3H), 6.95 (s, 2H), 6.79 (d, J=8.5 Hz, 1H), 6.31 (s, 1H), 5.90-5.84 (m, 1H), 5.62 (d, J=5.5 Hz, 1H), 4.89 (septet, J=6.5 Hz, 1H), 4.56 (d, J=3.5 Hz, 1H), 4.05 (d, J=8.5 Hz, 1H) 3.86 (s, 2H) 2.90 (br q, J=8.0 Hz, 1H), 2.42-2.33 (m, 1H), 1.66 (dd, J=15.0 Hz, 8.5 Hz, 1H), 1.26 (d, J=6.5 Hz, 6H)

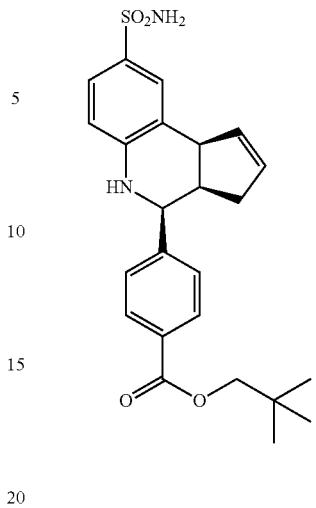

neopentyl 4-(8-sulfamoyl-3a,4,5,9b-tetrahydro-3H-cyclopenta[c]quinolin-4-yl)benzoate (GAT192; 70)

$^1$H NMR (500 MHz, DMSO) δ 8.01 (d, J=8.5 Hz, 2H) 7.62 (d, J=8.5 Hz, 2H), 7.45 (d, J=2.0 Hz, 1H), 7.35 (dd, J=8.0 Hz, 2H, 1H), 6.97 (s, 2H), 6.82 (d, J=9.0 Hz, 1H), 6.46 (s, 1H), 5.93-5.87 (m, 1H), 5.62 (d, J=6.0 Hz, 1H), 4.73 (d, J=2.5 Hz, 1H), 4.10 (br d, J=8.0 Hz, 1H), 4.02-3.96 (m, 2H), 2.98 (br q, J=8.5 Hz, 1H), 2.40-2.31 (m, 1H), 1.65-1.57 (m, 1H), 1.01 (s, 9H)

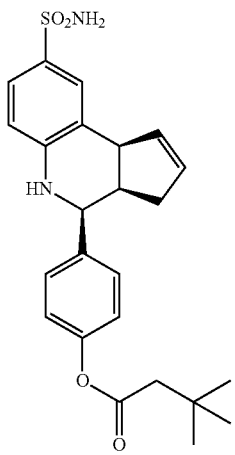 [SMILES: CC(C)(C)CC(=O)Oc1ccc([C@H]2Nc3ccc(S(N)(=O)=O)cc3[C@H]3C=CC[C@H]32)cc1]

4-(8-sulfamoyl-3a,4,5,9b-tetrahydro-3H-cyclopenta[c]quinolin-4-yl)phenyl 3,3-dimethylbutanoate (GAT191; 69)

$^1$H NMR (500 MHz, DMSO) δ 9.80 (s, 1H) 7.60 (d, J=8.5 Hz, 2H) 7.43 (d, J=1.5 Hz, 1H), 7.36 (d, J=9.0 Hz, 2H), 7.33 (dd, J=8.0 Hz, 2.0 Hz, 1H) 6.96 (s, 2H), 6.81 (d, J=9.0 Hz, 1H), 6.32 (s, 1H), 5.92-5.86 (m, 1H), 5.63 (d, J=5.0 Hz, 1H), 4.58 (d, J=3.0 Hz, 1H), 4.07 (d, J=9.0 Hz, 1H), 2.92 (br q, J=7.5 Hz, 1H), 2.44-2.35 (m, 1H), 2.20 (s, 2H), 1.68 (dd, J=15.0 Hz, 8.5 Hz, 1H), 1.04 (s, 9H)

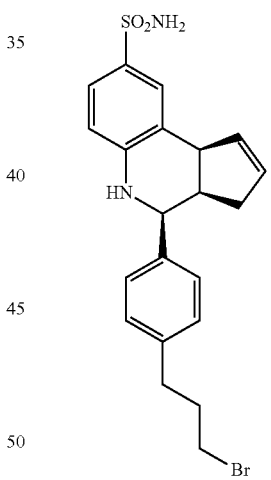

4-(4-(3-bromopropyl)phenyl)-3a,4,5,9b-tetrahydro-3H-cyclopenta[c]quinoline-8-sulfonamide (GAT193; 71)

$^1$H NMR (500 MHz, DMSO) δ 7.43 (s, 1H) 7.37 (d, J=8.5 Hz, 2H), 7.32 (dd, J=9.0 Hz, 2.5 Hz, 1H), 7.24 (d, J=8.5 Hz, 2H) 6.95 (s, 2H), 6.79 (d, J=8.0 Hz, 1H), 6.34 (s, 1H), 5.91-5.85 (m, 1H), 5.62 (d, J=5.0 Hz, 1H), 4.60 (d, J=3.0 Hz, 1H), 4.06 (br d, J=8.5 Hz, 1H), 2.92 (br q, J=8.5 Hz, 1H), 2.72 (t, J=7.0 Hz, 2H), 2.43-2.32 (m, 1H), 2.10 (quintet, J=7.0 Hz, 2H), 1.65 (dd, J=16.0 Hz, 9.5 Hz, 1H)

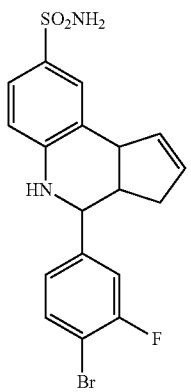 [SMILES: NS(=O)(=O)c1ccc2c(c1)C1C=CCC1C(c1ccc(Br)c(F)c1)N2]

4-(4-bromo-3-fluorophenyl)-3a,4,5,9b-tetrahydro-3H-cyclopenta[c]quinoline-8-sulfonamide (GAT900; 72)

$^1$H NMR (500 MHz, DMSO-d6) δ 7.73 (t, J=7.5 Hz, 1H), 7.46 (d, J=1.5 Hz, 1H), 7.35 (dd, J=8.0 Hz, 2.0 Hz, 1H), 7.27 (dd, J=8.5 Hz, 1.5 Hz, 1H), 6.98 (s, 2H), 6.80 (d, J=9.0 Hz, 1H), 6.42 (s, 1H), 5.93-5.85 (m, 1H), 5.62 (d, J=5.0 Hz, 1H), 4.65 (d, J=8.5 Hz, 1H), 4.06 (d, J=8.5 Hz, 1H), 3.02-2.92 (m, 1H), 2.37-2.26 (m, 1H), 1.66 (dd, J=16.0 Hz, 9.0 Hz, 1H)

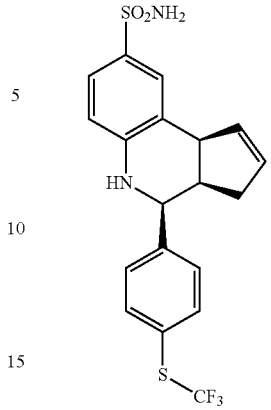

4-(4-((trifluoromethyl)thio)phenyl)-3a,4,5,9b-tetrahydro-3H-cyclopenta[c]quinoline-8-sulfonamide (GAT902; 74)

$^1$H NMR (500 MHz, DMSO-d6) δ 7.75 (d, J=8.5 Hz, 2H), 7.62 (d, J=8.5 Hz, 2H), 7.45 (d, J=1.5 Hz, 1H), 7.35 (dd, J=8.0 Hz, 2.0 Hz, 1H), 6.97 (s, 2H), 6.80 (d, J=8.0 Hz, 1H), 6.48 (s, 1H), 5.93-5.86 (m, 1H), 5.62 (d, J=5.0 Hz, 1H), 4.71 (d, J=3.0 Hz, 1H), 4.09 (d, J=8.5 Hz, 1H), 3.03-2.91 (m, 1H), 2.41-2.30 (m, 1H), 1.61 (dd, J=16.0 Hz, 10.0 Hz, 1H)

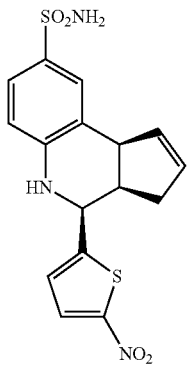 [SMILES: NS(=O)(=O)c1ccc2c(c1)[C@H]1C=CC[C@H]1[C@@H](c1ccc([N+](=O)[O-])s1)N2]

4-(5-nitrothiophen-2-yl)-3a,4,5,9b-tetrahydro-3H-cyclopenta[c]quinoline-8-sulfonamide (GAT901; 73)

$^1$H NMR (500 MHz, DMSO-d6) δ 8.11 (d, J=4.0 Hz, 1H), 7.47 (d, J=1.5 Hz, 1H), 7.38 (dd, J=8.5 Hz, 2.0 Hz, 1H), 7.30 (d, J=4.5 Hz, 1H), 7.02 (s, 2H), 6.82 (d, J=9.0 Hz, 1H), 6.70 (s, 1H), 5.98-5.90 (m, 1H), 5.66 (d, J=5.0 Hz, 1H), 5.01 (d, J=3.5 Hz, 1H), 4.07 (d, J=8.5 Hz, 1H), 3.02 (qdd, J=8.0 Hz, 3.5 Hz, 1.5 Hz, 1H), 2.39 (ddq, J=16.0 Hz, 9.0 Hz, 2.0 Hz, 1H), 1.93 (ddt, J=15.0 Hz, 8.5 Hz, 3.0 Hz, 1H)

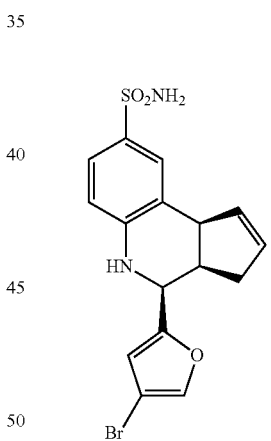

4-(4-bromofuran-2-yl)-3a,4,5,9b-tetrahydro-3H-cyclopenta[c]quinoline-8-sulfonamide (GAT903; 75)

$^1$H NMR (500 MHz, DMSO-d6) δ 7.90 (d, J=1.0 Hz, 1H), 7.44 (d, J=2.0 Hz, 1H), 7.34 (dd, J=8.0 Hz, 2.0 Hz, 1H), 6.98 (s, 2H), 6.78 (d, J=8.0 Hz, 1H), 6.57 (s, 1H), 6.39 (s, 1H), 5.88-5.80 (m, 1H), 5.64 (d, J=4.5 Hz, 1H), 4.61 (d, J=3.5 Hz, 1H), 4.05 (d, J=8.0 Hz, 1H), 3.06 (qdd, J=8.0 Hz, 4.0 Hz, 1.5 Hz, 1H), 2.40 (ddq, J=16.5 Hz, 8.5 Hz, 2.0 Hz, 1H), 2.06 (ddt, J=16.0 Hz, 8.0 Hz, 1.5 Hz, 1H)

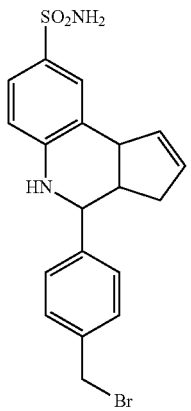 [SMILES: NS(=O)(=O)c1ccc2c(c1)C1C=CCC1C(c1ccc(CBr)cc1)N2]

4-(4-(bromomethyl)phenyl)-3a,4,5,9b-tetrahydro-3H-cyclopenta[c]quinoline-8-sulfonamide (GAT904; 76)

¹H NMR (500 MHz, DMSO-d6) δ 7.46 (s, 4H), 7.43 (d, J=2.0 Hz, 1H), 7.33 (dd, J=8.5 Hz, 2.0 Hz, 1H), 6.96 (s, 2H), 6.79 (d, J=8.0 Hz, 1H), 6.39 (s, 1H), 5.93-5.85 (m, 1H), 5.62 (d, J=5.5 Hz, 1H) 4.78 (s, 2H), 4.64 (d, J=3.5 Hz, 1H), 4.07 (d, J=8.5 Hz, 1H), 3.00-2.89 (m, 1H), 2.44-2.33 (m, 1H), 1.09-1.58 (m, 1H)

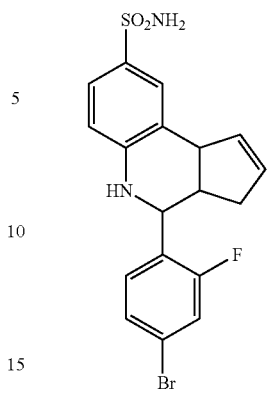

4-(4-bromo-2-fluorophenyl)-3a,4,5,9b-tetrahydro-3H-cyclopenta[c]quinoline-8-sulfonamide (GAT906; 79)

¹H NMR (500 MHz, DMOS-d6) δ 7.58 (dd, J=10.5 Hz, 2.0 Hz, 1H), 7.54 (t, J=8.5 Hz, 1H), 7.50 (dd, J=8.5 Hz, 2.0 Hz, 1H), 7.45 (d, J=2.0 Hz, 1H), 7.35 (dd, J=8.5 Hz, 2.0 Hz, 1H), 6.99 (s, 2H), 6.80 (d, J=8.5 Hz, 1H), 6.34 (s, 1H), 5.92-5.85 (m, 1H), 5.92-5.85 (m, 1H), 5.62 (d, J=5.0 Hz, 1H), 4.83 (d, J=3.5 Hz, 1H), 4.10 (d, J=8.0 Hz, 1H), 3.03-2.92 (m, 1H), 2.41-2.29 (m, 1H), 1.70 (dd, J=15.0 Hz, 9.0 Hz, 1H)

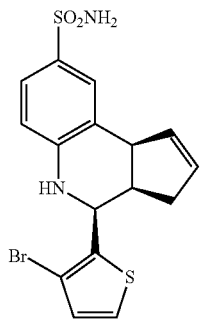 [SMILES: NS(=O)(=O)c1ccc2c(c1)[C@H]1C=CC[C@H]1[C@@H](c1sccc1Br)N2]

4-(3-bromothiophen-2-yl)-3a,4,5,9b-tetrahydro-3H-cyclopenta[c]quinoline-8-sulfonamide (GAT905; 77)

¹H NMR (500 MHz, DMSO-d6) δ 7.78 (d, J=3.0 Hz, 1H), 7.59 (d, J=3.5 Hz, 1H), 7.45 (d, J=2.0 Hz, 1H), 7.34 (dd, J=8.0 Hz, 2.5 Hz, 1H), 6.98 (s, 2H), 6.80 (d, J=8.5 Hz, 1H), 6.35 (s, 1H), 5.89-5.82 (m, 1H), 5.63 (d, J=5.0 Hz, 1H), 4.61 (d, J=3.0 Hz, 1H), 4.07 (d, J=9.5 Hz, 1H), 3.14-3.03 (m, 1H), 2.42 (ddq, J=16.0 Hz, 10.0 Hz, 2.0 Hz, 1H), 1.70 (dd, J=16.0 Hz, 9.5 Hz, 1H)

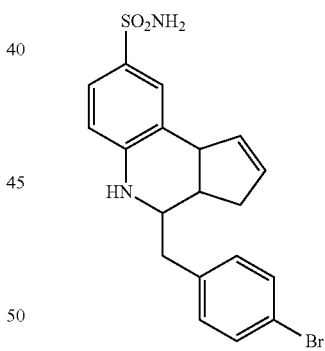

4-(4-bromobenzyl)-3a,4,5,9b-tetrahydro-3H-cyclopenta[c]quinoline-8-sulfonamide (GAT907; 79)

¹H NMR (500 MHz, DMSO-d6) δ 7.51 (d, J=8.0 Hz, 2H), 7.35 (d, J=2.0 Hz, 1H), 7.29 (dd, J=8.5 Hz, 2.0 Hz, 1H), 7.27 (d, J=8.5 Hz, 2H), 6.92 (d, J=9.0 Hz, 1H), 5.94 (s, 1H), 5.86-5.80 (m, 1H), 5.68 (d, J=5.5 Hz, 1H), 3.83 (d, J=8.5 Hz, 1H), 3.64-3.56 (m, 1H), 2.90 (dd, J=14.0 Hz, 5.5 Hz, 1H), 2.62 (dd, J=13.5 Hz, 9.0 Hz, 1H), 2.50-2.35 (m, 2H), 2.32-2.22 (m, 1H)

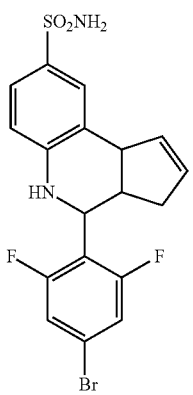

4-(4-bromo-2,6-difluorophenyl)-3a,4,5,9b-tetra-
hydro-3H-cyclopenta[c]quinoline-8-sulfonamide
(GAT908; 80)

$^1$H NMR (500 MHz, DMSO-d6) δ 7.51 (d, J=8.5 Hz, 2H), 7.44 (d, J=2.0 Hz, 1H), 7.34 (dd, J=8.5 Hz, 2.0 Hz, 1H), 6.97 (s, 2H), 6.68 (d, J=9.0 Hz, 1H), 6.58 (s, 1H), 5.91-5.84 (m, 1H), 5.66 (d, J=5.0 Hz, 1H), 4.94 (d, J=3.5 Hz, 1H), 4.08 (d, J=8.5 Hz, 1H), 2.97-2.86 (m, 1H), 2.66-2.54 (m, 1H), 2.08-1.96 (m, 1H)

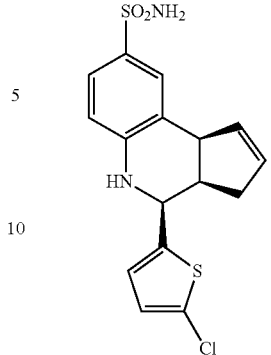

4-(5-chlorothiophen-2-yl)-3a,4,5,9b-tetrahydro-3H-
cyclopenta[c]quinoline-8-sulfonamide (GAT910;
82)

$^1$H NMR (500 MHz, DMSO-d6) δ 7.44 (d, J=2.0 Hz, 1H), 7.34 (dd, J=8.0 Hz, 2.0 Hz, 1H), 7.04 (d, J=3.5 Hz, 1H), 7.03 (d, J=4.5, 1H), 6.99 (s, 2H), 6.78 (d, J=8.5 Hz, 1H), 6.51 (s, 1H), 5.93-5.76 (m, 1H), 5.67 (d, J=5.0 Hz, 1H), 4.85 (d, J=3.5 Hz, 1H), 4.05 (d, J=8.5 Hz, 1H), 2.93 (qdd, J=12.5 Hz, 4.0 Hz, 2.0 Hz, 1H), 2.44 (ddq, J=16.0 Hz, 9.0 Hz, 2.0 Hz, 1H), 2.06-1.95 (m, 1H)

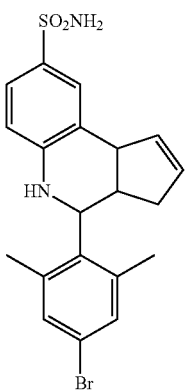 [SMILES: Cc1cc(Br)cc(C)c1C1Nc2ccc(S(N)(=O)=O)cc2C2C=CCC21]

4-(4-bromo-2,6-dimethylphenyl)-3a,4,5,9b-tetra-
hydro-3H-cyclopenta[c]quinoline-8-sulfonamide
(GAT909; 81)

$^1$H NMR (500 MHz, DMSO-d6) δ 7.61 (d, J=2.0 Hz, 1H), 7.35 (dd, J=8.5 Hz, 2.0 Hz, 1H), 7.30 (s, 2H), 6.94 (s, 2H), 6.68 (d, J=9.0 Hz, 1H), 6.59 (s, 1H), 5.94-5.88 (m, 1H), 5.82-5.74 (m, 1H), 4.10 (d, J=11.0 Hz, 1H), 3.99-3.91 (m, 1H), 2.99-2.87 (m, 1H), 2.59 (2.49 (m, 1H), 2.45-2.33 (m, 3H), 2.22 (s, 3H), 1.80-1.68 (m, 1H)

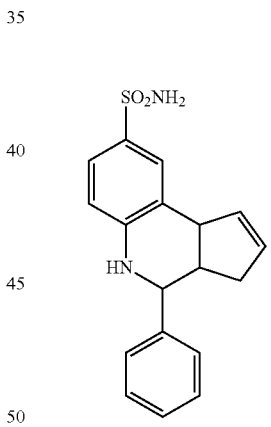

4-phenyl-3a,4,5,9b-tetrahydro-3H-cyclopenta[c]
quinoline-8-sulfonamide (GAT911; 83)

$^1$H NMR (500 MHz, DMSO-d6) δ 7.48-7.42 (m, 3H), 7.42-7.36 (m, 2H), 7.33 (dd, J=8.5 Hz, 2.0 Hz, 1H), 7.30 (t, J=7.5 Hz, 1H), 6.96 (s, 2H), 6.80 (d, J=9.0 Hz, 1H), 6.39 (s, 1H), 5.93-5.85 (m, 1H), 5.62 (d, J=5.0 Hz, 1H), 4.63 (d, J=3.0 Hz, 1H), 4.07 (d, J=8.5 Hz, 1H), 3.00-2.89 (m, 1H), 2.39 (ddq, J=16.0 Hz, 9.5 Hz, 2.0 Hz, 1H), 1.63 (dd, J=16.0 Hz, 9.0 Hz, 1H)

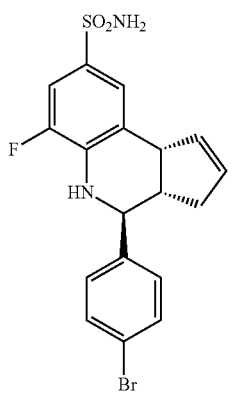 [SMILES: NS(=O)(=O)c1cc(F)c2c(c1)[C@@H]1C=CC[C@@H]1[C@@H](c1ccc(Br)cc1)N2]

4-(4-bromophenyl)-6-fluoro-3a,4,5,9b-tetrahydro-3H-cyclopenta[c]quinoline-8-sulfonamide (GAT912; 84)

¹H NMR (500 MHz, DMSO-d6) δ 7.56 (d, J=8.0 Hz, 2H), 7.44 (s, 1H), 7.34 (d, J=8.5 Hz, 2H), 7.29 (dd, J=10.5 Hz, 2.0 Hz, 1H), 7.13 (s, 2H), 6.43 (s, 1H), 5.94-5.87 (m, 1H), 5.80-5.73 (m, 1H), 3.89 (d, J=7.5 Hz, 1H), 3.83 (d, J=7.5 Hz, 1H), 2.66 (qd, J=8.0 Hz, 3.0 Hz, 1H), 2.50-2.40 (m, 1H), 2.09 (d, J=16.5 Hz, 1H)

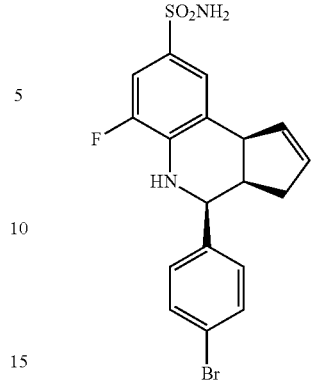

4-(4-bromophenyl)-6-fluoro-3a,4,5,9b-tetrahydro-3H-cyclopenta[c]quinoline-8-sulfonamide (GAT914; 86)

¹H NMR (500 MHz, DMSO-d6) δ 7.57 (d, J=8.5 Hz, 2H), 7.42 (d, J=9.0 Hz, 2H), 7.33 (s, 1H), 7.27 (dd, J=10.5 Hz, 2.0 Hz, 1H), 7.14 (s, 2H), 6.06 (s, 1H), 5.97-5.90 (m, 1H), 5.67-5.61 (m, 1H), 4.66 (d, J=3.5 Hz, 1H), 4.10 (d, J=8.5 Hz, 1H), 2.98-2.86 (m, 1H), 2.36-2.25 (m, 1H), 1.68-1.57 (m, 1H)

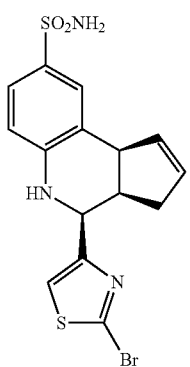 [SMILES: NS(=O)(=O)c1ccc2c(c1)[C@H]1C=CC[C@H]1[C@@H](c1csc(Br)n1)N2]

4-(2-bromothiazol-4-yl)-3a,4,5,9b-tetrahydro-3H-cyclopenta[c]quinoline-8-sulfonamide (GAT913; 85)

1H NMR (500 MHz, DMSO-d6) δ 7.74 (s, 1H), 7.46 (d, J=2.0 Hz, 1H), 7.36 (dd, J=9.0 Hz, 2.5 Hz, 1H), 7.01 (s, 2H), 6.75 (d, J=8.0 Hz, 1H), 6.59 (s, 1H), 5.93-5.88 (m, 1H), 5.63 (d, J=5.5 Hz, 1H), 4.97 (d, J=3.5 Hz, 1H), 4.06 (d, J=8.5 Hz, 1H), 2.96 (qdd, J=9.0 Hz, 2.5 Hz, 1.0 Hz, 1H), 2.41 (ddq, J=16.0 Hz, 9.0 Hz, 2.0 Hz, 1H), 2.08 (ddt, J=15.5 Hz, 9.0 Hz, 1.5 Hz, 1H)

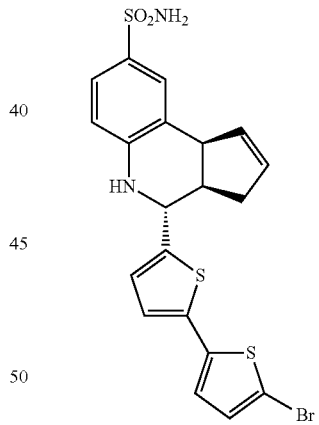

4-(5'-bromo-[2,2'-bithiophen]-5-yl)-3a,4,5,9b-tetrahydro-3H-cyclopenta[c]quinoline-8-sulfonamide (GAT915; 87)

¹H NMR d (500 MHz, DMSO-d6) δ 7.59 (d, J=2.0 Hz, 1H), 7.37 (dd, J=9.0 Hz, 2.0 Hz, 1H), 7.22 (d, J=3.5 Hz, 1H), 7.18 (d, J=4.0 Hz, 1H), 7.15-7.10 (m, 2H), 6.99 (s, 2H), 6.83 (s, 1H), 6.76 (d, J=8.5 Hz, 1H), 5.92-5.85 (m, 1H), 5.79-5.72 (m, 1H), 4.01 (d, J=8.5, 1H), 3.98-3.90 (m, 1H), 2.62-2.50 (m, 2H), 2.26-2.18 (m, 1H)

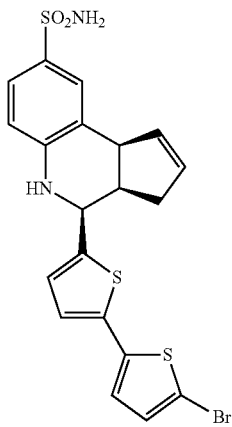 [SMILES: NS(=O)(=O)c1ccc2c(c1)[C@H]1C=CC[C@H]1[C@@H](c1ccc(-c3ccc(Br)s3)s1)N2]

4-(5'-bromo-[2,2'-bithiophen]-5-yl)-3a,4,5,9b-tetra-hydro-3H-cyclopenta[c]quinoline-8-sulfonamide (GAT916; 88)

$^1$H NMR (500 MHz, DMSO-d6) δ 7.44 (d, J=2.0 Hz, 1H), 7.34 (dd, J=8.5 Hz, 2.0 Hz, 1H), 7.24-7.20 (m, 1H), 7.14 (d, J=3.5 Hz, 1H), 7.12 (d, J=4.0 Hz, 1H), 6.99 (s, 2H), 6.79 (d, J=8.5 Hz, 1H), 6.53 (s, 1H), 5.94-5.87 (m, 1H), 5.72-5.64 (m, 1H), 4.90 (d, J=3.0 Hz, 1H), 4.12-4.03 (m, 1H), 3.03-2.90 (m, 1H), 2.55-2.45 (m, 1H), 2.07-1.95 (m, 1H)

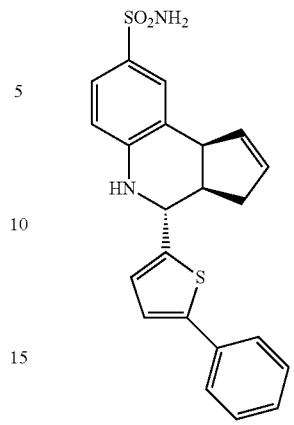

4-(5-phenylthiophen-2-yl)-3a,4,5,9b-tetrahydro-3H-cyclopenta[c]quinoline-8-sulfonamide (GAT918; 90)

1H NMR 7.64 (dd, J=8.0 Hz, 1.0 Hz, 2H), 7.60 (d, J=2.0 Hz, 1H), 7.46-7.38 (dd, J=9.0 Hz, 2.0 Hz, 1H), 7.17 (d, J=3.5 Hz, 1H), 6.99 (s, 2H), 6.83 (s, 1H), 6.78 (d, J=8.5 Hz, 1H), 5.94-5.86 (m, 1H), 5.80-5.73 (m, 1H), 4.02 (d, J=9.5 Hz, 1H), 4.00-3.93 (m, 1H), 2.67-2.58 (m, 1H), 2.58-2.50 (m, 1H), 2.29-2.19 (m, 1H)

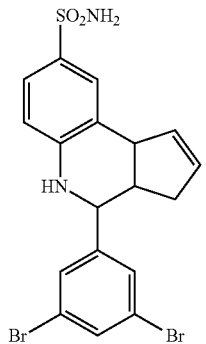 [SMILES: NS(=O)(=O)c1ccc2c(c1)C1C=CCC1C(c1cc(Br)cc(Br)c1)N2]

4-(3,5-dibromophenyl)-3a,4,5,9b-tetrahydro-3H-cyclopenta[c]quinoline-8-sulfonamide (GAT917; 89)

$^1$H NMR (500 MHz, DMSO-d6) δ 7.77 (t, J=1.5 Hz, 1H), 7.67 (d, J=1.5 Hz, 2H), 7.44 (d, J=2.0 Hz, 1H), 7.35 (dd, J=8.0 Hz, 2.0 Hz, 1H), 6.98 (s, 2H), 6.80 (d, J=8.5 Hz, 1H), 6.45 (s, 1H), 5.93-5.86 (m, 1H), 5.62 (d, J=5.0 Hz, 1H), 4.66 (d, J=3.5 Hz, 1H), 4.04 (d, J=9.0 Hz, 1H), 3.04-2.93 (m, 1H), 1.67 (dd, J=15.5 Hz, 9.0 Hz, 1H)

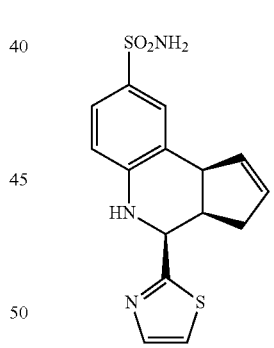

4-(thiazol-2-yl)-3a,4,5,9b-tetrahydro-3H-cyclopenta[c]quinoline-8-sulfonamide (GAT919; 91)

$^1$H NMR (500 MHz, DMSO-d6) δ 7.82 (d, J=3.5 Hz, 1H), 7.71 (d, J=3.5 Hz, 1H), 7.46 (d, J=2.0 Hz, 1H), 7.37 (dd, J=9.0 Hz, 2.0 Hz, 1H), 7.01 (s, 2H), 6.85 (d, J=9.0 Hz, 1H), 6.70 (s, 1H), 5.96-5.87 (m, 1H), 5.63 (d, J=5.5 Hz, 1H), 4.99 (d, J=3.5 Hz, 1H), 4.11 (d, J=9.0 Hz, 1H), 3.09 (qdd, J=9.0 Hz, 4.0 Hz, 1.0 Hz, 1H), 2.42 (ddq, J=16.0 Hz, 9.0 Hz, 2.0 Hz, 1H), 1.85 (dd, J=15.0 Hz, 8.0 Hz, 1H)

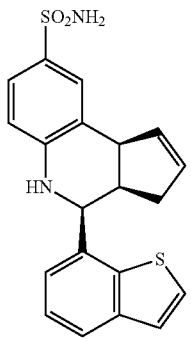 [SMILES: NS(=O)(=O)c1ccc2c(c1)[C@H]1C=CC[C@H]1[C@@H](c1cccc3ccsc13)N2]

4-(benzo[b]thiophen-7-yl)-3a,4,5,9b-tetrahydro-3H-cyclopenta[c]quinoline-8-sulfonamide (GAT920; 92)

¹H NMR (500 MHz, Acetone-d6) δ 7.90 (d, J=8.5 Hz, 1H), 7.73 (d, J=5.5 Hz, 1H), 7.67-7.58 (m, 2H), 7.58-7.44 (m, 3H), 6.98 (d, J=8.5 Hz, 1H), 6.29 (s, 2H), 6.03-5.96 (m, 1H), 5.76 (s, 1H), 5.71-5.67 (m, 1H), 5.09 (d, J=2.0 Hz, 1H), 4.28 (d, J=9.0 Hz, 1H), 3.44-3.34 (m, 1H), 2.74-2.62 (m, 1H)

4-(6-bromopyridin-3-yl)-3a,4,5,9b-tetrahydro-3H-cyclopenta[c]quinoline-8-sulfonamide (GAT922; 94)

¹H NMR (500 MHz, DMSO-d6) δ 8.47 (d, J=3.0 Hz, 1H), 7.82 (dd, J=8.0 Hz, 3.0 Hz, 1H), 7.68 (d, J=7.5 Hz, 1H), 7.45 (d, J=2.0 Hz, 1H), 7.35 (dd, J=8.5 Hz, 2.5 Hz, 1H), 6.99 (s, 2H), 6.78 (d, J=8.0 Hz, 1H), 6.46 (s, 1H), 5.93-5.87 (m, 1H), 5.63 (d, J=5.0 Hz, 1H), 4.69 (d, J=3.5 Hz, 1H), 4.07 (d, J=8.5 Hz, 1H), 3.03-2.93 (m, 1H), 2.40-2.29 (m, 1H), 1.76-1.66 (m, 1H)

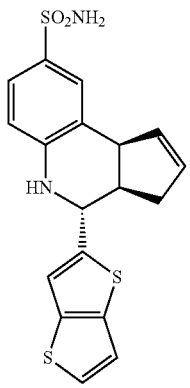 [SMILES: NS(=O)(=O)c1ccc2c(c1)[C@H]1C=CC[C@H]1[C@H](c1cc3sccc3s1)N2]

4-(thieno[3,2-b]thiophen-2-yl)-3a,4,5,9b-tetrahydro-3H-cyclopenta[c]quinoline-8-sulfonamide (GAT921; 93)

¹H NMR (500 MHz, DMSO-d6) δ 7.64 (d, J=4.5 Hz, 1H), 7.59 (d, J=2.0 Hz, 1H), 7.52 (s, 1H), 7.42 (d, J=5.5 Hz, 1H), 7.38 (dd, J=9.0 Hz, 2.0 Hz, 1H), 6.98 (s, 2H), 6.85 (s, 1H), 6.76 (d, J=9.0 Hz, 1H), 5.94-5.86 (m, 1H), 5.79-5.73 (m, 1H), 4.08 (d, J=8.5 Hz, 1H), 3.97 (d, J=7.5 Hz, 1H), 2.64 (qd, J=7.0 Hz, 2.0 Hz, 1H), 2.60-2.50 (m, 1H), 2.30-2.21 (m, 1H)

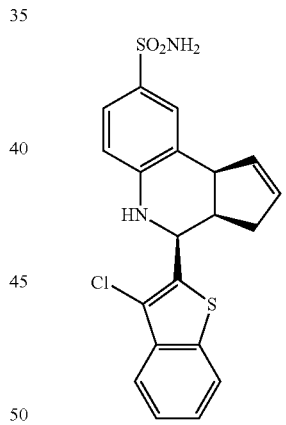

4-(3-chlorobenzo[b]thiophen-2-yl)-3a,4,5,9b-tetrahydro-3H-cyclopenta[c]quinoline-8-sulfonamide (GAT923; 95)

¹H NMR (500 MHz, DMSO-d6) δ 8.06 (d, J=7.5 Hz, 1H), 7.80 (d, J=8.0 Hz, 1H), 7.58-7.44 (m, 3H), 7.38 (dd, J=8.0 Hz, 2.0 Hz, 1H), 6.81 (d, J=9.0 Hz, 1H), 6.69 (s, 1H), 6.00-5.92 (m, 1H), 5.68 (d, J=5.5 Hz, 1H), 5.19 (d, J=4.0 Hz, 1H), 4.16 (d, J=8.5 Hz, 1H), 3.16-3.05 (m, 1H), 2.59 (ddq, J=16.0 Hz, 9.5 Hz, 2.0 Hz, 1H), 2.00 (dd, J=8.0 Hz, 1.5 Hz, 1H)

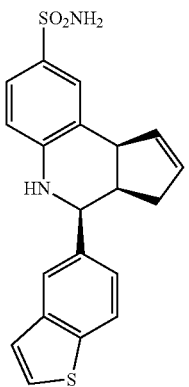 [SMILES: NS(=O)(=O)c1ccc2c(c1)[C@H]1C=CC[C@H]1[C@@H](c1ccc3sccc3c1)N2]

4-(benzo[b]thiophen-5-yl)-3a,4,5,9b-tetrahydro-3H-cyclopenta[c]quinoline-8-sulfonamide (GAT924; 96)

¹H NMR (500 MHz, DMSO-d6) δ 8.01 (d, J=8.0 Hz, 1H), 7.97 (d, J=1.5 Hz, 1H), 7.78 (d, J=5.5 Hz, 1H), 7.50 (dd, J=5.5 Hz, 1.0 Hz, 1H), 7.46 (s, 1H), 7.45 (dd, J=6.5 Hz, 1.5 Hz, 1H), 7.35 (dd, J=9.0 Hz, 2.0 Hz, 1H), 6.97 (s, 2H), 6.84 (d, J=8.5 Hz, 1H), 6.46 (s, 1H), 5.93-5.87 (m, 1H), 5.62 (d, J=5.0 Hz, 1H), 4.77 (d, J=3.0 Hz, 1H), 4.11 (d, J=8.5 Hz, 1H), 3.07-2.98 (m, 1H), 2.49-2.38 (m, 1H), 1.69-1.57 (m, 1H)

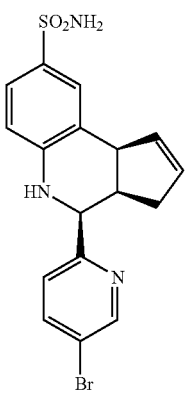

4-(5-bromopyridin-2-yl)-3a,4,5,9b-tetrahydro-3H-cyclopenta[c]quinoline-8-sulfonamide (GAT925; 97)

¹H NMR (500 MHz, DMSO-d6) δ 8.71 (d, J=2.0 Hz, 1H), 8.11 (dd, J=8.5 Hz, 2.5 Hz, 1H), 7.52 (d, J=8.5 Hz, 1H), 7.45 (d, J=2.0 Hz, 1H), 7.35 (dd, J=9.0 Hz, 2.0 Hz, 1H), 6.98 (s, 2H), 6.85 (d, J=9.0 Hz, 1H), 6.49 (s, 1H), 5.92-5.84 (m, 1H), 5.60 (d, J=4.5 Hz, 1H), 4.66 (d, J=3.5 Hz, 1H), 4.11 (d, J=7.5 Hz, 1H), 3.22-3.12 (m, 1H), 2.30-2.19 (m, 1H), 1.72-1.62 (m, 1H)

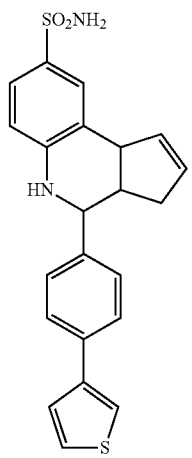 [SMILES: NS(=O)(=O)c1ccc2c(c1)C1C=CCC1C(c1ccc(-c3ccsc3)cc1)N2]

4-(4-(thiophen-3-yl)phenyl)-3a,4,5,9b-tetrahydro-3H-cyclopenta[c]quinoline-8-sulfonamide (GAT926; 98)

¹H NMR (500 MHz, DMSO-d6) δ 7.88 (dd, J=3.0 Hz, 1.5 Hz, 1H), 7.75 (d, J=8.5 Hz, 2H), 7.65 (dd, J=5.0 Hz, 2.5 Hz, 1H), 7.59 (dd, J=5.0 Hz, 1.5 Hz, 1H), 7.46 (d, J=8.0 Hz, 2H), 7.44 (d, J=1.5 Hz, 1H), 7.34 (dd, J=8.0 Hz, 2.5 Hz, 1H), 6.97 (s, 2H), 6.82 (d, J=8.5 Hz, 1H), 6.41 (s, 1H), 5.93-5.86 (m, 1H), 5.63 (d, J=5.0 Hz, 1H), 4.65 (d, J=3.0 Hz, 1H), 4.09 (d, J=8.0 Hz, 1H), 2.98 (q, J=8.0 Hz, 1H), 2.41 (ddq, J=16.5 Hz, 10.0 Hz, 2.0 Hz, 1H), 1.69 (dd, J=15.0 Hz, 8.5 Hz, 1H)

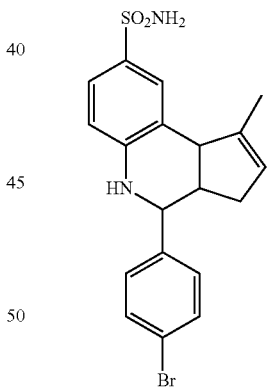

4-(4-bromophenyl)-1-methyl-3a,4,5,9b-tetrahydro-3H-cyclopenta[c]quinoline-8-sulfonamide (GAT928; 99)

¹H NMR (500 MHz, DMSO-d6) δ 7.58 (d, J=8.5 Hz, 2H), 7.41 (d, J=9.0 Hz, 2H), 7.33 (dd, J=8.5 Hz, 2.0 Hz, 1H), 6.96 (s, 2H), 6.79 (d, J=8.0 Hz, 1H), 6.38 (s, 1H), 5.94 (s, 1H), 4.56 (d, J=3.0 Hz, 1H), 4.00 (d, J=8.5 Hz, 1H), 3.03-2.93 (m, 1H), 2.38-2.28 (m, 1H), 1.48 (dd, J=16.0 Hz, 9.0 Hz, 1H)

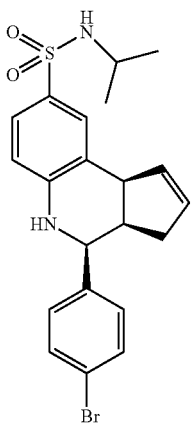 [SMILES: CC(C)NS(=O)(=O)c1ccc2c(c1)[C@H]1C=CC[C@H]1[C@@H](c1ccc(Br)cc1)N2]

4-(4-bromophenyl)-N-isopropyl-3a,4,5,9b-tetra-hydro-3H-cyclopenta[c]quinoline-8-sulfonamide
(GAT1308; 100)

1H NMR (500 MHz, DMSO-d6) δ 7.59 (d, J=8.5 Hz, 2H), 7.44-7.38 (m, 3H), 7.30 (dd, J=8.0 Hz, 2.0 Hz, 1H), 7.13 (d, J=8.5 Hz, 1H), 6.81 (d, J=8.5 Hz, 1H), 6.44 (s, 1H), 5.91-5.82 (m, 1H), 5.61 (d, J=5.0 Hz, 1H), 4.63 (d, J=3.5 Hz, 1H), 4.08 (d, J=9.0 Hz, 1H), 3.13 (sextet, J=7.0 Hz, 1H), 2.93 (qdd, J=11.5 Hz, 3.5 Hz, 1.5 Hz, 1H), 2.43 (ddq, J=16.0 Hz, 9.5 Hz, 2.0 Hz, 1H), 1.64 (dd, J=15.0 Hz, 8.5 Hz, 1H), 0.95 (d, J=7.0 Hz, 3H), 0.92 (d, J=6.0 Hz, 3H)

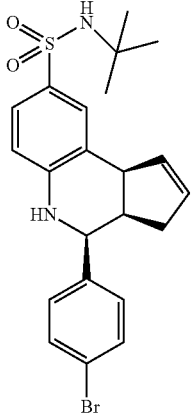 [SMILES: CC(C)(C)NS(=O)(=O)c1ccc2c(c1)[C@H]1C=CC[C@H]1[C@@H](c1ccc(Br)cc1)N2]

4-(4-bromophenyl)-N-(tert-butyl)-3a,4,5,9b-tetra-hydro-3H-cyclopenta[c]quinoline-8-sulfonamide
(GAT1309; 101)

¹H NMR (500 MHz, DMSO-d6) δ 7.59 (d, J=9.0 Hz, 2H), 7.45-7.38 (m, 3H), 7.32 (dd, J=8.5 Hz, 2.0 Hz, 1H), 7.06 (s, 1H), 6.80 (d, J=8.5 Hz, 1H), 6.40 (s, 1H), 5.88-5.82 (m, 1H), 5.61 (d, J=5.5 Hz, 1H), 4.62 (d, J=3.0 Hz, 1H), 4.08 (d, J=9.0 Hz, 1H), 2.94 (q, J=9.5 Hz, 1H), 2.35 (ddq, J=16.0 Hz, 9.0 Hz, 2.0 Hz, 1H), 1.64 (dd, J=16.0 Hz, 9.5 Hz, 1H), 1.07 (s, 9H)

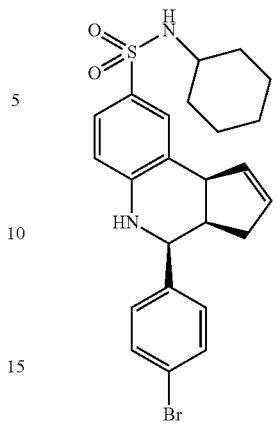

4-(4-bromophenyl)-N-cyclohexyl-3a,4,5,9b-tetra-hydro-3H-cyclopenta[c]quinoline-8-sulfonamide
(GAT1310; 102)

¹H NMR (500 MHz, DMSO-d6) δ 7.58 (d, J=8.5 Hz, 2H), 7.45-7.38 (m, 3H; 7.41 (d, J=8.5 Hz, 2H)), 7.31 (dd, J=8.0 Hz, 2.0 Hz, 1H), 7.18 (d, J=7.0 Hz, 1H), 6.80 (d, J=8.5 Hz, 1H), 6.43 (s, 1H), 5.92-5.83 (m, 1H), 5.60 (d, J=5.0 Hz, 1H), 4.63 (d, J=3.5 Hz, 1H), 4.08 (d, J=8.5 Hz, 1H), 2.93 (q, J=9.5 Hz, 1H), 2.89-2.78 (m, 1H), 2.34 (ddq, J=16.0 Hz, 9.5 Hz, 2.0 Hz, 1H), 1.67-1.50 (m, 4H), 1.64 (dd, J=15.5 Hz, 8.5 Hz, 1H), 1.41 (d, J=11.5 Hz, 1H), 1.20-0.96 (m, 5H)

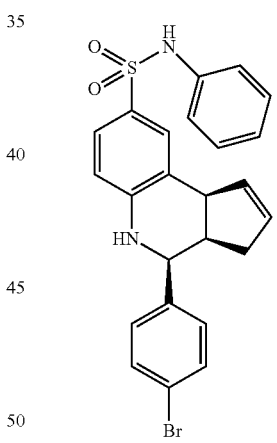

4-(4-bromophenyl)-N-phenyl-3a,4,5,9b-tetrahydro-3H-cyclopenta[c]quinoline-8-sulfonamide
(GAT1311; 103)

¹H NMR (500 MHz, DMSO-d6) δ 9.90 (s, 1H), 7.57 (d, J=9.0 Hz, 2H), 7.37 (d, J=9.0 Hz, 2H), 7.35 (d, J=2.0 Hz, 1H), 7.27 (dd, J=8.5 Hz, 2.0 Hz, 1H), 7.24-7.18 (m, 2H), 7.09 (dd, J=8.5 Hz, 2.0 Hz, 2H), 7.01-6.96 (m, 1H), 6.74 (d, J=8.0 Hz, 1H), 6.50 (s, 1H), 5.78-5.72 (m, 1H), 5.56 (d, J=5.0 Hz, 1H), 4.60 (d, J=3.5 Hz, 1H), 4.01 (d, J=9.0 Hz, 1H), 2.90 (qdd, J=10.5 Hz, 3.5 Hz, 1.5 Hz, 1H), 2.27 (ddq, J=16.5 Hz, 9.5 Hz, 2.0 Hz, 1H), 1.60 (ddt, J=15.0 Hz, 8.5 Hz, 1.5 Hz, 1H)

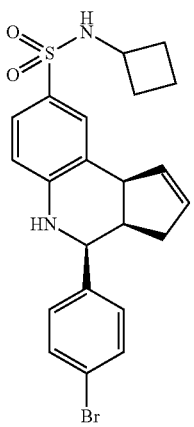 [SMILES: O=S(=O)(NC1CCC1)c1ccc2c(c1)[C@H]1C=CC[C@H]1[C@@H](c1ccc(Br)cc1)N2]

4-(4-bromophenyl)-N-cyclobutyl-3a,4,5,9b-tetra-
hydro-3H-cyclopenta[c]quinoline-8-sulfonamide
(GAT1312; 104)

¹H NMR (500 MHz, DMSO-d6) δ 7.58 (d, J=9.0 Hz, 2H), 7.51 (d, J=8.5 Hz, 1H), 7.41 (d, J=9.0 Hz, 2H), 7.38 (d, J=2.0 Hz, 1H), 7.28 (dd, J=8.5 Hz, 2.0 Hz, 1H), 6.80 (d, J=8.0 Hz, 1H), 6.44 (s, 1H), 5.92-5.85 (m, 1H), 5.61 (d, J=6.0 Hz, 1H), 4.62 (d, J=3.5 Hz, 1H), 4.07 (d, J=8.5 Hz, 1H), 3.55 (sextet, J=8.0 Hz, 1H), 2.99-2.88 (m, 1H), 2.34 (ddq, J=16.0 Hz, 9.5 Hz, 2.0 Hz, 1H), 1.96-1.82 (m, 2H), 1.77-1.59 (m, 3H), 1.52-1.41 (m, 2H)

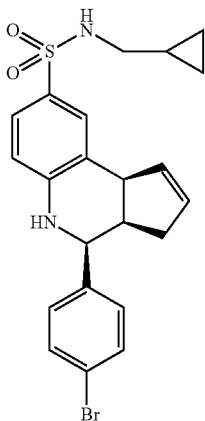 [SMILES: O=S(=O)(NCC1CC1)c1ccc2c(c1)[C@H]1C=CC[C@H]1[C@@H](c1ccc(Br)cc1)N2]

4-(4-bromophenyl)-N-(cyclopropylmethyl)-3a,4,5,
9b-tetrahydro-3H-cyclopenta[c]quinoline-8-sulfona-
mide (GAT1314; 105)

¹H NMR (500 MHz, DMSO-d6) δ 7.59 (d, J=8.5 Hz, 2H), 7.41 (d, J=9.0 Hz, 2H), 7.39 (d, J=2.0 Hz, 1H), 7.32-7.24 (m, 2H), 6.80 (d, J=8.5 Hz, 1H), 6.44 (s, 1H), 5.92-5.84 (m, 1H), 5.61 (d, J=5.5 Hz, 1H), 4.63 (d, J=3.0 Hz, 1H), 4.07 (d, J=9.0 Hz, 1H), 2.98-2.88 (m, 1H), 2.62-2.50 (m, 2H), 2.39-2.28 (m, 1H), 1.64 (dd, J=15.0 Hz, 8.0 Hz, 1H), 0.84-0.74 (m, 1H), 0.39-0.31 (m, 2H), 0.12-0.03 (m, 2H)

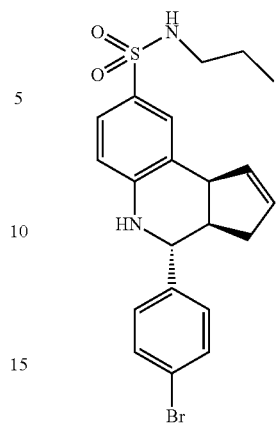

4-(4-bromophenyl)-N-propyl-3a,4,5,9b-tetrahydro-
3H-cyclopenta[c]quinoline-8-sulfonamide
(GAT1318; 106)

¹H NMR (500 MHz, DMSO-d6) δ 7.59 (d, J=8.5 Hz, 2H), 7.55 (d, J=2.0 Hz, 1H), 7.39 (d, J=8.0 Hz, 2H), 7.31 (dd, J=8.5 Hz, 2.0 Hz, 1H), 7.14 (t, J=6.0 Hz, 1H), 6.75 (d, J=8.0 Hz, 1H), 6.67 (s, 1H), 5.89 (d, J=5.0 Hz, 1H), 5.76-5.71 (m, 1H), 3.97-3.88 (m, 1H), 3.66 (d, J=10.0 Hz, 1H), 2.64 (q, J=6.5 Hz, 2H), 2.57 (q, J=7.5 Hz, 1H), 2.46-2.35 (m, 1H), 2.00 (d, J=16.5 Hz, 1H), 1.36 (sextet, J=7.5 Hz, 2H), 0.80 (t, J=7.5 Hz, 3H)

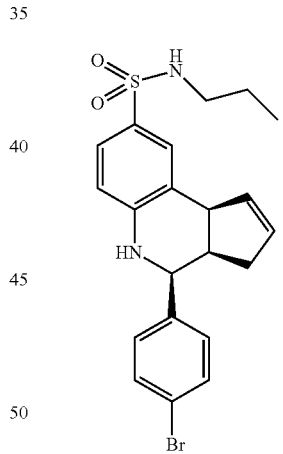

4-(4-bromophenyl)-N-propyl-3a,4,5,9b-tetrahydro-
3H-cyclopenta[c]quinoline-8-sulfonamide
(GAT1319; 107)

¹H NMR (500 MHz, DMSO) δ 7.59 (d, J=8.5 Hz, 2H), 7.41 (d, J=8.5 Hz, 2H), 7.38 (d, J=2.0 Hz, 1H), 7.29 (dd, J=8.5 Hz, 2.0 Hz, 1H), 7.14 (t, J=5.5 Hz, 1H), 6.82 (d, J=9.0 Hz, 1H), 6.45 (s, 1H), 5.93-5.84 (m, 1H), 5.61 (d, J=5.0 Hz, 1H), 4.62 (d, J=3.5 Hz, 1H), 4.08 (d, J=9.0 Hz, 1H), 2.99-2.89 (m, 1H), 2.63 (q, J=7.0 Hz, 2H), 2.39-2.29 (m, 1H), 1.69-1.59 (m, 1H), 1.37 (sext, J=7.5 Hz, 2H), 0.80 (t, J=7.5 Hz, 3H)

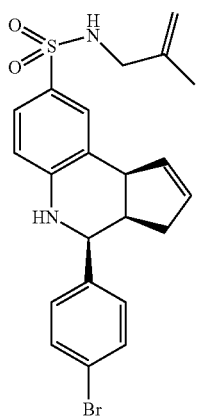 [SMILES: C=C(C)CNS(=O)(=O)c1ccc2c(c1)[C@H]1C=CC[C@H]1[C@@H](c1ccc(Br)cc1)N2]

4-(4-bromophenyl)-N-(2-methylallyl)-3a,4,5,9b-tetrahydro-3H-cyclopenta[c]quinoline-8-sulfonamide (GAT1320; 108)

H NMR (500 MHz, DMSO-d6) δ 7.56 (d, J=2.0 Hz, 1H), 7.29 (dd, J=8.5 Hz, 2.0 Hz, 1H), 7.10 (t, J=6.5 Hz, 1H), 6.98 (s, 1H), 6.73 (s, 1H), 6.69 (d, J=8.5 Hz, 1H), 5.94-5.87 (m, 1H), 5.79-5.72 (m, 1H), 4.27 (d, J=10.5 Hz, 1H), 3.99-3.93 (m, 1H), 2.98-2.88 (m, 1H), 2.64 (q, J=6.5 Hz, 2h), 2.35 (s, 3H), 2.23-2.14 (m, 1H), 2.22 (s, 3H), 2.17 (s, 3H), 2.11 (s, 3H), 1.75 (d, J=16.5 Hz, 1H), 1.39 (sextet, J=7.0 Hz, 2H), 0.82 (t, J=6.5 Hz, 3H)

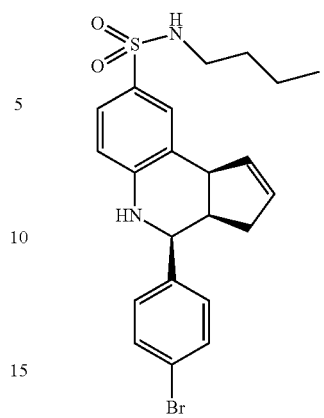

4-(4-bromophenyl)-N-butyl-3a,4,5,9b-tetrahydro-3H-cyclopenta[c]quinoline-8-sulfonamide (GAT1322; 110)

$^1$H NMR (500 MHz, DMSO-d6) δ 7.59 (d, J=8.5 Hz, 2H), 7.41 (d, J=9.0 Hz, 2H), 7.38 (d, J=1.5 Hz, 1H), 7.29 (dd, J=9.0 Hz, 2.5 Hz, 1H), 7.11 (t, J=6.5 Hz, 1H), 6.81 (d, J=8.5 Hz, 1H), 6.46 (s, 1H), 5.91-5.85 (m, 1H), 5.61 (d, J=5.5 Hz, 1H), 4.64 (d, J=3.0 Hz, 1H), 4.07 (d, J=8.5 Hz, 1H), 2.98-2.88 (m, 1H), 2.34 (ddq, J=16.0 Hz, 9.5 Hz, 2.0 Hz, 1H), 1.62 (dd, J=15.0 Hz, 9.0 Hz, 1H)

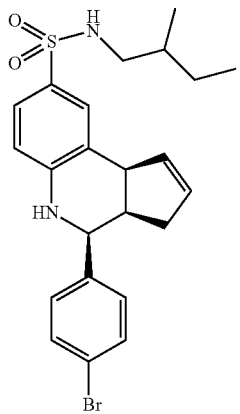 [SMILES: CCC(C)CNS(=O)(=O)c1ccc2c(c1)[C@H]1C=CC[C@H]1[C@@H](c1ccc(Br)cc1)N2]

4-(4-bromophenyl)-N-(2-methylbutyl)-3a,4,5,9b-tetrahydro-3H-cyclopenta[c]quinoline-8-sulfonamide (GAT1321; 109)

$^1$H NMR (500 MHz, DMSO-d6) δ 7.58 (d, J=8.5 Hz, 2H), 7.41 (d, J=9.0 Hz, 2H), 7.38 (d, J=2.0 Hz, 1H), 7.29 (dd, J=8.5 Hz, 2.0 Hz, 1H), 7.12 (td, J=6.5 Hz, 2.0 Hz, 1H), 6.81 (d, J=9.0 Hz, 1H), 6.44 (s, 1H), 5.91-5.84 (m, 1H), 5.64-5.57 (m, 1H), 4.64 (d, J=3.0 Hz, 1H), 4.08 (d, J=9.0 Hz, 1H), 2.98-2.89 (m, 1H), 2.61-2.52 (m, 1H), 2.50-2.42 (m, 1H), 2.39-2.32 (m, 1H), 1.69-1.60 (m, 1H), 1.45-1.28 (m, 2H), 1.08-0.98 (m, 1H), 0.83-0.74 (m, 6H)

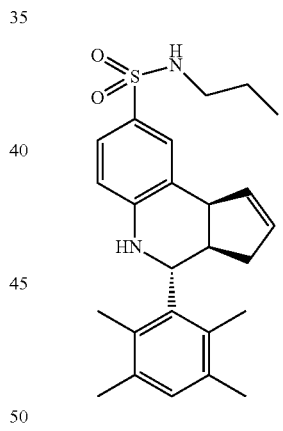

N-propyl-4-(2,3,5,6-tetramethylphenyl)-3a,4,5,9b-tetrahydro-3H-cyclopenta[c]quinoline-8-sulfonamide (GAT1323; 111)

$^1$H NMR (500 MHz, DMSO-d6) δ 7.56 (d, J=2.0 Hz, 1H), 7.29 (dd, J=8.5 Hz, 2.0 Hz, 1H), 7.10 (t, J=6.5 Hz, 1H), 6.98 (s, 1H), 6.73 (s, 1H), 6.69 (d, J=8.5 Hz, 1H), 5.94-5.87 (m, 1H), 5.79-5.72 (m, 1H), 4.27 (d, J=10.5 Hz, 1H), 3.99-3.93 (m, 1H), 2.98-2.88 (m, 1H), 2.64 (q, J=6.5 Hz, 2h), 2.35 (s, 3H), 2.23-2.14 (m, 1H), 2.22 (s, 3H), 2.17 (s, 3H), 2.11 (s, 3H), 1.75 (d, J=16.5 Hz, 1H), 1.39 (sextet, J=7.0 Hz, 2H), 0.82 (t, J=6.5 Hz, 3H)

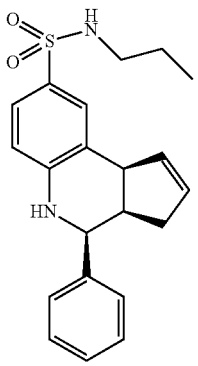 [SMILES: CCCNS(=O)(=O)c1ccc2c(c1)[C@H]1C=CC[C@H]1[C@@H](c1ccccc1)N2]

4-phenyl-N-propyl-3a,4,5,9b-tetrahydro-3H-cyclopenta[c]quinoline-8-sulfonamide (GAT1324; 112)

$^1$H NMR (500 MHz, DMSO-d6) δ 7.45 (d, J=7.5 Hz, 2H), 7.43-7.35 (m, 3H), 7.31 (d, J=7.0 Hz, 1H), 7.28 (d, J=8.5 Hz, 2.5 Hz, 1H), 7.13 (t, J=6.0 Hz, 1H), 6.82 (d, J=8.5 Hz, 1H), 6.45 (s, 1H), 5.92-5.84 (m, 1H), 5.62 (d, J=5.0 Hz, 1H), 4.65 (d, J=3.0 Hz, 1H), 4.08 (d, J=8.5 Hz, 1H), 3.00-2.90 (m, 1H), 2.63 (q, J=7.5 Hz, 1H), 2.45-2.34 (m, 1H), 1.68-1.58 (m, 1H), 1.36 (sextet, J=7.5 Hz, 2H), 0.80 (t, J=7.5 Hz, 3H)

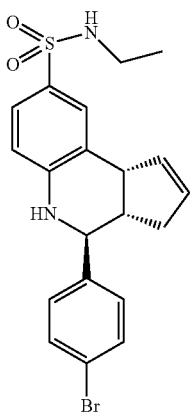 [SMILES: CCNS(=O)(=O)c1ccc2c(c1)[C@@H]1C=CC[C@@H]1[C@@H](c1ccc(Br)cc1)N2]

(4-(4-bromophenyl)-N-ethyl-3a,4,5,9b-tetrahydro-3H-cyclopenta[c]quinoline-8-sulfonamide (GAT1325; 113)

$^1$H NMR (500 MHz, DMSO-d6) δ 7.59 (d, J=8.5 Hz, 2H), 7.55 (d, J=2.0 Hz, 1H), 7.39 (d, J=8.0 Hz, 2H), 7.32 (dd, J=8.5 Hz, 2.0 Hz, 1H), 7.11 (t, J=6.0 Hz, 1H), 6.75 (d, J=8.0 Hz, 1H), 6.64 (s, 1H), 5.92-5.85 (m, 1H), 5.77-5.70 (m, 1H), 3.96-3.88 (m, 1H), 3.65 (d, J=9.5 Hz, 1H), 2.77-2.67 (m, 2H), 2.62-2.53 (m, 1H), 2.46-2.35 (m, 1H), 1.99 (d, J=16.5 Hz, 1H), 0.96 (t, J=7.5 Hz, 3H)

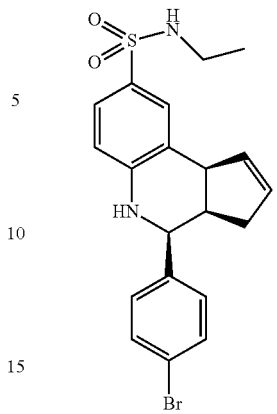

(4-(4-bromophenyl)-N-ethyl-3a,4,5,9b-tetrahydro-3H-cyclopenta[c]quinoline-8-sulfonamide (GAT1326; 114)

$^1$H NMR (500 MHz, DMSO-d6) δ 7.59 (d, J=8.5 Hz, 2H), 7.41 (d, J=9.0 Hz, 2H), 7.29 (dd, J=9.0 Hz, 2.5 Hz, 1H), 7.11 (t, J=6.0 Hz, 1H), 6.82 (d, J=8.5 Hz, 1H), 6.47 (s, 1H), 5.92-5.84 (m, 1H), 5.61 (d, J=5.5 Hz, 1H), 4.64 (d, J=9.5 Hz, 1H), 2.98-2.88 (m, 1H), 2.75 (2.66 (m, 2H), 2.39-2.29 (m, 1H), 1.69-1.59 (m, 1H), 0.96 (t, J=7.0 Hz, 3H)

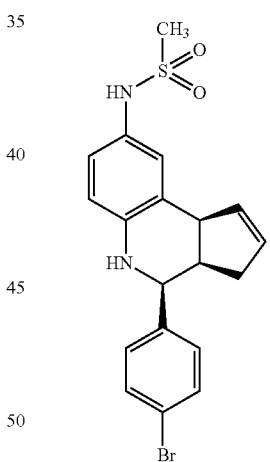

N-(4-(4-bromophenyl)-3a,4,5,9b-tetrahydro-3H-cyclopenta[c]quinolin-8-yl)methanesulfonamide (GAT1327; 115)

$^1$H NMR (500 MHz, DMSO-d6) δ 9.04 (s, 1H), 7.57 (d, J=9.0 Hz, 2H), 7.41 (d, J=9.0 Hz, 2H), 6.86 (d, J=2.0 Hz, 1H), 6.78 (dd, J=8.0 Hz, 2.5 Hz, 1H), 6.70 (d, J=8.5 Hz, 1H), 5.84-5.77 (m, 1H), 5.69 (s, 1H), 5.59 (d, J=4.5 Hz, 1H), 4.50 (d, J=3.0 Hz, 1H), 4.01 (d, J=8.5 Hz, 1H), 2.96-2.84 (m, 1H), 2.85 (s, 1H), 2.43-2.32 (m, 1H), 1.62 (dd, J=16.0 Hz, 9.0 Hz, 1H)

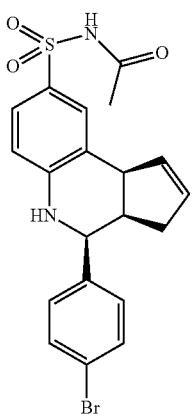 [SMILES: CC(=O)NS(=O)(=O)c1ccc2c(c1)[C@H]1C=CC[C@H]1[C@@H](c1ccc(Br)cc1)N2]

N-((4-(4-bromophenyl)-3a,4,5,9b-tetrahydro-3H-cyclopenta[c]quinolin-8-yl)sulfonyl)acetamide (GAT1328; 116)

1H NMR (500 MHz, DMSO-d6) δ 11.97 (s, 1H), 7.59 (d, J=8.5 Hz, 2H), 7.48 (d, J=2.0 Hz, 1H), 7.42 (dd, J=8.5 Hz, 2.5 Hz, 1H), 7.40 (d, J=8.5 Hz, 2H), 6.82 (d, J=8.5 Hz, 1H), 6.69 (s, 1H), 5.92-5.84 (m, 1H), 5.65-5.58 (m, 1H), 4.67 (d, J=3.5 Hz, 1H), 4.08 (d, J=9.0 Hz, 1H), 2.99-2.88 (m, 1H), 2.38-2.26 (m, 1H), 1.69-1.58 (m, 1H)

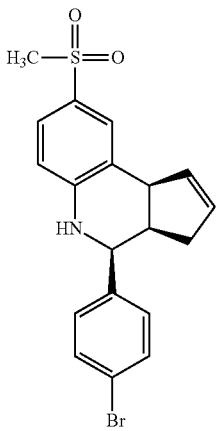 [SMILES: CS(=O)(=O)c1ccc2c(c1)[C@H]1C=CC[C@H]1[C@@H](c1ccc(Br)cc1)N2]

4-(4-bromophenyl)-8-(methylsulfonyl)-3a,4,5,9b-tetrahydro-3H-cyclopenta[c]quinolone (GAT1329; 117)

1H NMR (500 MHz, DMSO-d6) δ 7.59 (d, J=8.5 Hz, 2H), 7.50 (d, J=2.0 Hz, 1H), 7.41 (d, J=9.0 Hz, 2H), 7.40 (dd, J=8.5 Hz, 2.5 Hz, 1H), 6.86 (d, J=9.0 Hz, 1H), 6.65 (s, 1H), 6.00-5.92 (m, 1H), 5.61 (d, J=5.5 Hz, 1H), 4.67 (d, J=3.5, 1H), 4.09 (d, J=8.0 Hz, 1H), 3.07 (s, 3H), 3.00-2.88 (m, 1H), 2.38-2.27 (m, 1H), 1.69-1.59 (m, 1H)

Example 3. Modulation of Ionic Currents of Alpha-7 Nicotinic Acetylcholine Receptor Expressed in *Xenopus* Oocytes cDNA Clones and RNA The human alpha-7 nAChR receptor clone was obtained from Dr. Jon Lindstrom {University of Pennsylvania, Philadelphia, Pa.), aid the RIC-3 clone from Dr. Millet Treinin (Hebrew University, Jerusalem, Israel) for the purpose of co-injection with a7 to improve the level and speed of receptor expression (Halevi et al., 2003). After linearization and purification of cloned cDNA's, RNA, transcripts were prepared rising the appropriate mMessage mMachine kit tiom Ambion (Austin, Tex.).

Expression in *X, laeivis* Oocytes

Oocytes were obtained from mature (>9 cm) female *Xenopus laeivis* African frogs (Nasco, Ft. Atkinson, Wis.). Frogs were anesthetized in 0.7 g/L solution of ethyl 3-aminobenzoate methanesulfonate buffered with sodium bicarbonate, and oocytes were surgically removed through an abdominal incision. Harvested oocytes were treated with 1.25 mg/ml collagenase (Worthington Biochemicals, Freehold, N.J.) in calcium-free Barth's solution (88 mM NaCl, 1 mM KCl, 2.38 mM NaHCO$_3$, 0.82 mM MgSO$_4$, 15 mM HEPES, 12 mg/L tetracycline, pH 7.6) for 3-4 hours to remove the follicular layer. Stage-5 oocytes were isolated and injected with 50 nL (5-20 ng) of human alpha-7 and RIC-3 cRNA. Suitable levels of receptor expression were typically achieved 2-6 days after injection of cRNA. For experiments involving the PAM 4BP-TQS/GAT-107, where standard levels of expression result in ion currents too large to be recorded in voltage clamp, experiments were typically conducted 1-3 days after RNA injection.

Electrophysiology

Two-electrode voltage clamp experiments were conducted using OpusXpress6000A (Molecular Devices, Sunnyvale, Calif.), an integrated system that provides automated impalement and voltage clamp of up to eight oocytes in parallel. Both the current and voltage electrodes were filled with 3 M KCl, and oocytes were clamped at a holding potential of −60 mV. Data were collected at 50 Hz and filtered at 20 Hz. The oocytes were bath-perfused with Ringer's solution (115 mM NaCl, 10 mM HEPES, 2.5 mM KCl, 1.8 mM CaCl$_2$, pH 7.3), and agonist solutions were delivered from a 96-well drug plate using disposable tips. Flow rates were set at 2 mL/min, with each drug or control solution delivered in 12 s durations, followed~by 181 s washouts with Ringer's unless noted otherwise.

Experimental Protocols and Data Analysis

Responses of human alpha-7 receptors to agonists were measured as both peek current and net charge measured over a 120 s period beginning with the compound application (Papke and Papke, 2002). Note that for data obtained in the absence of PAMs, net charge data are a more reliable measurement of response since the fast desensitization, characteristic of a7, results in the peak current being reached before agonist solution exchange is complete, giving values which do not correspond to activation produced by the ligand at the final concentration applied. In experiments involving positive allosteric modulators (PAMs), the fast desensitization of alpha-7 was eliminated, allowing peak currents to be used as a valid measurement of the receptor-mediated responses (Wang et al., 2012; Williams et al., 2011).

Oocytes received two control ACh applications prior to receiving any drug in order to establish a steady reference response, and they received one or more control ACh applications at the end of all experiments. For experiments involving drug incubation through bath applications, all responses were normalized to the average of two ACh control responses taken immediately prior to the switch of bath solution, for each cell individually. These normalization procedures had the effect of compensating for differing levels of receptor expression among the multiple oocytes used in each experiment. Each experiment was conducted on at least four oocytes, with mean values and standard errors (S.E.M.) calculated from their normalized responses.

For concentration-response relations, data were plotted using Kaleidagraph 3.0.2 (Abelbeck/Synergy, Reading, Pa.}. Curves were generated using the Hill equation:

$$\text{Response} = I_{max}[\text{agonist}]^n / ([\text{agonist}]^n + (EC_{50})^n)$$

where $I_{max}$ denotes the maximal response for a particular agonist/subunit pair, and n represents the Hill coefficient.

$I_{max}$, n, $EC_{50}$, and $IC_{50}$ were all unconstrained for the fitting procedures. For inhibition (RID) curves, the initial $I_{max}$ was constrained to I and the Hill slope fit to a negative value.

The results are shown in the table below. "Charge" indicates the area under the curve of current vs. time. "Alone" refers to the charge obtained from the compound alone acting as an allosteric agonist; compounds producing current are ago-PAMs. "+C" refers to the charge obtained in the presence of the compound together with choline or ACh; this includes PAM activity as well as ago-PAM activity.

| Compound | R2 | R1 | A | D | Charge Alone | +C |
|---|---|---|---|---|---|---|
| 1 GAT107 | 4-bromo phenyl | 4-$SO_2NH_2$ | CH | CH | 450 | 1700 |
| 2 GAT108 | 4-pyridyl | 4-$SO_2NH_2$ | CH | CH | Inactive | Inactive |
| 3 GAT110 | 4-bromo phenyl | 4-$SO_2NH_2$ | O | $CH_2$ | Inactive | Inactive |
| 4 GAT111 | 4-sulfamoyl phenyl | 4-Br | CH | CH | 0 | 8.4 |
| 5 GAT112 | 4-bromo phenyl | 4-$SO_2NH_2$ | $CH_2$ | $CH_2$ | 23 | 93 |
| 6 GAT114 (trans) | 4-cyano phenyl | 4-$SO_2NH_2$ | CH | CH | Inactive | Inactive |
| 7 GAT116 | 4-cyano phenyl | 4-$SO_2NH_2$ | CH | CH | 0 | 248 |
| 8 GAT117 | 4-nitro phenyl | 4-$SO_2NH_2$ | CH | CH | 43 | 318 |
| 9 GAT118 | 4-bromo phenyl | 4-$CONH_2$ | CH | CH | Inactive | Inactive |
| 10 GAT119 | 4-bromo phenyl | 3-$SO_2NH_2$ | CH | CH | Inactive | Inactive |
| 11 GAT120 | 4-bromo phenyl | 2-$SO_2NH_2$ | CH | CH | Inactive | Inactive |
| 12 GAT122 | 4-biphenyl | 4-$SO_2NH_2$ | CH | CH | Inactive | 76 |
| 13 GAT123 | Phenacetyl | 4-$SO_2NH_2$ | CH | CH | Inactive | 76 |
| 14 GAT124 | 3-furaldehyde | 4-$SO_2NH_2$ | CH | CH | Inactive | Inactive |
| 15 GAT125 | thiophene-3-yl | 4-$SO_2NH_2$ | CH | CH | Inactive | 500 |
| 16 GAT127 | 4-tert-butyl phenyl | 4-$SO_2NH_2$ | CH | CH | Inactive | Inactive |
| 17 GAT130 | thiophene-3-yl | 4-$SO_2NH_2$ | CH | CH | 0.031 | 21.096 |
| 18 GAT133 | 4-amino phenyl | 4-$SO_2NH_2$ | CH | CH | Inactive | 250 |
| 19 GAT134 | cyclohexane | 4-$SO_2NH_2$ | CH | CH | Inactive | Inactive |
| 20 GAT136 | 2-nitro phenyl | 4-$SO_2NH_2$ | CH | CH | Inactive | 52 |
| 21 GAT138 | 4-bromo phenyl | 4-(N,N dimethyl sulfamoyl) phenyl | CH | CH | Inactive | Inactive |
| 22 GAT139 | 4-bromo phenyl | 4-(N methyl sulfamoyl) phenyl | CH | CH | Inactive | Inactive |
| 23 GAT140 | 4-bromo phenyl | 4-morpholino sulfonyl) phenyl | CH | CH | Inactive | Inactive |
| 24 GAT141 | 4-((tert-butoxycarbonyl) amino) phenyl | 4-$SO_2NH_2$ | CH | CH | 212 | 580 |
| 25 GAT143 | p-$N_3$ | 4-$SO_2NH_2$ | CH | CH | 61 | 764 |
| 26 GAT144 | p-NCS | 4-$SO_2NH_2$ | CH | CH | 0 | 22 |
| 27 GAT145 | 4-bromo phenyl | 4-(pyrrolidin-1-ylsulfonyl) | CH | CH | Inactive | Inactive |
| 28 GAT146 | 4-$SO_2NH_2$ | 4-$SO_2NH_2$ | CH | CH | Inactive | 128 |

-continued

| Compound | R2 | R1 | A | D | Charge Alone | +C |
|---|---|---|---|---|---|---|
| 29 GAT147 | 2,4-dichloro phenyl | 4-COOH | CH | CH | Inactive | Inactive |
| 30 GAT148 | 6-bromobenzo[d][1,3]dioxol-5-yl phenyl | 4-acetyl | CH | CH | Inactive | Inactive |
| 31 GAT149 | 4-(pentafluoro-$\lambda,^6$-sulfanyl) phenyl | 4-$SO_2NH_2$ | CH | CH | 89 | 206 |
| 32 GAT150 | 4-bromo phenyl | 4-amino-N-cyclopropyl-benzenesulfonamide | CH | CH | Inactive | Inactive |
| 33 GAT151 | 4-H | 4-$SO_2NH_2$ | CH | CH | Inactive | Inactive |
| 34 GAT152 | 5-cyano thiophene-2-yl | 4-$SO_2NH_2$ | CH | CH | Insoluble | Insoluble |
| 35 GAT153 | 5-bromo thiophene-3-yl | 4-$SO_2NH_2$ | CH | CH | Inactive | 157 |
| 36 GAT154 | 5-bromo thiophene-2-yl | 4-$SO_2NH_2$ | CH | CH | 48 | 1145 |
| 37 GAT155 | 4-bromo thiophene-2-yl | 4-$SO_2NH_2$ | CH | CH | 0 | 163 |
| 38 GAT156 | 3,4-dibromo thoiphene-2-yl | 4-$SO_2NH_2$ | CH | CH | 18 | 1246 |
| 39 GAT157 | benzo[b]thiophen-3-yl | 4-$SO_2NH_2$ | CH | CH | 22 | 145 |
| 40 GAT158 | 4-bromo phenyl | 4-COOH | CH | CH | Inactive | Inactive |
| 41 GAT159 | benzo[b]thiophen-2-yl | 4-$SO_2NH_2$ | CH | CH | 3 | 528 |
| 42 GAT160 | Pentafluoro phenyl | 4-$SO_2NH_2$ | CH | CH | Inactive | 47 |
| 43 GAT161 | Tetrafluoro azide | 4-$SO_2NH_2$ | CH | CH | Inactive | 5.5 |
| 44 GAT162 | Trifluoromethyl diazirene | 4-$SO_2NH_2$ | CH | CH | 14 | 350 |
| 45 GAT163 (−) enantiomer of GAT142 | 4-I | 4-$SO_2NH_2$ | CH | CH | Inactive | Inactive |
| 46 GAT164 (+) enantiomer of GAT142 | 4-I | 4-$SO_2NH_2$ | CH | CH | 242 | 684 |
| 47 GAT165 (−) enantiomer of GAT143 | 4-$N_3$ | 4-$SO_2NH_2$ | CH | CH | Inactive | Inactive |
| 48 GAT166 (+) enantiomer of GAT143 | 4-$N_3$ | 4-$SO_2NH_2$ | CH | CH | 61 | 764 |
| 49 GAT167 | Ph—O—Ph | 4-$SO_2NH_2$ | CH | CH | N/A | N/A |
| 50 GAT168 | Ph—O—$CH_2$—Ph | 4-$SO_2NH_2$ | CH | CH | 20 | 67 |
| 51 GAT169 | 3-pyridinyl | 4-$SO_2NH_2$ | CH | CH | Inactive | 10 |
| 52 GAT170 | 2-pyridinyl | 4-$SO_2NH_2$ | CH | CH | Inactive | 4 |
| 53 GAT171 | 4-bromo-2-naphthyl | 4-$SO_2NH_2$ | CH | CH | Inactive | 76 |
| 54 GAT173 | 4-bromo phenyl | 4-(azitidin-1-ylsulfonyl) | CH | CH | Inactive | Inactive |
| 55 GAT174 | 4-bromo phenyl | 4-amino-N,N-diethylbenzene-sulfonamide | CH | CH | Inactive | Inactive |
| 56 GAT176 (−) enantiomer of GAT145 | 4-bromo phenyl | 4-(pyrrolidin-1-ylsulfonyl) | CH | CH | Inactive | Inactive |
| 57 GAT177 (+) enantiomer of GAT145 | 4-bromo phenyl | 4-(pyrrolidin-1-ylsulfonyl) | CH | CH | Inactive | Inactive |

-continued

| Compound | R2 | R1 | A | D | Charge Alone | +C |
|---|---|---|---|---|---|---|
| 58 GAT180 | 4-benzoic acid | 4-SO$_2$NH$_2$ | CH | CH | Inactive | Inactive |
| 59 GAT181 | methyl (4-formylphenyl) carbamate | 4-SO$_2$NH$_2$ | CH | CH | Inactive | 480 |
| 60 GAT182 | ethyl (4-formylphenyl) carbamate | 4-SO$_2$NH$_2$ | CH | CH | Inactive | 276 |
| 61 GAT183 | cyclohexyl (4-formylphenyl) carbamate | 4-SO$_2$NH$_2$ | CH | CH | Inactive | 85 |
| 62 GAT184 | Adamantan-1-yl (4-formylphenyl) carbamate | 4-SO$_2$NH$_2$ | CH | CH | Inactive | 35 |
| 63 GAT185 | Adamantan-2-yl (4-formylphenyl) carbamate | 4-SO$_2$NH$_2$ | CH | CH | 5 | 25 |
| 64 GAT186 | N-(4-formylphenyl)-3,3-dimethyl butanamide | 4-SO$_2$NH$_2$ | CH | CH | 597 | 652 |
| 65 GAT187 | 4-formylphenyl tert-butyl carbamate | 4-SO$_2$NH$_2$ | CH | CH | 332 | 740 |
| 66 GAT188 | 4-(4,4-dimethylpentyl) benzaldehyde | 4-SO$_2$NH$_2$ | CH | CH | 330 | 1240 |
| 67 GAT189 | 2,5-dibromothiophene-3-carbaldehyde | 4-SO$_2$NH$_2$ | CH | CH | Inactive | 100 |
| 68 GAT190 | isopropyl (4-formylphenyl) carbamate | 4-SO$_2$NH$_2$ | CH | CH | 80 | 156 |
| 69 GAT191 | 4-formylphenyl 3,3-dimethyl butanoate | 4-SO$_2$NH$_2$ | CH | CH | 25 | 582 |
| 70 GAT192 | neopentyl 4-formylbenzoate | 4-SO$_2$NH$_2$ | CH | CH | 52 | 487 |
| 71 GAT193 | 4-(3-bromopropyl) benzaldehyde | 4-SO$_2$NH$_2$ | CH | CH | 1 | 284 |
| 72 GAT900 | 1-bromo-2-fluoro benzaldehyde | 4-SO$_2$NH$_2$ | CH | CH | N/A | N/A |
| 73 GAT901 | 5-nitrothiophene-2-carbaldehyde | 4-SO$_2$NH$_2$ | CH | CH | N/A | N/A |
| 74 GAT902 | 4-((trifluoromethyl) thio)benzaldehyde | 4-SO$_2$NH$_2$ | CH | CH | N/A | N/A |
| 75 GAT903 | 4-bromo-furan-2-carbaldehyde | 4-SO$_2$NH$_2$ | CH | CH | N/A | N/A |
| 76 GAT904 | 4-(bromomethyl) benzaldehyde | 4-SO$_2$NH$_2$ | CH | CH | N/A | N/A |
| 77 GAT905 | 3-bromothiophene-2-carbaldehyde | 4-SO$_2$NH$_2$ | CH | CH | N/A | N/A |
| 78 GAT906 | 4-bromo-2-fluoro benzaldehyde | 4-SO$_2$NH$_2$ | CH | CH | N/A | N/A |
| 79 GAT907 | 2-(4-bromophenyl) acetaldehyde | 4-SO$_2$NH$_2$ | CH | CH | N/A | N/A |
| 80 GAT908 | 4-bromo-2,6-difluoro benzaldehyde | 4-SO$_2$NH$_2$ | CH | CH | N/A | N/A |
| 81 GAT909 | 4-bromo-2,6-dimethyl benzaldehyde | 4-SO$_2$NH$_2$ | CH | CH | N/A | N/A |
| 82 GAT910 | 5-chlorothiophene-2-carbaldehyde | 4-SO$_2$NH$_2$ | CH | CH | N/A | N/A |
| 83 GAT911 | Benzaldehyde | 4-SO$_2$NH$_2$ | CH | CH | N/A | N/A |
| 84 GAT912 (trans) | 4-bromo benzaldehyde | 4-amino-3-fluorobenzene-sulfonamide | CH | CH | N/A | N/A |
| 85 GAT913 | 2-bromothiazole-4-carbaldehyde | 4-SO$_2$NH$_2$ | CH | CH | 10 | 166 |
| 86 GAT914 | 4-bromo benzaldehyde | 4-amino-3-fluorobenzene-sulfonamide | CH | CH | N/A | N/A |

|  |  |  |  |  | Charge | |
|---|---|---|---|---|---|---|
| Compound | R2 | R1 | A | D | Alone | +C |
| 87 GAT915 (trans) | 5'-bromo-[2,2'-bithiophene]-5-carbaldehyde | 4-SO$_2$NH$_2$ | CH | CH | N/A | N/A |
| 88 GAT916 | 5'-bromo-[2,2'-bithiophene]-5-carbaldehyde | 4-SO$_2$NH$_2$ | CH | CH | N/A | N/A |
| 89 GAT917 | 1,3-dibromo phenyl | 4-SO$_2$NH$_2$ | CH | CH | N/A | N/A |
| 90 GAT918 (trans) | 5-phenylthiophene-2-carbaldehyde | 4-SO$_2$NH$_2$ | CH | CH | N/A | N/A |
| 91 GAT919 | thiazole-2-carbaldehyde | 4-SO$_2$NH$_2$ | CH | CH | N/A | N/A |
| 92 GAT920 | benzo[b]thiophene-7-carbaldehyde | 4-SO$_2$NH$_2$ | CH | CH | N/A | N/A |
| 93 GAT921 | thieno[3,2-b]thiophene-2-carbaldehyde | 4-SO$_2$NH$_2$ | CH | CH | N/A | N/A |
| 94 GAT922 | 6-bromonicotin aldehyde | 4-SO$_2$NH$_2$ | CH | CH | 29 | 348 |
| 95 GAT923 | 3-chlorobenzo[b]thiophene-2-carbaldehyde | 4-SO$_2$NH$_2$ | CH | CH | N/A | N/A |
| 96 GAT924 | benzo[b]thiophene-5-carbaldehyde | 4-SO$_2$NH$_2$ | CH | CH | 116 | 156 |
| 97 GAT925 | 5-bromopicolin aldehyde | 4-SO$_2$NH$_2$ | CH | CH | 7 | 357 |
| 98 GAT926 | 4-(thiophen-3-yl)benzaldehyde | 4-SO$_2$NH$_2$ | CH | CH | N/A | N/A |
| 99 GAT928 | 4-bromo benzaldehyde | 4-SO$_2$NH$_2$ | C—CH$_3$ | CH | N/A | N/A |
| 100 GAT1308 | 4-bromo benzaldehyde | 4-amino-N-isopropylbenzene-sulfonamide | CH | CH | Inactive | Inactive |
| 101 GAT1309 | 4-bromo benzaldehyde | 4-amino-N-(tert-butyl)benzene-sulfonamide | CH | CH | Inactive | Inactive |
| 102 GAT1310 | 4-bromo benzaldehyde | 4-amino-N-cyclohexyl-benzenesulfonamide | CH | CH | Inactive | Inactive |
| 103 GAT1311 | 4-bromo benzaldehyde | 4-amino-N-phenylbenzene-sulfonamide | CH | CH | Inactive | Inactive |
| 104 GAT1312 | 4-bromo benzaldehyde | 4-amino-N-cyclobutyl-benzenesulfonamide | CH | CH | Inactive | Inactive |
| 105 GAT1314 | 4-bromo benzaldehyde | 4-amino-N-(cyclopropyl methyl)benzene-sulfonamide | CH | CH | Inactive | Inactive |
| 106 GAT1318 (trans) | 4-bromo benzaldehyde | 4-amino-N-propylbenzene-sulfonamide | CH | CH | Inactive | Inactive |
| 107 GAT1319 | 4-bromo benzaldehyde | 4-amino-N-propylbenzene-sulfonamide | CH | CH | Inactive | Inactive |
| 108 GAT1320 | 4-bromo benzaldehyde | 4-amino-N-(2-methylallyl) benzenesulfonamide | CH | CH | Inactive | Inactive |
| 109 GAT1321 | 4-bromo benzaldehyde | 4-amino-N-(2-methylbutyl) benzenesulfonamide | CH | CH | Inactive | Inactive |
| 110 GAT1322 | 4-bromo benzaldehyde | 4-amino-N-butylbenzene sulfonamide | CH | CH | Inactive | Inactive |
| 111 GAT1323 (trans) | 2,3,5,6-tetramethyl benzaldehyde | 4-amino-N-propylbenzene-sulfonamide | CH | CH | Inactive | Inactive |
| 112 GAT1324 | benzaldehyde | 4-amino-N-propylbenzene-sulfonamide | CH | CH | Inactive | Inactive |
| 113 GAT1325 (trans) | 4-bromo benzaldehyde | 4-amino-N-ethylbenzene sulfonamide | CH | CH | Inactive | Inactive |

| Compound | R2 | R1 | A | D | Charge Alone | +C |
|---|---|---|---|---|---|---|
| 114 GAT1326 | 4-bromo benzaldehyde | 4-amino-N-ethylbenzene sulfonamide | CH | CH | Inactive | Inactive |
| 115 GAT1327 | 4-bromo benzaldehyde | N-(4-aminophenyl) methanesulfonamide | CH | CH | Inactive | Inactive |
| 116 GAT1328 | 4-bromo benzaldehyde | N-((4-aminophenyl) sulfonyl)acetamide | CH | CH | Inactive | Inactive |
| 117 GAT1329 | 4-bromo benzaldehyde | 4-(methylsulfo-nyl)aniline | CH | CH | Inactive | Inactive |

Results:

The active compounds shown in the above table typically had three kinds of activities: a) direct activation, where the ligand bound to the allosteric site of the receptor and activated the receptor on its own; b) direct potentiation, where the ligand bound to the allosteric site of the receptor and enhanced the activity of the orthosteric ligand, but did not have any effect on its own; and c) primed potentiation, where the ligand modified the conformation of the receptor temporarily and kept it in an active state (sensitized state) for a longer time. The compounds that acted as positive allosteric modulators (PAMs) of the alpha-7 receptor increased the activity of the orthosteric ligands, some of them increasing it several fold. Compounds that induced both positive allosteric modulation and allosteric agonism (ago-PAMs, having activity when administered alone) were detected as well.

A significant discovery was with GAT141, a compound with an extended southern chain in the form a Boc protecting group. This compound showed increased 'ago' component suggesting that there is a secondary southern pocket present on the receptor which can be filled by linear alkyl chains with or without heteroatoms. With GAT168, the presence of a phenyl ring instead of a functionalized alkyl chain was also tolerated and led to moderate ago-PAM activity. This finding led to a series of molecules with comparatively stronger allosteric agonist ("ago") or positive alosteric modulation ("PAM") components.

Example 4. Electrophysiological Evaluation of Alpha-7 nAChR PAMs and Ago-PAMs

Electrophysiological evaluation in *Xenopus* oocytes was used to determine the potency and efficacy with which PAMs and ago-PAMs of the invention produce self-induced agonism and positive allosteric modulation of the orthosteric, agonist-induced activation of the alpha-7 nAChR. The ability of these compounds to increase the maximal channel influx and to enhance the activity of the receptor on its own as well as in presence of choline is denoted by $I_{max}$ and $EC_{50}$ respectively. The details of cDNA clones and RNA for injection was as published. Thakur et. al. 2013, J. Med. Chem. 2013 Nov. 14; 56(21):8943-7. doi: 10.1021/jm401267t). For experiments involving PAM and ago-PAM analogs, where standard levels of expression result in ion currents too large to be recorded in voltage clamp, experiments were typically conducted 1-3 days after RNA injection.

Two-electrode voltage clamp was conducted using OpusXpress 6000A (Molecular Devices, Union City, Calif.). Both the voltage and current electrodes were filled with 3 M KCl. Oocytes were voltage-clamped at −60 mV except when determining the effect of voltage on channel activation. The oocytes were bath-perfused with Ringer's solution (115 mM NaCl, 2.5 mM KCl, 1.8 mM $CaCl_2$, 10 mM HEPES, and 1 µM atropine, pH 7.2) with a flow rate of 2 mL/min. To evaluate the effects of experimental compounds on ACh-evoked responses of alpha-7 nAChRs expressed in oocytes, the initial control responses were measured with two applications of ACh alone, before applications of experimental drugs alone or co-applications with ACh. The agonist solutions were applied from a 96-well plate via disposable tips, and the drugs were either co-applied with ACh by the OpusXpress pipette delivery system or bath-applied using the OpusXpress system to switch the running buffer. Drug applications were for 12 s followed by a 181 s washout period and usually alternated between controls and test solutions. After experimental drug applications, follow-up control applications of ACh were made to determine primed potentiation, desensitization or rundown of the receptors. Data were collected at 50 Hz, filtered at 20 Hz, analyzed by Clampfit 9.2 (Molecular Devices) and Excel (Microsoft, Redmond Wash.), and normalized to the averaged current of the two initial control responses. Data were expressed as mean±SEM from at least four oocytes for each experiment. For the concentration-response relationships, responses were normalized to the net charge of the most adjacent prior control.

A detailed comparative activity profile of select ago-PAMs/PAMs based on the structure of 4BP-TQS was obtained. The results are presented in FIGS. 2A-2F. As previously described for GAT107, when applied alone ago-PAMs (e.g. GAT154) directly activated human alpha-7 nAChR (FIGS. 2A, 2B, and 2C). Additionally, they produced large primed potentiation in the subsequent responses to ACh applied alone. They also functioned as direct PAMs, producing responses when co-applied with ACh. However, the primed potentiation of response to ACh alone was less after direct potentiation than after direct activation, due to residual induction of PAM-insensitive desensitization.

PAMs such as GAT155 produced negligible direct activation but large primed potentiation. They also functioned as direct potentiators, with reduced primed potentiation following direct potentiation (FIGS. 2A-2F). The inventors have discovered a secondary site at the southern region of the molecule (GAT141; and other representative examples with an alkyl or a functionalized chain) that greatly increased the efficacy of the molecule (FIGS. 2C, 2D, and 2E). GAT141 exhibited all three types of activities, confirming its ago-PAM nature. GAT186 and GAT187, analogs of GAT141, were more effective as allosteric agonists and almost equally effective as ago-PAMs when compared to GAT154.

The electrophysiology assays were used as a first filter for selecting molecules having efficacy and potency. Those with favorable physicochemical properties were taken ahead into animal studies to test their effects on various neurological disorders.

Example 5. Effect of PAMs and Ago-PAMs for Alpha-7 nAChR on Inflammation

A formalin test was carried out in an open plexiglas cage, with a mirror placed at a 45° angle behind the cage to allow an unobstructed view of the paws. Mice were allowed to acclimate for 15 min in the test cage prior to injection. Each animal was injected intraplantar with 20 µl of 2.5% formalin to the right hindpaw. Each mouse was then immediately placed in the test cage. Up to two mice at one time were observed during 0 to 5 min after injection (phase 1) and during 20-45 min post injection (phase 2). The period between the two phases of nociceptive responding is generally considered to be a phase of weak activity. The amount of time spent licking the injected paw was recorded with a digital stopwatch.

Further, the antinociceptive activity of drugs in phase II of the formalin test and their anti-allodynic response in the CCI model was tested. Mice received vehicle or methyllycaconatine (MLA, 10 mg/kg) prior to vehicle or an ED84 dose of the ago-PAM/PAM (determined from a dose-response experiment using the formalin intraplantar injection model). That dose of MLA was found to antagonize alpha-7 receptor mediated antinociceptive effects. The MLA results were confirmed by testing the ED84 dose of the test compounds in the alpha-7 KO and wild type mice. Finally, it was tested whether tolerance develops to the antinociceptive effects of alpha-7 nAChR ago-PAM following 7 days of repeated injections of its ED84 dose. Mice were given the following treatments: vehicle (7 days of vehicle administration); acute alpha-7 nAChR test compounds (6 days of vehicle administration followed by alpha-7 nAChR ago-PAM on the last day); and repeated alpha-7 nAChR test compounds (7 days of alpha-7 nAChR PAM or ago-PAM).

Figure 3A:
FIGS. 3A-3D show anti-inflammatory effects of agoPAM GAT107 in a mouse model of inflammatory pain.
Figure 3C:
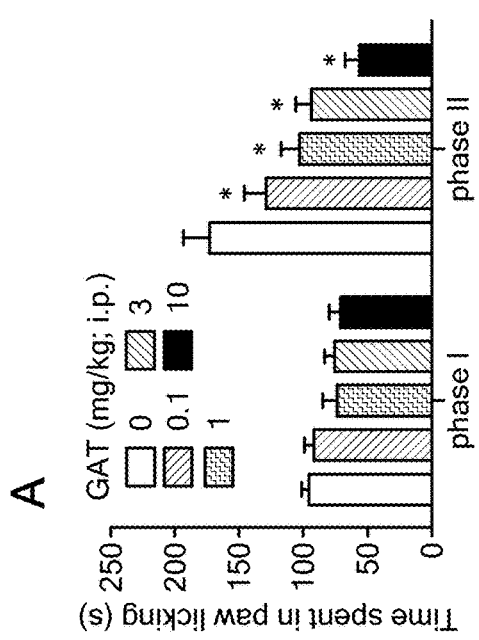
Figure 3B:
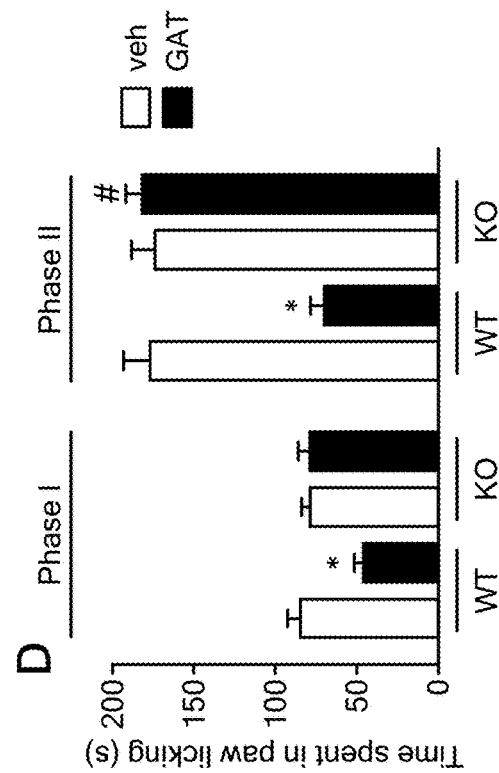
Figure 3D:
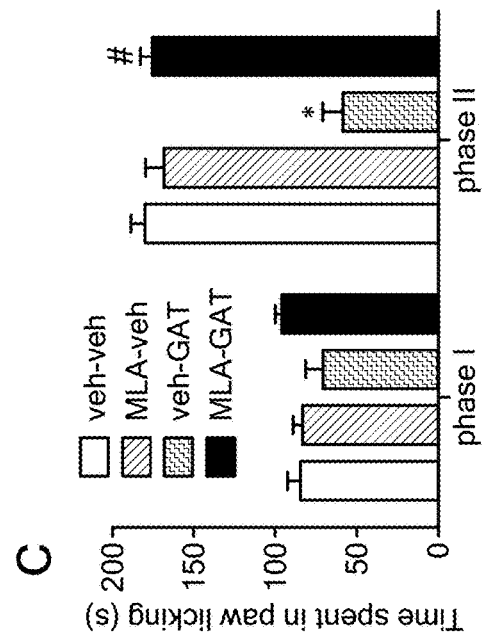

Two distinct periods of high licking activity were identified: an early phase lasting for the first 5 min and a late phase lasting from 20 to 30 min after the injection. GAT107 was found to dose-dependently and significantly block the nociceptive behavior of formalin phase II compared to phase I when given i.v. (FIG. 3A) as well as orally (FIG. 3B), and reduced the paw edema induced by formalin intraplantar injection. MLA, an inverse agonist of the alpha-7 receptor, reversed the effects of GAT107, suggesting that GAT107's activity is through the alpha-7 nAChR (see FIG. 3C). GAT107 was also inactive with alpha-7 nAChR knockout mice, confirming the role of alpha-7 receptors in its activity (FIG. 3D).

Example 6. Effect of PAMs and Ago-PAMs for Alpha-7 nAChR on Chronic Pain

Complete Freund's Adjuvant Test

Mice were injected with 20 µl of CFA (0.5 mg/ml of heat killed *Mycobacterium tuberculosis*, Sigma) in the intraplantar region of the right hindpaw. Paw diameter and thermal hyperalgesia (see paw withdrawal test) were measured 3 days after CFA injection. In separate groups of mice that received CFA, mechanical allodynia thresholds were determined according to previously published method (Ondachi et. al. J Med Chem. 2014 Feb. 13; 57(3):836-48. doi: 10.1021/jm401602p). Mice were placed in a plexiglas cage with mesh metal flooring and allowed to acclimate for 30 min before testing. A series of calibrated von Frey filaments (Stoelting, Wood Dale, Ill.) with logarithmically incremental stiffness ranging from 2.83 to 5.88 expressed as log 10 of [10 £ force in (mg)] were applied to the paw with a modified up-down method. In the absence of a paw withdrawal response to the initially selected filament, a thicker filament corresponding to a stronger stimulus was presented. In the event of paw withdrawal, the next weaker stimulus was chosen. Each hair was presented perpendicularly against the paw, with sufficient force to cause slight bending, and held 2-3 s. The stimulation of the same intensity was applied 5 times to the hindpaw at intervals of a few seconds. Three or more responses out of five stimulations were coded as a positive response. Once a positive response was detected, sequentially lower weight filaments were used to assess the sensory threshold for each paw. The allodynia scores were recorded in a blinded fashion.

Figure 4:
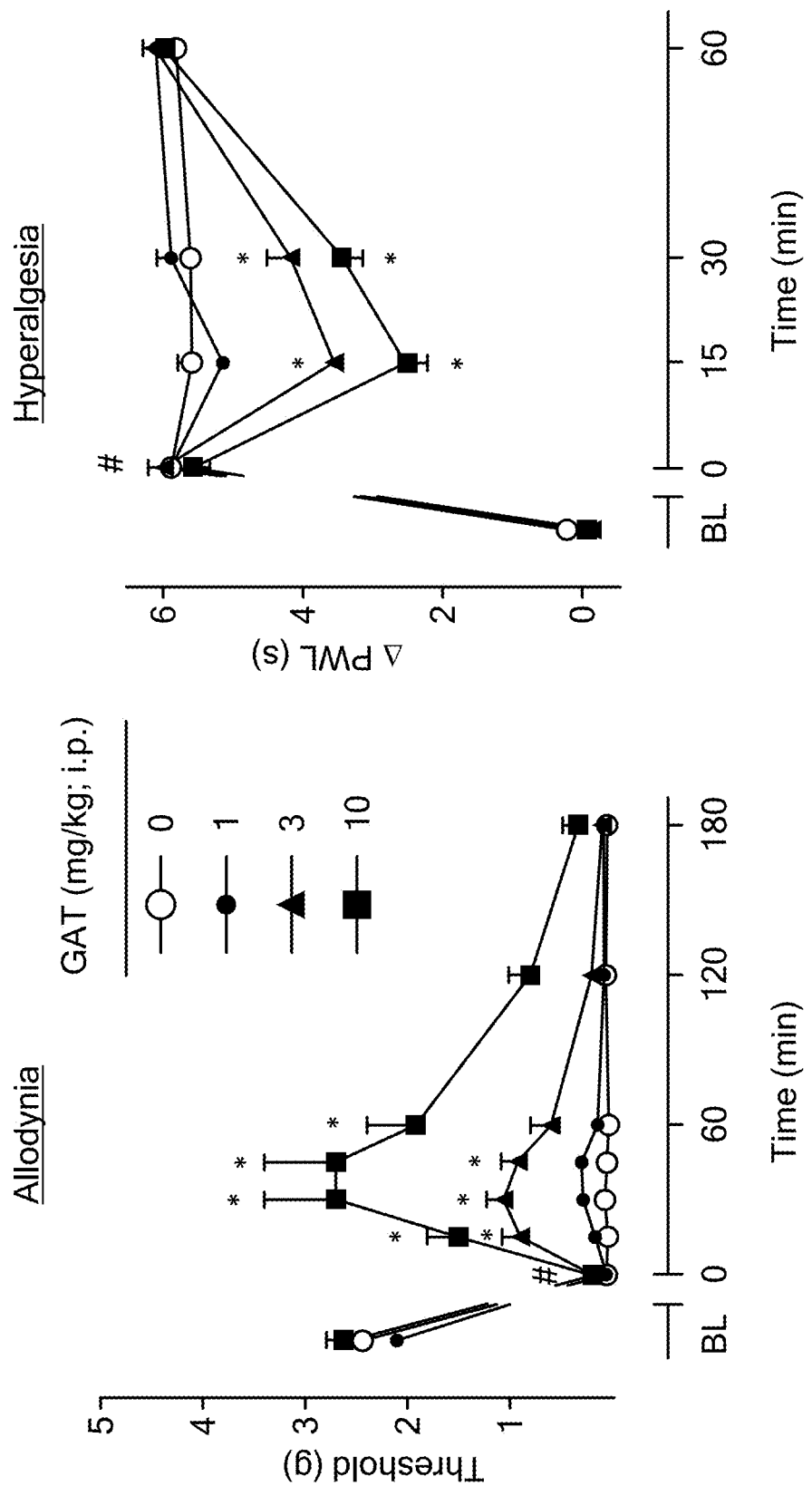
FIG. 4 shows the antinociceptive effect of GAT107 in a mouse model of chronic pain.

A similar sequence of drug treatment described for the formalin testing was used to test the antinociceptive effects of alpha-7 nAChRs ago-PAMs in the CFA model of inflammatory pain. Mice were given an intraplantar injection of 20 µl of CFA (0.5 mg/ml of heat killed *Mycobacterium tuberculosis*, Sigma, St. Louis, Mo.) in the intraplantar region of the right hindpaw of each mouse. Paw diameter and mechanical allodynia will be measured 3 days after CFA injection. We assessed the dose-response relationship of □7 nAChRs ago-PAMs (4 doses) in reversing CFA-induced mechanical allodynia and paw edema. The results are presented in FIG. 4.

GAT107's antiallodynic effect was dose dependent and lasted for 180 min (i.p.). Similarly, its antihyperalgesic effect was evident and lasted for 60 min. Both these actions of GAT107 were mediated via alpha-7 nAChRs since MLA blocked the effects (data not shown).

Chronic Constructive Injury Model

Mice were anesthetized with pentobarbital (45 mg/kg, i.p.). An incision was made just below the hipbone, parallel to the sciatic nerve. The right common sciatic nerve was exposed at the level proximal to the sciatic trifurcation, and a nerve segment 3-5 mm long was separated from surrounding connective tissue. Two loose ligatures with 6-0 silk suture were made around the nerve with a 1.0-1.5 mm interval between them. Muscles were closed with suture thread and the wound with wound clips. This procedure resulted in CCI of the ligated nerve. Any suture that remained after two weeks was removed from the healed surgical wound. Mechanical allodynia (von Frey test) was measured before and after drug injections.

The antiallodynic effects of test compounds were assessed in three experiments consisting of CCI mice and sham control mice. Only alpha-7 nAChRs PAMs/ago-PAMs that showed efficacy in the formalin test phase II with no significant degree of tolerance were tested in the CCI model. The anti-allodynic effects of alpha-7 nAChRs PAMs and ago-PAMs were tested (four doses and vehicle control, N=10 mice/group, administered i.p.) in the CCI model. Mice were assessed for mechanical allodynia 2 weeks after the CCI surgery. All these studies will be conducted in blinded manner. CCI and sham control mice received two conditioning sessions per day (vehicle in the morning and drug in the afternoon) over the course of 3 days, and were tested for a place preference on day 7 without any injections.

Pain behavioral data are presented as mean±S.E.M. (see FIGS. 5A and 5B). Statistical analysis was performed using the t-test or two-way analysis of variance test, followed by the post-hoc Bonferroni's test. All differences were considered significant at p<0.05, and significant differences are shown with asterisks in FIGS. 5A and 5B. $ED_{50}$ values with 95% confidence limits (CL) were calculated by unweighted least-squares linear regression.

Figure 5A:
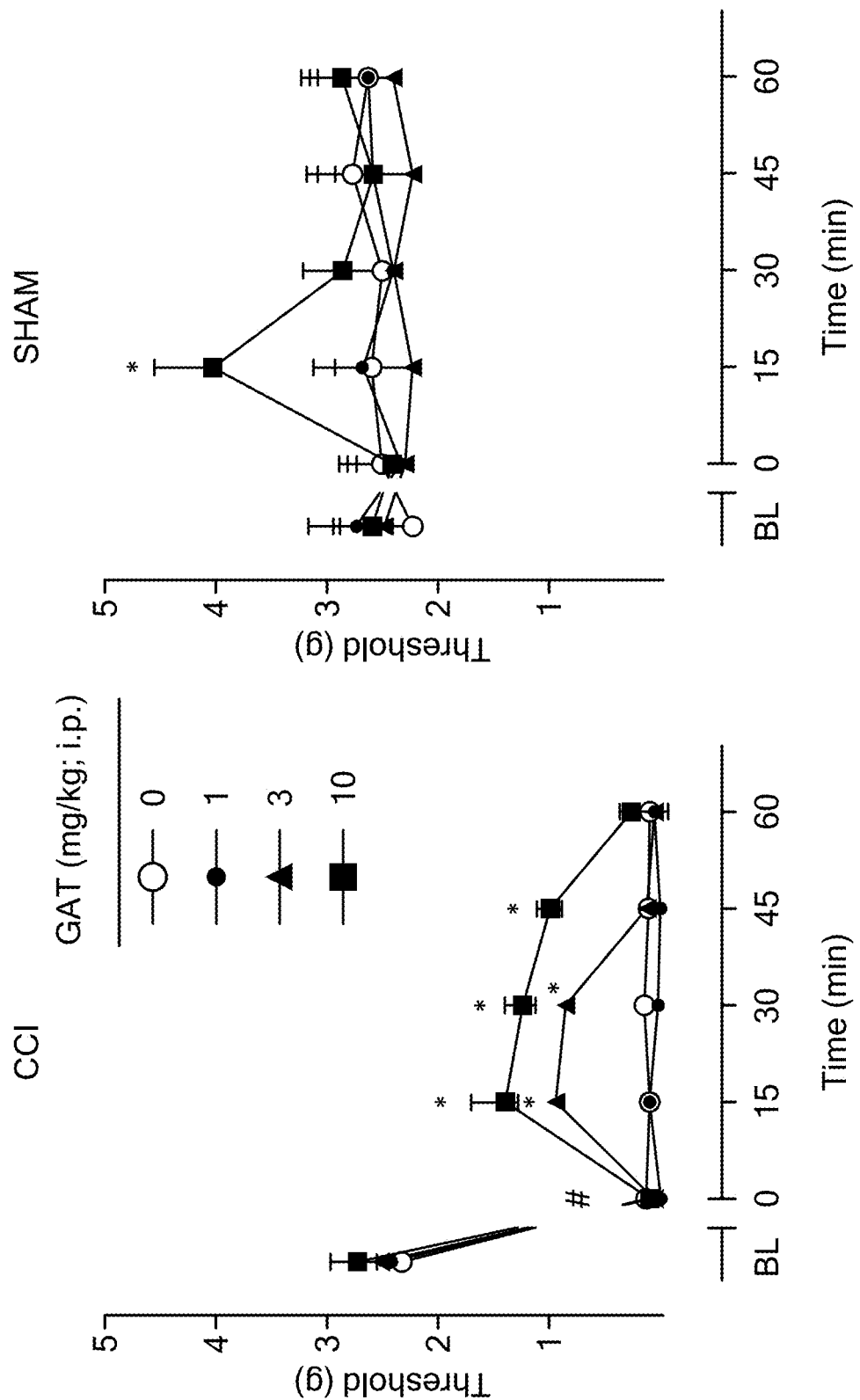
FIGS. 5A and 5B show antinociceptive effects of GAT107 (FIG. 5A) and GAT154 and GAT155 compounds (FIG. 5B) in a mouse model of neuropathic pain (CCI).
Figure 5B:
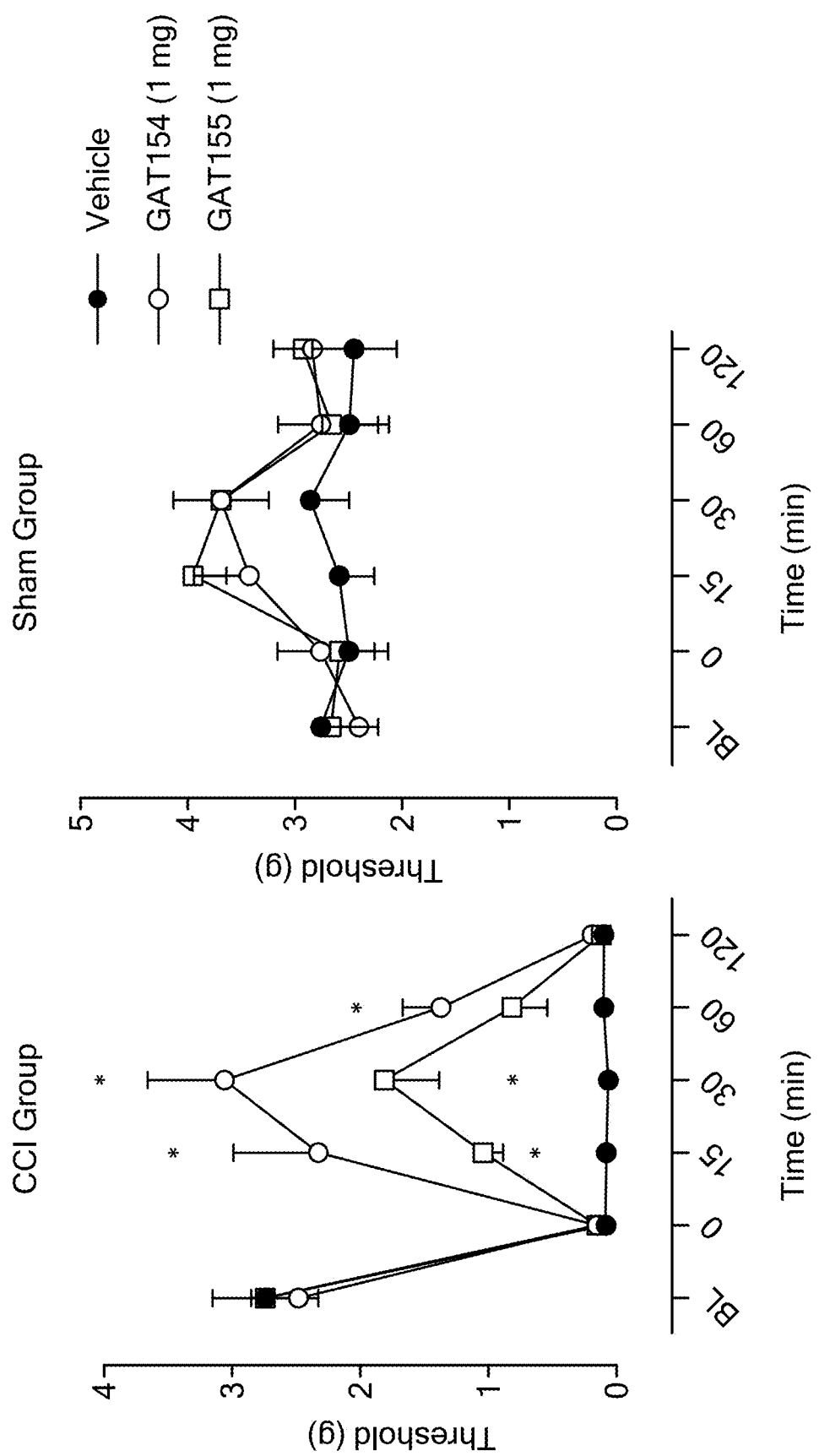

GAT107 exhibited a significant anti-allodynic effect in the CCI-mice in a dose-time dependent manner (FIG. 5A). There was no effect on sham mice (except at 15 min time point after the dose of 10 mg/kg) suggesting that the drug works only in a state of disease condition. GAT154 (ago-PAM) and GAT155 (PAM) also were studied in this model. Both compounds had almost equal peak efficacy in the presence of ACh (FIG. 5B) and displayed significantly better solubility compared to GAT107. GAT154 and GAT155 at the same dose of 1 mg/kg were effective in increasing the threshold for pain in the CCI model, but GAT154 twice as effective at every time point and completely reversed the effect without showing any significant effect on the sham mice.

Example 7. Effect of PAMs and Ago-PAMs for Alpha-7 nAChR on Memory

Figure 6:
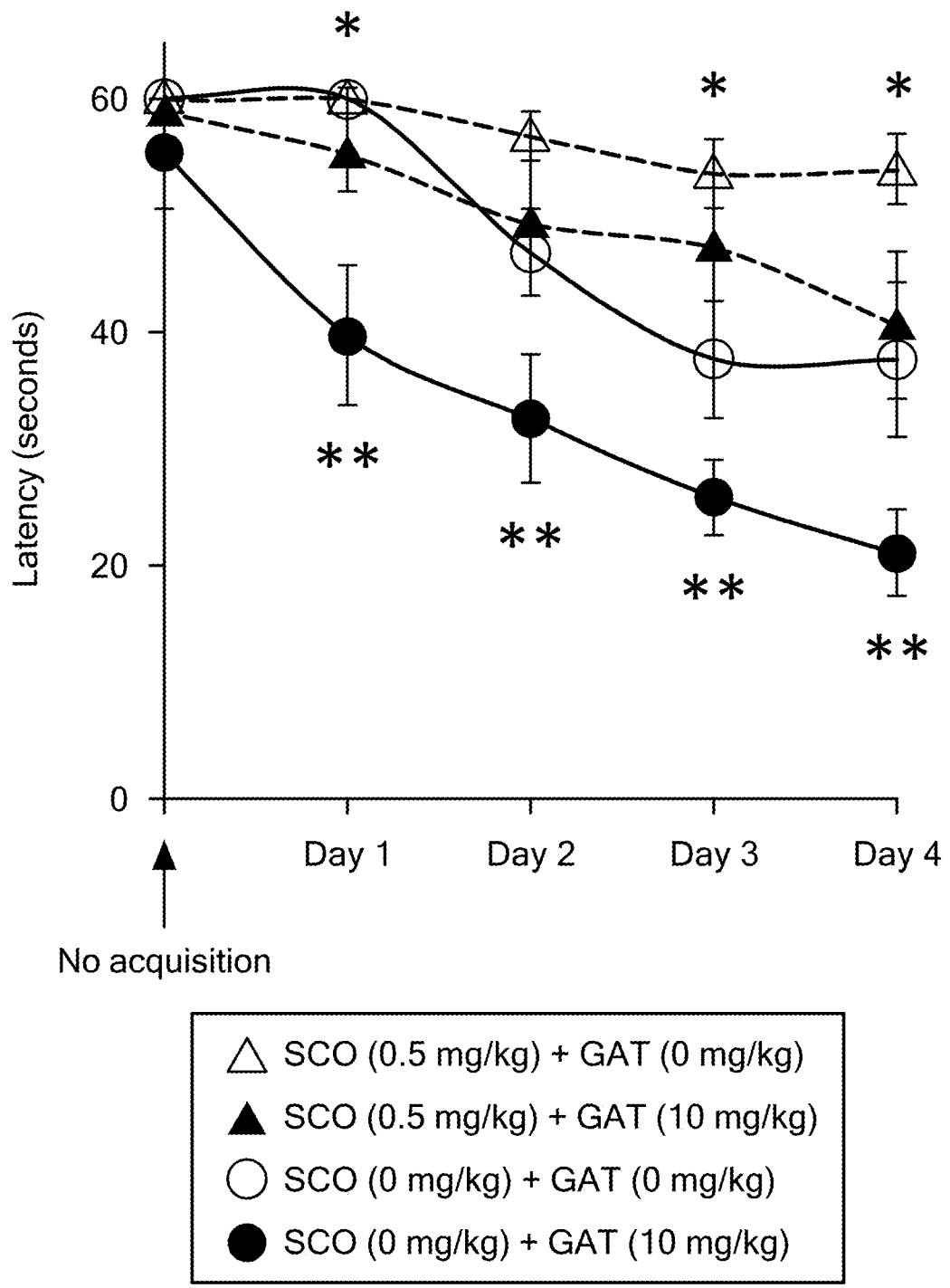
FIG. 6 shows the memory and cognition enhancing effects of GAT107 in a mouse model (Morris water maze).

FIG. 6 shows the results of a test to see if GAT107 has any effect on memory. This test was carried out in normal mice using a Morris water maze. GAT107 dose dependently reversed the memory defects seen in mice treated with scopolamine at the indicated concentrations; scopolamine is a cholinergic antagonist that causes loss of memory. When given to the mice alone, GAT107 reduced the latency for the mice to find the platform, thus indicating that this compound is nootropic and effective in enhancing memory and cognition even in normal mice.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

This application claims the priority of U.S. Provisional Application No. 62/028,009 filed 23 Jul. 2014 and entitled "Novel Ligands for the a7 Nicotinic Acetylcholine Receptors", the whole of which is hereby incorporated by reference.

The invention claimed is:
1. A compound having one of the following formulas:

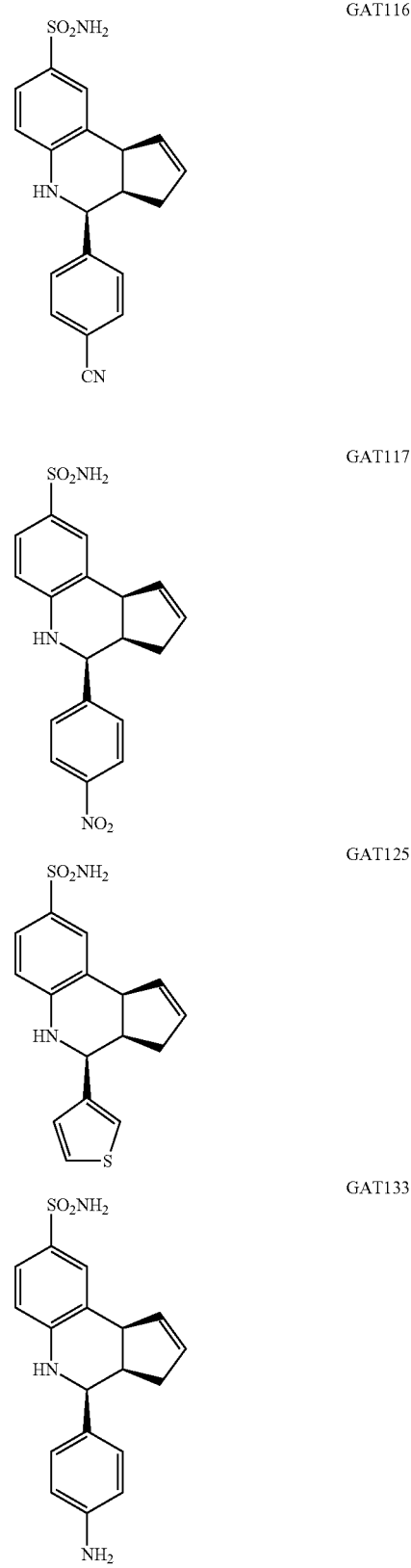

GAT141
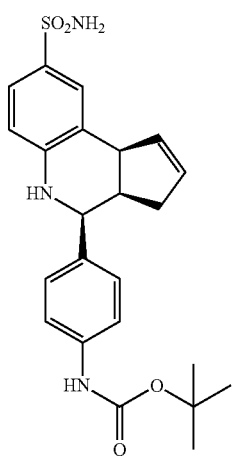
GAT143
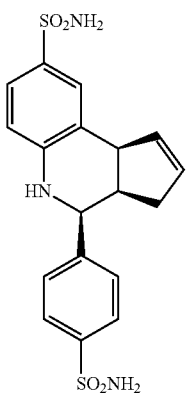
GAT146
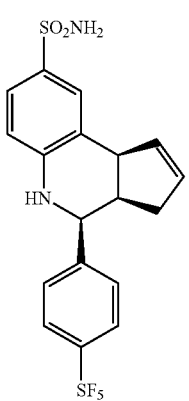
GAT149
GAT153
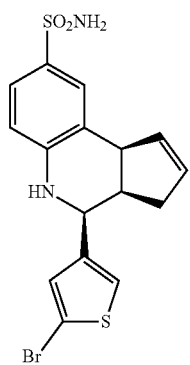
GAT154
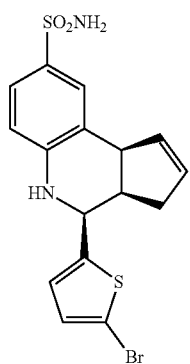
GAT155
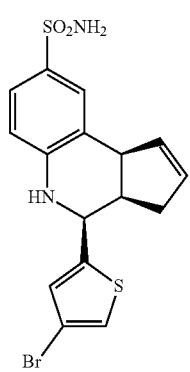
GAT156
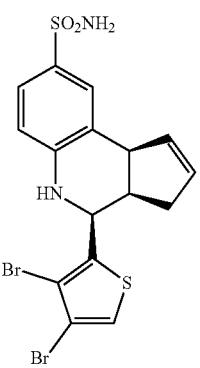

GAT157 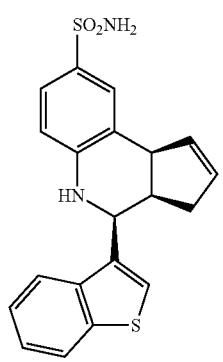
GAT159 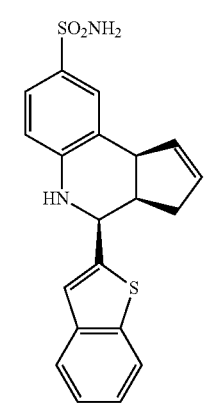
GAT162 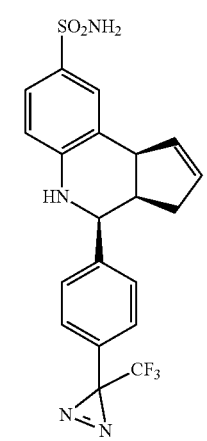
GAT164 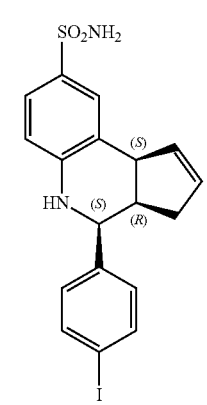
GAT166 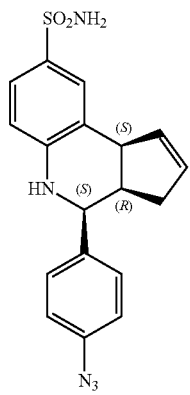
GAT181 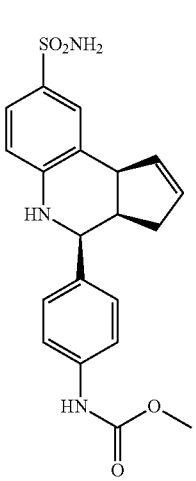
GAT182 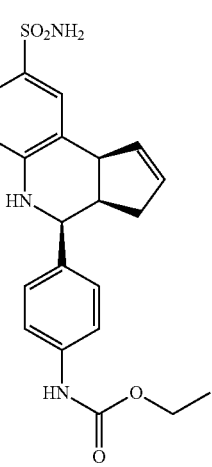

-continued
GAT186
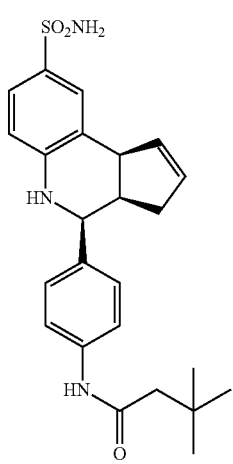
GAT187
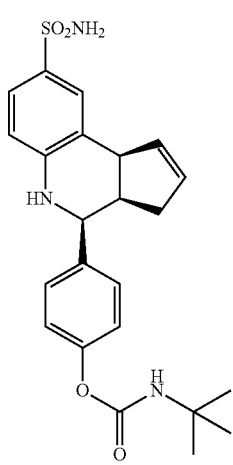
GAT188
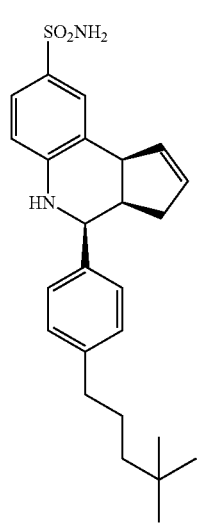
-continued
GAT189
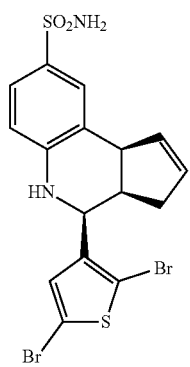
GAT190
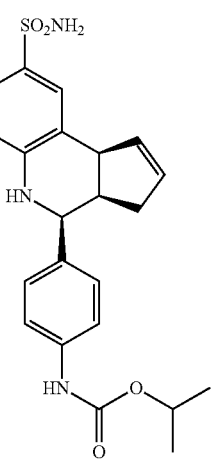
GAT191
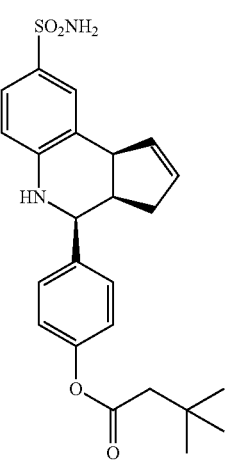

GAT192

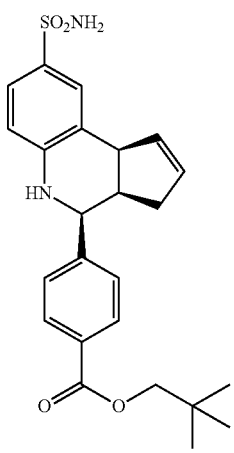

GAT193

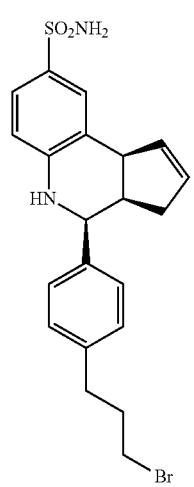

GAT913

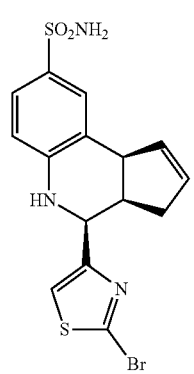

GAT922

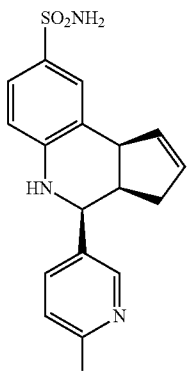

GAT924

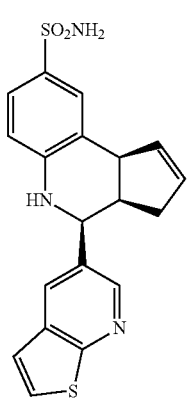

GAT925

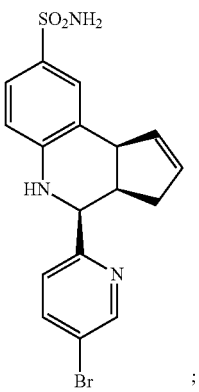

;

wherein the compound binds to an alpha-7 nicotinic acetylcholine receptor.

2. The compound of claim 1 which is substantially enantiomerically pure.

3. The compound of claim 1, wherein the compound comprises one or more of $^{18}F$, $^{19}F$, $^{75}Br$, $^{76}Br$, $^{123}I$, $^{124}I$, $^{125}I$, $^{131}I$, $^{11}C$, $^{13}C$, $^{13}N$, $^{15}O$, or $^{3}H$.

4. A radiolabeled compound of claim 3, or a pharmaceutically acceptable salt, hydrate, or solvate thereof, and an excipient.

5. The compound of claim 1, wherein the compound is a positive allosteric modulator of the alpha-7 nicotinic acetylcholine receptor.

6. The compound of claim 1, wherein the compound is an allosteric agonist of the alpha-7 nicotinic acetylcholine receptor.

7. The compound of claim 1, wherein the compound is capable of improving cognitive function, learning, and/or memory deficit.

8. The compound of claim 1, wherein the compound is capable of reducing inflammation.

9. The compound of claim 1, wherein the compound is capable of reducing neuropathic pain or pain related to a cognitive disorder.

10. A pharmaceutical composition comprising a compound of claim 1, or a pharmaceutically acceptable salt, hydrate, or solvate thereof, and an excipient.

* * * * *

UNITED STATES PATENT AND TRADEMARK OFFICE
CERTIFICATE OF CORRECTION

PATENT NO. : 11,299,496 B2
APPLICATION NO. : 15/328112
DATED : April 12, 2022
INVENTOR(S) : Thakur et al.

It is certified that error appears in the above-identified patent and that said Letters Patent is hereby corrected as shown below:

In the Specification

Column 1, Line 9, delete the following:
"The invention was developed with financial support from Grant No. GM057481 from the National Institutes of Health. The U.S. Government has certain rights in the invention."

And replace it with:
--This invention was made with government support under GM057481 awarded by the National Institutes of Health. The government has certain rights in the invention.--

Signed and Sealed this
Sixteenth Day of April, 2024

Katherine Kelly Vidal
*Director of the United States Patent and Trademark Office*